US006294176B1

(12) United States Patent
Cochran et al.

(10) Patent No.: US 6,294,176 B1
(45) Date of Patent: Sep. 25, 2001

(54) **RECOMBINANT RACCOONPOX VIRUS AND USES THEREOF AS A VACCINE IN MAMMALIAN AND AVIAN S

FIG. 2 Raccoonpox Virus Genomic Fragments HindIII "W", "T" and "P"

FIG. 3

Raccoonpox Virus Genomic Fragment HindIII "N" S-RPV-008 and S-RPV-009

```
HindIII                EcoRV    SnaBI                              HindIII
                      (1.5 KB)  (2.2 KB)
|─────────|─────────|─────────|─────────|─────────|
0         1         2         3         4         5  KB S-RPV-009  |─────────|───────────────────────────|
            1.5 KB              3.6 KB
                                                      ↓ Homology to
                                                        Variola Virus B22R
                                                        (amino acids 603-528)

S-RPV-008  |───────────────|──────────────────────|
                2.2 KB              2.9 KB
                                                      ↓ Homology to
                                                        Cowpox Virus D1L
                                                        (amino acids 206-104)
```

FIG. 4

Raccoonpox Virus Genomic Fragment HindIII "M"

Hind III — 0 — 1 — 2 — 3 — 4 — 5 — 6 KB — Hind III

Hpa I (4.1 KB)

↓ Homology to Cowpox Virus D1L (amino acids 386-434)

↓ Homology to Variola Virus D1L (amino acids 52-153)

↓ Homology to Vaccinia Virus C17L/B23R (amino acids 1-88)

FIG. 5 uidA gene/LP2EP2 promoter/EcoR I & BamH I insertion sites

FIG. 8    Raccoonpox Virus Genomic Fragment HindIII "S"

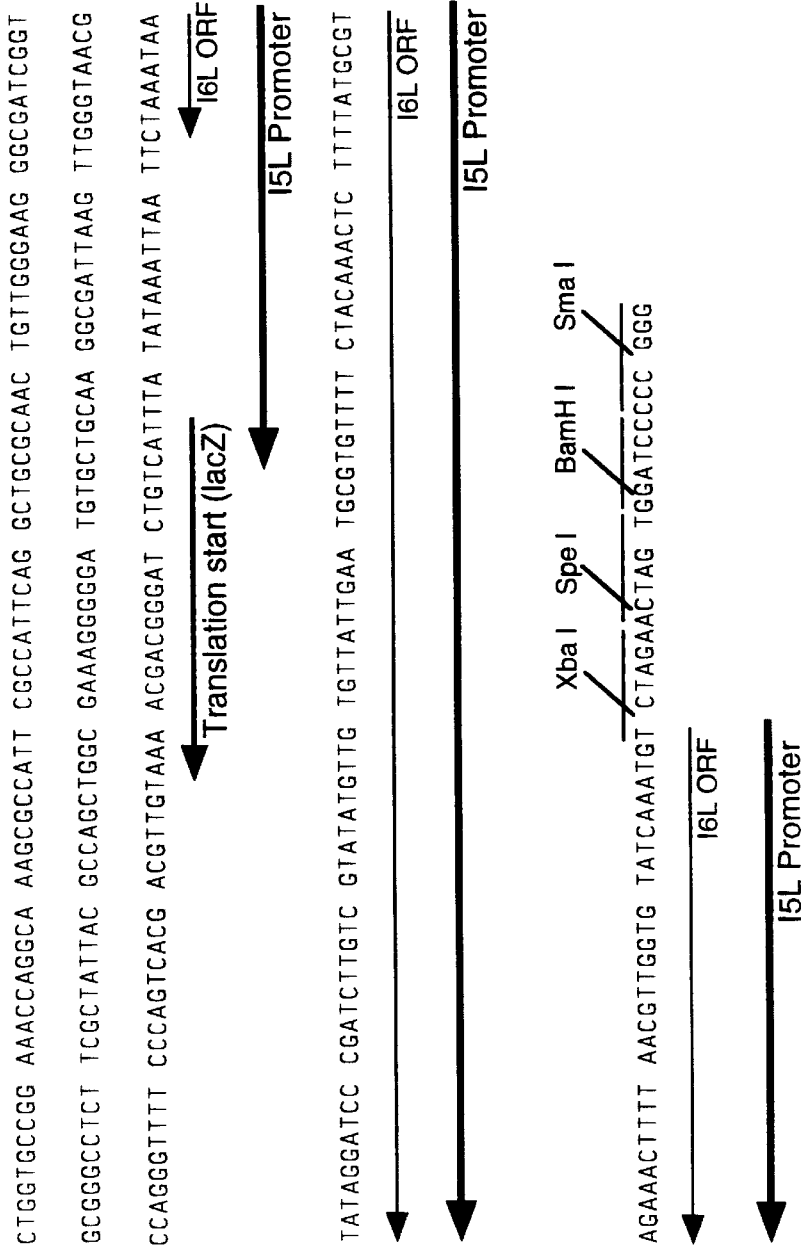
FIG. 9  Swinepox virus I5L Promoter

US 6,294,176 B1

RECOMBINANT RACCOONPOX VIRUS AND USES THEREOF AS A VACCINE IN MAMMALIAN AND AVIAN SPECIES

Within this application several publications are referenced by arabic numerals within parentheses. Full citations for these references may be found at the end of the specification immediately preceding the Sequence Listing. The disclosures of these publications in their entireties are hereby incorporated by reference into this application in order to more fully describe the state of the art as known to those skilled therein as of the date of the invention described and claimed herein.

BACKGROUND OF THE INVENTION

Raccoonpox virus (RPV) belongs to the orthopoxvirus family, like vaccinia virus, but has an advantage in that it is naturally attenuated and appears to be native to North America. Unlike swinepox virus whose infection in non-porcine species is non-productive, raccoonpox virus infection is productive, but may not spread systemically like vaccinia virus.

Raccoonpox virus was originally isolated from the upper respiratory tract of 2 of 92 apparently healthy raccoons in 1962 in Maryland (1). Significant HI (hemagglutinating-inhibiting) antibody titers for RPV were demonstrated in 23% [22/92] of raccoon sera indicating that RPV is indigenous in North America (2). Serological surveys testing sera from 593 raccoons in Delaware demonstrated that 4% were positive for RPV neutralizing antibodies, 12% were positive by ELISA and 2.5% of the sera were positive by both tests (10). RPV is classified as a orthopoxvirus based upon biological, serological and biophysical methods. RPV and volepox are the only orthopoxviruses thought to be native to North America. The Hind III DNA restriction map of RPV is the most divergent from other orthopoxvirus DNA maps, which are highly conserved, indicating that RPV has diverged from the other group members (4,6). Of 29 HindIII fragments from the RPV genome, none comigrated with HindIII fragments that were common to other examined orthopoxvirus DNA. RPV is naturally attenuated (10–100x) and avirulent compared with wild type vaccinia virus. There are four published RPV DNA sequences which include a Sal I end fragment (2.2 kb) (5), a hemagglutinin gene (1.5 kb) (7), a protein phosphatase sequence (0.5 kb; H1L) (15), and the TK gene (834 bp) (16). RPV TK shows 87% amino acid homology to TK of vaccinia and 84.3% nucleotide homology. RPV HA shows 53% amino acid homology with vaccinia HA and 66% nucleotide homology. No other information regarding the genomic organization of RPV is known.

To date, recombinant raccoon poxviruses have been generated by insertion of foreign genes such as rabies virus glycoprotein into the TK locus of raccoon poxvirus (7–14). RPV recombinants expressing foreign viral antigens have been shown to elicit host protective immune responses in non-raccoon species including dogs, cats, and sheep with no negative effects observed.

The present invention provides a recombinant raccoon poxvirus comprising a foreign DNA inserted into the HindIII M region, HindIII N region or HindIII U region of the raccoonpox virus genome. The recombinant raccoon poxvirus is useful as a vaccine in mammalian and avian species. Prior to the present invention, it was unknown whether non-essential regions existed in the HindIII M, HindIII N, or HindIII U regions, and whether a stable recombinant raccoonpox virus could be isolated with foreign DNA insertions into these regions.

SUMMARY OF THE INVENTION

The present invention provides a recombinant raccoonpox virus comprising a raccoonpox virus viral genome which contains a foreign DNA sequence inserted into a non-essential region within the HindIII "U" genomic region of the raccoonpox region of the raccoonpox virus genome.

The present invention provides a recombinant swinepox virus comprising a swinepox virus genome which contains a foreign DNA sequence inserted into a non-essential region of the raccoonpox virus genome, wherein the foreign DNA sequence is a host range gene selected from the group consisting of raccoonpox virus K1L and raccoonpox virus C7L.

The present invention provides a recombinant raccoonpox virus comprising a raccoonpox virus viral genome which contains a foreign virus viral genome which contains a foreign DNA sequence inserted into a non-essential region within the HindIII "N" genomic region of the raccoonpox virus genome.

The present invention provides a recombinant raccoonpox virus comprising a raccoonpox virus viral genome which contains a foreign DNA sequence inserted into a non-essential region within the HindIII "M" genomic region of the raccoonpox virus genome.

The present invention provides a recombinant raccoonpox virus comprising a raccoonpox virus viral genome which contains a deletion in a raccoonpox virus host range gene of the viral genome, wherein the raccoonpox virus host range gene is selected from the group consisting of C7L, C6L, C5L, C4L, C3L, C2L, C1L, N1L, N2L, M1L, M2L, and K1L.

The present invention provides a homology vector for producing a recombinant raccoonpox virus by inserting a foreign DNA sequence into the raccoonpox virus genome which comprises a double-stranded DNA molecule consisting of double-stranded foreign DNA sequence encoding an antigenic polypeptide derived from an animal pathogen. Located at one end of the foreign DNA sequence, is double-stranded feline virus genomic DNA homologous to the genomic DNA located at one side of a non-essential site of the raccoonpox viral genomic DNA. Located at the other end of the foreign DNA sequence, is double-stranded raccoonpox virus genomic DNA homologous to the genomic DNA located at the other side of the same site.

BRIEF DESCRIPTION OF THE FIGURES

FIG. 2: Restriction endonuclease map of raccoonpox virus HindIII "W", "T", and "P", genomic fragments (approximately 8300 base pairs) (SEQ ID NO. 5, 12). At least seven open reading frames (ORFs) within this region are the N1L vaccinia homologue (SEQ ID NO. 6), N2L vaccinia homologue (SEQ ID NO. 7), M1L vaccinia homologue (SEQ ID NO. 8), M2L vaccinia homologue (SEQ ID NO. 9), K1L vaccinia homologue (SEQ ID NO. 10), K2L vaccinia homologue (SEQ ID NO. 11), and the K7R vaccinia homologue (SEQ ID NO. 13). (17) These seven ORFs are non-essential for viral replication and suitable for insertion of foreign DNA. Restriction endonuclease sites in the RPV HindIII W, T and P genomic fragments are shown as suitable insertion sites.

FIG. 3: Restriction endonuclease map of raccoonpox virus HindIII "N" genomic fragment (approximately 5,100 base pairs). At least two open reading frames (ORFs) are the D1L cowpox virus homologue (18) and the B22R variola virus homologue. These two ORFs are non-essential for viral replication and suitable for insertion of foreign DNA. Restriction endonuclease sites in the RPV HindIII N genomic fragment are shown as suitable insertion sites. Examples of recombinant raccoonpox of the present invention have foreign DNA inserted into the EcoRV site at approximately nucleotide 1500 (S-RPV-009) or SnaBI site at approximately nucleotide 2200 (S-RPV-008) of the HindIII U fragment.

FIG. 4: Restriction endonuclease map of raccoonpox virus HindIII "M" genomic fragment (approximately 6,000 base pairs). At least three open reading frames (ORFs) within this region are the D1L cowpox virus homologue (18) the C17L/B23R vaccinia virus homologue (17) and the D1L variola virus homologue (17). These three ORFs are non-essential for viral replication and suitable for insertion of foreign DNA. Restriction endonuclease sites in the RPV HindIII M genomic fragment are shown as suitable insertion sites. Examples of recombinant raccoonpox of the present invention have foreign DNA inserted into the HpaI site at approximately nucleotide 4100 (S-RPV-010) of the HindIII M fragment.

FIG. 8: Restriction endonuclease map of raccoonpox virus HindIII "S" genomic fragment (approximately 2,375 base pairs). At least two open reading frames (ORFs) are the B19R vaccinia virus homologue (Surface antigen; IL-1 receptor) (17) and the B18R variola virus homologue (787 amino acids) (17); B20R vaccinia virus homologue (127 amino acids) (17). These three ORFs are non-essential for viral replication and suitable for insertion of foreign DNA. Restriction endonuclease sites in the RPV HindIII S genomic fragment are shown as suitable insertion sites. Examples of recombinant raccoonpox of the present invention have foreign DNA inserted into the HpaI site at approximately nucleotide 4100 (S-RPV-010) of the HindIII M fragment.

FIG. 9: DNA sequence of the swinepox virus I5L promoter and location of the translation start codon. Direction of transcription is from right to left. (SEQ ID NO. 58) The swinepox virus I5L promoter is useful for expression of foreign DNA in recombinant poxvirus vectors, including, but not limited to raccoonpox, swinepox, avipox, fowlpox, canarypox, cowpox, capripox, and vaccinia virus.

DETAILED DESCRIPTION OF THE INVENTION

Figure 1:
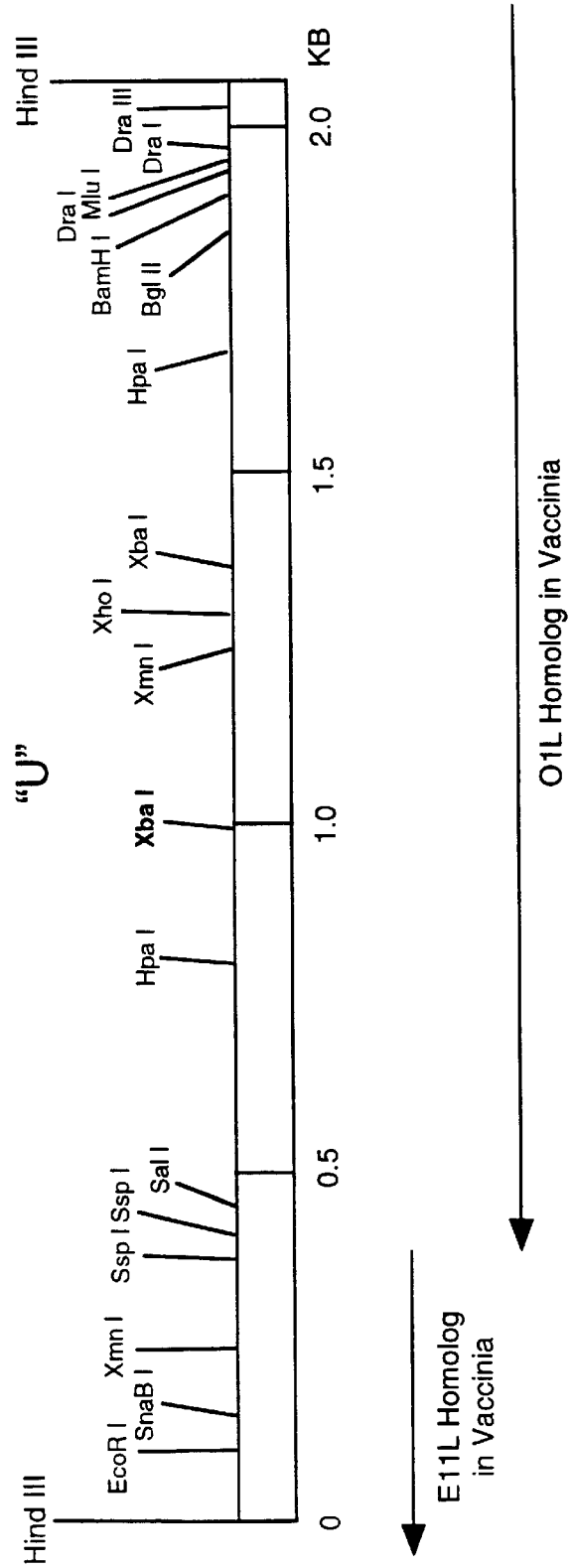
FIG. 1: Restriction endonuclease map of raccoonpox virus HindIII "U" genomic fragment (approximately 2055 base pairs) (SEQ ID NO. 1). Two open reading frames (ORFS) are the O1L vaccinia homologue (SEQ ID NO. 3) and the E11L vaccinia homologue (SEQ ID NO. 2). (17) These two ORFs are non-essential for viral replication and suitable for insertion of foreign DNA. Restriction endonuclease sites in the RPV HindIII U genomic fragment are shown as suitable insertion sites. Examples of recombinant raccoonpox of the present invention have foreign DNA inserted into the XbaI site at nucleotide 1065 of the HindIII U fragment.

The present invention provides a recombinant raccoonpox virus comprising a raccoonpox virus viral genome which contains a foreign DNA sequence inserted into a non-essential region within the HindIII "U" genomic region of the raccoonpox region of the raccoonpox virus genome. The present invention is useful for the expression of a foreign DNA or genes from other pathogens for protection against disease. Recombinant raccoonpox virus expressing a foreign DNA from avian or mammalian pathogens are useful as vaccines in avian or mammalian species including but not limited to feline, canine, equine, bovine, caprine, porcine, and primate, including human.

As defined herein, "viral genome" means the entire DNA which naturally occurs in the virus. As defined herein, "foreign DNA" or "foreign gene" means any DNA or gene that is exogenous to a genome.

In one embodiment of the present invention, the foreign DNA sequence is inserted into an O1L open reading frame. In another embodiment, the foreign DNA is inserted into an E11 open reading frame. In another embodiment, the foreign DNA sequence is inserted into an intergenic region. In another embodiment, the foreign DNA sequence is inserted into an XbaI restriction endonuclease site.

A further embodiment of the recombinant raccoonpox virus comprising a raccoonpox virus viral genome which contains a foreign DNA sequence inserted into a non-essential region within the HindIII "U" genomic region of the raccoonpox virus genome, further comprises the foreign DNA sequence inserted into the HindIII "U" genomic region, wherein the foreign DNA is capable of being expressed in a recombinant raccoonpox virus host cell.

One embodiment of the present invention is wherein the foreign DNA sequence encodes a screenable marker. Another embodiment is wherein the screenable marker is E. coli beta-galactosidase or E. coli beta-glucuronidase. A further embodiment is wherein the foreign DNA sequence encodes an antigenic polypeptide. Another embodiment of the present invention is wherein the antigenic polypeptide when introduced into the host cell, induces production of protective antibodies against a feline disease-causing agent from which the antigenic polypeptide is derived or derivable. A further embodiment of the present invention is wherein the antigenic polypeptide is derived or derivable from a group consisting of feline pathogen, canine pathogen, equine pathogen, bovine pathogen, caprine pathogen, avian pathogen, porcine pathogen, or human pathogen.

Another embodiment of the invention is wherein the foreign DNA sequence is selected from a group consisting of swine influenza virus hemagglutinin, swine influenza virus neuraminidase, porcine reproductive and respiratory virus (PRRS) ORF2, PRRS ORF3, PRRS ORF4, PRRS ORF5, PRRS ORF6, PRRS ORF7, porcine parvovirus VP2.

Another embodiment of the invention is wherein the foreign gene is under control of an endogenous upstream, raccoonpox virus promoter. A further embodiment of the present invention is wherein promoter is selected from a group consisting of the raccoonpox virus E11L promoter and the raccoonpox virus O1L promoter. Another embodiment is wherein the foreign gene is under control of a heterologous upstream promoter.

A further embodiment of the invention is wherein the promoter is selected from a group consisting of the synthetic pox late promoter 1 (LP1), the synthetic pox early promoter 1 (EP1), the synthetic early promoter 2 (EP2), the synthetic pox late promoter 2 early promoter 2 (LP2EP2), the synthetic pox late promoter 1 (LP1), the synthetic pox late promoter 2 (LP2), and the swinepox virus I5L promoter.

One embodiment of the invention is a recombinant raccoonpox virus designated S-RPV-001, designated S-RPV-002, designated S-RPV-003, designated S-RPV-004, designated S-RPV-005, designated S-RPV-006, designated S-RPV-007, designated S-RPV-011, designated S-RPV-012, designated S-RPV-013, designated S-RPV-015, designated S-RPV-016, designated S-RPV-017, designated S-RPV-018, designated S-RPV-019, designated S-RPV-020, or designated S-RPV-028.

The present invention also provides for a recombinant swinepox virus of comprising a swinepox virus genome which contains a foreign DNA sequence inserted into a non-essential region of the swinepox virus genome, wherein the foreign DNA sequence is a host range gene selected from the group consisting of raccoonpox virus K1L and raccoonpox virus C7L. One embodiment of the present invention is the recombinant swinepox virus further comprising a second foreign DNA sequence inserted into a non-essential region within the swinepox virus genome. One embodiment of the present invention is the recombinant swinepox virus designated S-SPV-248. Another embodiment of the present invention is the recombinant swinepox virus designated S-SPV-249.

The present invention also provides a recombinant raccoonpox virus comprising a raccoonpox virus viral genome which contains a foreign DNA sequence inserted into a non-essential region within the HindIII "N" genomic region of the raccoonpox virus genome. A further embodiment of the present invention is wherein the foreign DNA sequence is inserted into an SnaBI restriction endonuclease site. Another embodiment of the present invention is wherein the foreign DNA sequence is inserted into an EcoRV restriction endonuclease site.

A preferred embodiment of the present invention is a recombinant raccoonpox virus designated S-RPV-008 or designated S-RPV-009.

The present invention provides for a recombinant raccoonpox virus comprising a raccoonpox virus viral genome which contains a foreign DNA sequence inserted into a non-essential region within the HindIII "M" genomic region of the raccoonpox virus genome. One embodiment of the present invention is wherein the foreign DNA sequence is inserted into an HpaI restriction endonuclease site. Another embodiment of the present invention is wherein the recombinant virus is designated S-RPV-010.

The present invention also provides for a recombinant raccoonpox virus comprising a raccoonpox virus viral genome which contains a deletion in a raccoonpox virus host range gene of the viral genome, wherein the raccoonpox virus host range gene is selected from the group consisting of C7L, C6L, C5L, C4L, C3L, C2L, C1L, N1L, N2L, M1L, M2L, and K1L. One embodiment of the present invention is a recombinant raccoonpox virus further comprising a second foreign DNA sequence inserted into a non-essential region within the raccoonpox virus genome.

The present invention also provides for a homology vector for producing a recombinant raccoonpox virus by inserting a foreign DNA sequence into the raccoonpox virus genome which comprises a double-stranded DNA molecule consisting of: (a) double-stranded foreign DNA sequence encoding an antigenic polypeptide derived from an animal pathogen; (b) at one end of the foreign DNA sequence, double-stranded feline virus genomic DNA homologous to the genomic DNA located at one side of a non-essential site of the raccoonpox viral genomic DNA; (c) at the other end of the foreign DNA sequence, double-stranded raccoonpox virus genomic DNA homologous to the genomic DNA located at the other side of the same site.

In one embodiment of the homology vector the antigenic polypeptide is selected from a group consisting of swine influenza virus hemagglutinin, swine influenza virus neuraminidase, porcine reproductive and respiratory virus (PRRS) ORF2, PRRS ORF3, PRRS, ORF4, PRRS ORF5, PRRS ORF6, PRRS ORF7, porcine parvovirus VP2, E. coli beta-galactosidase gene., E. Coli beta-glucuronidase gene.

A further embodiment is a homology vector designated Homology Vector 902-16.2. Another embodiment is a homology vector designated Homology Vector 902-19.18. A further embodiment is a homology vector designated Homology Vector 902-49.5. A further embodiment is a homology vector designated Homology Vector 902-49.14. A further embodiment is a homology vector designated Homology Vector 902-49.23.

Another embodiment is a homology vector designated Homology Vector 902-49.34. A further embodiment is a homology vector designated Homology Vector 934-65.1, or Homology Vector 934-64.2 or Homology Vector 938-94.1 or Homology Vector 938-94.25 or Homology Vector 950-13.4 or Homology Vector 936-87.2 or Homology Vector 950-16.34.

The present invention provides for a host cell infected with the recombinant raccoonpox virus comprising a raccoonpox virus viral genome which contains a foreign DNA sequence inserted into a non-essential region within the HindIII "U" genomic region of the raccoonpox virus genome. One embodiment of the present invention is wherein the host cell is mammalian cell.

The present invention also provides for a vaccine against an animal pathogen which comprises an effective immunizing amount of the recombinant raccoonpox virus and a suitable carrier.

The present invention also provides for a method of immunizing an animal against an animal pathogen which comprises administering to the animal an effective immunizing dose of the vaccine.

The present invention also provides for a method of immunizing an animal against a feline pathogen which comprises administering to the animal an effective immunizing dose of the vaccine.

The present invention provides for a recombinant raccoonpox virus comprising a raccoonpox virus viral genome which contains a foreign DNA sequence inserted into a non-essential region within the HindIII "U" genomic region of the raccoonpox region of the raccoonpox virus genome.

In one embodiment the foreign DNA sequence is inserted into an O1L open reading frame.

In another embodiment the foreign DNA sequence is inserted into an E11L open reading frame.

In one embodiment the foreign DNA sequence is inserted into an intergenic region.

In a further embodiment the foreign DNA sequence is inserted into an XbaI restriction endonuclease site.

In another embodiment the recombinant raccoonpox virus offurther comprises the foreign DNA sequence inserted into the HindIII "U" genomic region, wherein the foreign DNA is capable of being expressed in a recombinant raccoonpox virus host cell.

In another embodiment the foreign DNA sequence encodes a screenable marker.

In another embodiment the screenable marker is E. coli beta-galactosidase.

In another embodiment the screenable marker is E. coli beta-glucuronidase.

In one embodiment the foreign DNA sequence encodes an antigenic polypeptide.

In another embodiment the antigenic polypeptide when introduced into the host cell, induces production of protective antibodies against a feline disease-causing agent from which the antigenic polypeptide is derived or derivable.

In another embodiment the antigenic polypeptide is derived or derivable from a group consisting of feline pathogen, canine pathogen, equine pathogen, bovine pathogen, caprine pathogen, avian pathogen, porcine pathogen, or human pathogen.

In another embodiment the foreign DNA sequence is selected from a group consisting of swine influenza virus hemagglutinin, swine influenza virus neuraminidase, porcine reproductive and respiratory virus (PRRS) ORF2, PRRS ORF3, PRRS ORF4, PRRS ORF5, PRRS ORF6, PRRS ORF7, porcine parvovirus VP2.

In another embodiment the foreign gene is under control of an endogenous upstream, raccoonpox virus promoter.

In another embodiment the promoter is selected from a group consisting of the raccoonpox virus E11L promoter and the raccoonpox virus O1L promoter.

In another embodiment the foreign gene is under control of a heterologous upstream promoter.

In another embodiment the promoter is selected from a group consisting of the synthetic pox late promoter 1 (LP1), the synthetic pox early promoter 1 (EP1), the synthetic pox early promoter 2 (EP2), the synthetic pox late promoter 2 early promoter 2 (LP2EP2), the synthetic pox late promoter 1 (LP1), the synthetic pox late promoter 2 (LP2), and the swinepox virus I5L promoter.

The present invention provides for a recombinant raccoonpox virus designated S-RPV-001, S-RPV-002, S-RPV-003 S-RPV-004, S-RPV-005, S-RPV-006, S-RPV-007, S-RPV-011, S-RPV-012, S-RPV-013, S-RPV-015, S-RPV-016, S-RPV-017, S-RPV-018, S-RPV-019, S-RPV-020, or S-RPV-028.

The present invention provides for a recombinant swinepox virus comprising a swinepox virus genome which contains a foreign DNA sequence inserted into a non-essential region of the raccoonpox virus genome, wherein the foreign DNA sequence is a host range gene selected from the group consisting of raccoonpox virus K1L and raccoonpox virus C7L.

In one embodiment the recombinant swinepox virus of further comprises a second foreign DNA sequence inserted into a non-essential region within the swinepox virus genome.

In one embodiment the recombinant swinepox virus is designated S-SPV-248 or S-SPV-249.

The present invention provides for a recombinant raccoonpox virus comprising a raccoonpox virus viral genome which contains a foreign virus viral genome which contains a foreign DNA sequence inserted into a non-essential region within the HindIII "N" genomic region of the raccoonpox virus genome.

In one embodiment the foreign DNA sequence is inserted into an EcoRI restriction endonuclease site.

In another embodiment the foreign DNA sequence is inserted into an SnaBI restriction endonuclease site.

The present invention provides for a recombinant raccoonpox virus of designated S-RPV-008 or S-RPV-009.

The present invention provides for a recombinant raccoonpox virus comprising a raccoonpox virus viral genome which contains a foreign DNA sequence inserted into a non-essential region within the HindIII "M" genomic region of the raccoonpox virus genome.

In one embodiment the foreign DNA sequence is inserted into an HpaI restriction endonuclease site.

The present invention provides for a recombinant raccoonpox virus ofdesignated S-RPV-010.

The present invetion provides for a recombinant raccoonpox virus comprising a raccoonpox virus viral genome which contains a deletion in a raccoonpox virus host range gene of the viral genome, wherein the raccoonpox virus host range gene is selected from the group consisting of C7L, C6L, C5L, C4L, C3L, C2L, C1L, N1L, N2L, M1L, M2L, and K1L.

In one embodiment the recombinant raccoonpox virus of, further comprises a second foreign DNA sequence inserted into a non-essential region within the raccoonpox virus genome.

The present invention provides for a homology vector for producing a recombinant racconpox virus by inserting a foreign DNA sequence into the racconpox virus genome which comprises a double-stranded DNA molecule consisting of double-stranded foreign DNA sequence encoding an antigenic polypeptide derived from an animal pathogen; at one end of the foreign DNA sequence, double-stranded feline virus genomic DNA homologous to the genomic DNA located at one side of a non-essential site of the raccoonpox viral genomic DNA; at the other end of the foreign DNA sequence, double-stranded raccoonpox virus genomic DNA homologous to the genomic DNA located at the other side of the same site.

In one embodiment the antigenic polypeptide is selected from a group consisting of swine influenza virus hemagglutinin, swine influenza virus neuraminidase, porcine reproductive and respiratory virus (PRRS) ORF2, PRRS ORF3, PRRS, ORF4, PRRS ORF5, PRRS ORF6, PRRS ORF7, porcine parvovirus VP2, E. coli beta-galactosidase gene., and E. Coli beta-glucuronidase gene.

The present invention provides for a homology vector designated Homology Vector 902-16.2, Homology Vector 902-19.18, Homology Vector 902-49.5, Homology Vector 902-49.14, Homology Vector 902-49.23, Homology Vector 902-49.34, Homology Vector 934.65-1, Homology Vector 934-64.2, Homology Vector 938-94.1 Homology Vector 938-94.25, Homology Vector 950-13.4, Homology Vector 936-87.2, Homology Vector 950-16.34, The present invention provides for a host cell infected with a recombinant raccoonpox comprising a raccoonpox virus viral genome which contains a foreign DNA sequence inserted into a non-essential region within the HindIII "U" genomic region of the raccoonpox region of the raccoonpox virus genome.

In one embodiment the host cell is mammalian cell.

The present invention provides for a vaccine against an animal pathogen which comprises an effective immunizing amount of a recombinant raccoonpox virus and a suitable carrier.

The present invention provides for a method of immunizing an animal against an animal pathogen which comprises administering to the animal an effective immunizing dose of a recombinant raccoonpox virus and a suitable carrier.

The present invention provides for a method of immunizing an animal against a feline pathogen which comprises administering to the animal an effective immunizing dose of a recombinant raccoonpox virus and a suitable carrier.

The invention provides a recombinant raccoonpox virus capable of replication which contains foreign DNA encoding an antigenic polypeptide which is useful to prevent disease in porcine, bovine, feline, canine, avian, equine, caprine and human species.

The invention provides a recombinant raccoonpox virus capable of replication which contains foreign DNA encoding an antigenic polypeptide which is or is from pseudorabies virus (PRV) g50 (gD), pseudorabies virus (PRV) gII (gB), Pseudorabies virus (PRV) gIII (gC), pseudorabies virus (PRV) glycoprotein H, pseudorabies virus (PRV) glycoprotein E, Transmissible fungastroenteritis (TGE) glycoprotein 195, Transmissible gastroenteritis (TGE) matrix protein, swine rotavirus glycoprotein 38, swine parvovirus capsid protein, Serpulina hydodysenteriae protective antigen, Bovine Viral Diarrhea (BVD) glycoprotein 55, swine influenza hemagglutinin or swine influenza neuraminidase. Preferably, the antigenic polypeptide is Pseudorabies Virus (PRV) g50 (gD). Preferably the antigenic polypeptide is swine influenza hemagglutinin or swine influenza neuraminidase.

The present invention further provides an antigenic polypeptide which includes, but is not limited to: hog cholera virus gEl, hog cholera virus gE2, swine influenza virus hemagglutinin, neurominidase, matrix and nucleoprotein, pseudorabies virus gB, gC and gD, and porcine reproductive and respiratory disease (PRRS) virus ORF2, ORF3, ORF4, ORF5, ORF6 and ORF7. Preferably the antigenic polypeptide is PRRS, ORF2, ORF3, ORF4, ORF5, ORF6, and ORF 7.

The invention further provides a recombinant raccoonpox virus capable of replication which contains foreign DNA encoding an antigenic polypeptide which is or is from Serpulina hyodysenteriae, Foot and Mouth Disease Virus, Hog Cholera Virus, Swine Influenza Virus, African Swine Fever Virus or Mycoplasma hyopneumoniae.

The invention further provides a recombinant raccoonpox virus capable of replication which contains foreign DNA encoding an antigenic polypeptide which is or is from feline leukemia virus, feline immunodeficiency virus and *Dirofilaria immitis* (heartworm). Additional antigens from disease causing microorganisms are expressed in raccoonpox virus. Disease causing microorganisms in cats include, but are not limited to *Dirofilaria immitis* p39 and 22kD antigens, feline infectious peritonitis virus, calicivirus, rabies virus, feline parvovirus (panleukopenia virus), feline coronavirus and feline Chlamydia, *Toxoplasma gondii*. Disease causing microorganisms in dogs include, but are not limited to canine distemper, canine adenovirus type 1 (hepatitis), adenovirus type 2 (respiratory disease), parainfluenza, *leptospira canicola*, icterohemorragia, parvovirus, coronavirus, *borrelia burgdorferi*, canine herpesvirus, *bordetella bronchiseptica* and rabies virus.

The present invention further provides a recombinant raccoonpox virus which comprises a foreign DNA sequence inserted into a non-essential site of the raccoonpox genome, wherein the foreign DNA sequence encodes an antigenic polypeptide derived from infectious laryngotracheitis virus and is capable of being expressed in a host infected by the recombinant raccoonpox virus. Examples of such antigenic polypeptide are infectious laryngotracheitis virus glycoprotein G, glycoprotein D and glycoprotein I, Newcastle Disease Virus (NDV) hemagglutinin-neuraminidase, NDV fusion protein (F).

In one embodiment of the recombinant raccoonpox virus the foreign DNA sequence encodes a cytokine. In another embodiment the cytokine is chicken myelomonocytic growth factor (cMGF) or chicken interferon (cIFN). Cytokines include, but are not limited to: transforming growth factor beta, epidermal growth factor family, fibroblast growth factors, hepatocyte growth factor, insulin-like growth factor, vascular endothelial growth factor, interleukin 1, IL-1 receptor antagonist, interleukin-2, interleukin-3, interleukin-4, interleukin-5, interleukin-6, IL-6 soluble receptor, interleukin-7, interleukin-8, interleukin-9, interleukin-10, interleukin-11, interleukin-12, interleukin-13, interleukin-14, interleukin-15, interleukin-16, angiogenin, chemokines, colony stimulating factors, granulocyte-macrophage colony stimulating factors, erythropoietin, interferon, interferon gamma, c-kit ligand, leukemia inhibitory factor, oncostatin M, pleiotrophin, secretory leukocyte protease inhibitor, stem cell factor, tumor necrosis factors, and soluble TNF receptors. These cytokines are from humans, bovine, equine, feline, canine, porcine or avian.

The present invention further provides a recombinant raccoonpox virus which comprises a foreign DNA sequence inserted into a non-essential site of the raccoonpox genome, wherein the foreign DNA sequence encodes an antigenic polypeptide derived from a human pathogen and is capable of being expressed in a host infected by the recombinant raccoonpox virus.

Recombinant RPV expressing cytokines is used to enhance the immune response either alone or when combined with vaccines containing cytokines or antigen genes of disease causing microorganisms.

Antigenic polypeptide of a human pathogen which are derived from human herpesvirus include, but are not limited to: hepatitis B virus and hepatitis C virus hepatitis B virus surface and core antigens, hepatitis C virus, human immunodeficiency virus, herpes simplex virus-1, herpes simplex virus-2, human cytomegalovirus, Epstein-Barr virus, Varicella-Zoster virus, human herpesvirus-6, human herpesvirus-7, human influenza, measles virus, hantaan virus, pneumonia virus, rhinovirus, poliovirus, human respiratory syncytial virus, retrovirus, human T-cell leukemia virus, rabies virus, mumps virus, malaria (Plasmodium falciparum), *Bordetella pertussis*, Diphtheria, *Rickettsia prowazekii, Borrelia burgdorferi*, Tetanus toxoid, malignant tumor antigens.

The present invention further provides a recombinant raccoonpox virus which comprises a foreign DNA sequence inserted into a non-essential site of the raccoonpox genome, wherein the foreign DNA sequence encodes a cytokine capable of stimulating an immune in a host infected by the recombinant raccoonpox virus and is capable of being expressed in the host infected.

The antigenic polypeptide of an equine pathogen can derived from equine influenza virus, or equine herpesvirus. In one embodiment the antigenic polypeptide is equine influenza neuraminidase or hemagglutinin. Examples of such antigenic polypeptide are equine influenza virus type A/Alaska 91 neuraminidase, equine influenza virus type A/Prague 56 neuraminidase, equine influenza virus type A/Miami 63 neuraminidase, equine influenza virus type A/Kentucky 81 neuraminidase, equine influenza virus type A/Kentucky 92 neuraminidase equine herpesvirus type 1 glycoprotein B, equine herpesvirus type 1 glycoprotein D, *Streptococcus equi*, equine infectious anemia virus, equine encephalitis virus, equine rhinovirus and equine rotavirus.

The present invention further provides a recombinant raccoonpox virus which comprises a foreign DNA sequence inserted into a non-essential site of the raccoonpox genome, wherein the foreign DNA sequence encodes an antigenic polypeptide derived from bovine respiratory syncytial virus or bovine parainfluenza virus, and is capable of being expressed in a host infected by the recombinant raccoonpox virus.

For example, the antigenic polypeptide of derived from infectious bovine rhinotracheitis virus gE, bovine respiratory syncytial virus equine pathogen can derived from equine influenza virus is bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase.

The present invention further provides a recombinant raccoonpox virus which comprises a foreign DNA sequence inserted into a non-essential site of the raccoonpox genome, wherein the foreign DNA sequence encodes an antigenic polypeptide derived from infectious bovine rhinotracheitis virus and is capable of being expressed in a host infected by the recombinant raccoonpox virus. Examples of such antigenic polypeptide are infectious bovine rhinotracheitis virus glycoprotein E, glycoprotein G, glycoprotein gD and glycoprotein gI.

The present invention further provides a recombinant raccoonpox virus which comprises a foreign DNA sequence inserted into a non-essential site of the raccoonpox genome, wherein the foreign DNA sequence encodes bovine viral diarrhea virus (BVDV) glycoprotein 48 or glycoprotein 53, and wherein the foreign DNA sequence is capable of being expressed in a host infected by the recombinant raccoonpox virus.

The present invention further provides a recombinant raccoonpox virus which comprises a foreign DNA sequence inserted into a non-essential site of the raccoonpox genome, wherein the foreign DNA sequence encodes an antigenic polypeptide derived from infectious bursal disease virus and wherein the foreign DNA sequence is capable of being expressed in a host infected by the recombinant raccoonpox virus. Examples of such antigenic polypeptide are infectious bursal disease virus polyprotein and VP2.

The present invention further provides a recombinant raccoonpox virus in which the foreign DNA sequence encodes an antigenic polypeptide which includes, but is not limited to: MDV gA, MDV gB, MDV gD, NDV HN, NDV F, ILT gB, ILT gI, ILT gD, IBDV VP2, IBDV VP3, IBDV VP4, IBDV polyprotein, IBV spike, IBV matrix, avian encephalomyelitis virus, avian reovirus, avian paramyxovirus, avian influenza virus, avian adenovirus, fowl pox virus, avian coronavirus, avian rotavirus, chick anemia virus, Salmonella spp. *E. coli*, Pasteurella spp., Bordetella spp., Eimeria spp., Histomonas spp., Trichomonas spp., Poultry nematodes, cestodes, trematodes, poultry mites/lice, and poultry protozoa.

This invention is illustrated in the Experimental Detail sections which follow. These sections are set forth to aid in an understanding of the invention but are not intended to, and should not be construed to, limit in any way the invention as set forth in the claims which follow thereafter.

EXPERIMENTAL DETAILS

Preparation of Raccoonpox Virus Stock Samples

Raccoonpox virus (RPV) isolate ATCC VR-838 was used for preparation of raccoonpox virus stock samples and raccoonpox virus genomic DNA. Another RPV isolate available is V71-I-85A from Center for Disease Control (CDC; Atlanta, Ga.). Raccoonpox virus (RPV) samples were prepared by infecting VERO cells, CRFK cells or MDCK cells at a multiplicity of infection of 0.01 PFU/cell in Dulbeccols Modified Eagle's Medium containing 2 mM glutamine, 100 units/ml penicillin, 100 units/ml streptomycin (these components were obtained from Sigma or equivalent supplier, and hereafter are referred to as DMEM negative medium). Prior to infection, the cell monolayers were washed once with DMEM negative medium to remove traces of fetal bovine serum. The RPV contained in the initial inoculum (0.5 ml for 10 cm plate; 10 ml for T225 cm flask) was then allowed to absorb onto the cell monolayer for two hours, being redistributed every half hour. After this period, the original inoculum was brought up to the recommended volume with the addition of complete DMEM medium (DMEM negative medium plus 5% fetal bovine serum). The plates were incubated at 37° C. in 5% $CO_2$ until cytopathic effect was complete. The medium and cells were harvested and frozen in a 50 ml conical screw cap tube at −70° C. Upon thawing at 37° C., the virus stock was aliquoted into 1.0 ml vials and refrozen at −70° C. The titers were usually about $10^5$–$10^6$ PFU/ml.

Preparation of RPV DNA

For raccoonpox virus DNA isolation, a confluent monolayer of VERO cells in a T225 $cm^2$ flask was infected at a multiplicity of 0.1 with raccoonpox virus (ATCC VR-838) and incubated 3–5 days until the cells were showing 100% cytopathic effect. The infected cells were then harvested by scraping the cells into the medium and centrifuging at 3000 rpm for 5 minutes in a clinical centrifuge. The medium was decanted, and the cell pellet was gently resuspended in 1.0 ml Phosphate Buffer Saline (PBS: 1.5 g $Na_2HPO_4$, 0.2 g $KH_2PO_4$, 0.8g NaCl and 0.2 g KCl per liter $H_2O$) (per T175) and subjected to two successive freeze-thaws (−70° C. to 37° C.). Upon the last thaw, the cells (on ice) were sonicated two times for 30 seconds each with 45 seconds cooling time in between. Cellular debris was then removed by centrifuging (Sorvall RC-5B superspeed centrifuge) at 3000 rpm for 5 minutes in a HB4 rotor at 4° C. RPV virions, present in the supernatant, were then pelleted by centrifugation at 15,000 rpm for 20 minutes at 4° C. in a SS34 rotor (Sorvall) and resuspended in 10 mM Tris (pH 7.5). This fraction was then layered onto a 36% sucrose gradient (w/v in 10 mM tris pH 7.5) and centrifuged (Beckman L8-70M Ultracentrifuge) at 18,000 rpm for 60 minutes in a SW41 rotor (Beckman) at 4° C. The virion pellet was resuspended in 1.0 ml of 10 mM tris pH 7.5 and sonicated on ice for 30 seconds. This fraction was layered onto a 20% to 50% continuous sucrose gradient and centrifuged 16,000 rpm for 60 minutes in a SW41 rotor at 4° C. The RPV virion band located about three quarters down the gradient was harvested, diluted with 20% sucrose and pelleted by centrifugation at 18,000 rpm for 60 minutes in a SW41 rotor at 4° C. The resultant pellet was then washed once with 10 mM Tris pH 7.5 to remove traces of sucrose and finally resuspended in 10 mM Tris pH 7.5. RPV DNA was then extracted from the purified virions by lysis (4 hours at 60° C.) induced by the addition of EDTA, SDS, and proteinase K to final concentrations of 20 mM, 0.5% and 0.5 mg/ml, respectively. After digestion, three phenol:chloroform (1:1) extractions were conducted and the sample precipitated by the addition of two volumes of absolute ethanol and incubation at −20° C. for 30 minutes. The sample was then centrifuged in an Eppendorf minifuge for 5 minutes at full speed. The supernatant was decanted, and the pellet air dried and rehydrated in 0.01 M Tris pH 7.5, 1 mM EDTA at 4° C.

Preparation of Infected Cell Lysates

For cell lysate preparation, serum free medium was used. A confluent monolayer of cells (VERO, CRFK, or MDCK) in a 25 cm flask or a 60 mm petri dish was infected with 100 μl of virus sample. After cytopathic effect was complete, the medium and cells were harvested and the cells were pelleted at 3000 rpm for 5 minutes in a clinical centrifuge. The cell pellet was resuspended in 250 μl of disruption buffer (2% sodium dodecyl sulfate, 2% β-mercapto-ethanol). The samples were sonicated for 30 seconds on ice and stored at −20° C.

Western Blotting Procedure

Samples of lysates and protein standards were run on a polyacrylamide gel according to the procedure of Laemnli (19). After gel electrophoresis the proteins were transferred and processed according to Sambrook et al. (1989) (20). The primary antibody was diluted 1:100 with 5% non-fat dry milk in Tris-sodium chloride, and sodium Azide (TSA: 6.61 g Tris-HCl, 0.97 g Tris-base, 9.0 g NaCl and 2.0 g Sodium Azide per liter $H_2O$). The secondary antibody was alkaline phosphatase conjugated and diluted 1:1000 with TSA.

Molecular Biological Techniques

Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Sambrook et al. (1989) and Current Protocols in Molecular Biology (1992). (20,21) Except as noted, these were used with minor variation.

DNA Sequencing

DNA sequencing was performed by fluorescent labeled dideoxy sequencing reactions using ABI PRISM Dye Terminator Cycle Sequencing Ready Reaction Kit with AMPLITAQ DNA polymerase, FS (Perkin-Elmer; per manufacturer's instructions) and electrophoresed on an Perkin-Elmer/Applied Biosystems automated DNA sequencer Model 373A according to manufacturer's instructions. Reactions using both the dGTP mixes and the dITP mixes were performed to clarify areas of compression.

Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using DNAStar software.

Cloning with the Polymerase Chain Reaction

The polymerase chain reaction (PCR) was used to introduce restriction sites convenient for the manipulation of various DNAs. The procedures used are described by Innis, et al. (1990) (22). In general, amplified fragments were less than 500 base pairs in size and critical regions of amplified fragments were confirmed by DNA sequencing. The primers used in each example are detailed in the descriptions of the construction of homology vectors below.

Homologous Recombination Procedure for Generating Recombinant RPV or SPV

This method relies upon the homologous recombination between the raccoonpox virus DNA and the plasmid homology vector DNA which occurs in the tissue culture cells containing both raccoonpox virus DNA or swinepox virus DNA and transfected plasmid homology vector. For homologous recombination to occur, the monolayers of cells (CRFK, MDCK, ESK-4, PK15 or VERO) are infected with S-RPV-000 (ATCC VR-838) or S-SPV-001 at a multiplicity of infection of 0.01 PFU/cell to introduce replicating RPV or SPV (i.e. DNA synthesis) into the cells. The plasmid homology vector DNA is then transfected into these cells according to the INFECTION—TRANSFECTION PROCEDURE. The construction of homology vectors used in this example of the procedure is described below.

Infection—transfection Procedure for RPV or SPV 6 cm plates of cells (CRFK, MDCK, ESK4, or VERO) about 80% confluent were infected with S-RPV-000 or SPV-001 at a multiplicity of infection of 0.01 PFU/cell in DMEM negative medium or ESK negative medium and incubated at 37° C. in a humidified 5% $CO_2$ environment for 2–3 hours. The transfection procedure used is essentially that recommended for LIPOFECTIN Reagent (BRL). Briefly, for each 6 cm plate, 15 μg of plasmid DNA was diluted up to 100 μl with $H_2O$. Separately, 50 micrograms of LIPOFECTIN™ Reagent was diluted to 100 μl with $H_2O$. The 100 μl of diluted LIPOFECTIN™ Reagent was then added dropwise to the diluted plasmid DNA contained in a polystyrene 5 ml snap cap tube and mixed gently. The mixture was then incubated for 15–20 minutes at room temperature. During this time, the virus inoculum was removed from the 6 cm plates and the cell monolayers washed once with either DMEM or ESK negative medium. Five ml of DMEM negative medium or ESK negative medium was then added to the plasmid DNA/LIPOFECTIN™ mixture and the contents pipetted onto the cell monolayer. The cells were incubated overnight (about 16 hours) at 37° C. in a humidified 5% $CO_2$ environment. The next day the 5 ml of DMEM negative medium was removed and replaced with 5 ml DMEM complete medium. The cells were incubated at 37° C. in 5% $CO_2$ for 3–5 days until cytopathic effect from the virus was 80–100%. Virus was harvested as described above for the preparation of virus stocks. This stock was referred to as a transfection stock and was subsequently screened for recombinant virus by the BLUOGAL™ SCREEN FOR RECOMBINANT RACCOONPOX VIRUS OR CPRG SCREEN FOR RECOMBINANT RACCOONPOX VIRUS.

Screen for Recombinant RPV or SPV Expressing β-galactosidase BLUOGAL™ and CPRG assays) or β-glucuronidase (X-GLUC™ assay)

When the *E. coli* β-galactosidase (lacZ) marker gene was incorporated into a recombinant virus the plaques containing the recombinants were visualized by one of two simple methods. In the first method, the chemical BLUOGAL™ (Life Sciences Technology, Bethesda, Md.) was incorporated (200 μg/ml) into the agarose overlay during the plaque assay, and plaques expressing active β-galactosidase turned blue. The blue plaques were then picked onto fresh cells (MDCK, ESK4, CRFK or VERO) and purified by further blue plaque isolation. In the second method, CPRG (Boehringer Mannheim) was incorporated (400 μg/ml) into the agarose overlay during the plaque assay, and plaques expressing active β-galactosidase turned red. The red plaques were then picked onto fresh cells (MDCK, ESK4 CRFK or VERO) and purified by further red plaque isolation. In both cases viruses were typically purified with three to four rounds of plaque purification.

When the *E. coli* β-glucuronidase (uidA) marker gene was incorporated into a recombinant virus the plaques containing the recombinants were visualized by using the chromogenic substrate, X-beta-D-gluUA CHX (X-GLUC™; 5-Bromo-4-chloro-3-indoxyl-beta-D-glucuronic acid, cyclohexylammonium salt; Biosynth AG; Switzerland) was incorporated (200 μg/ml) into the agarose overlay during the plaque assay, and plaques expressing active β-glucuronidase turned blue. The blue plaques were then picked onto fresh cells (MDCK, ESK4 CRFK or VERO) and purified by further blue plaque isolation.

Screen for Foreign Gene Expression in Recombinant RPV using Black Plaque Assays

Figure 5:
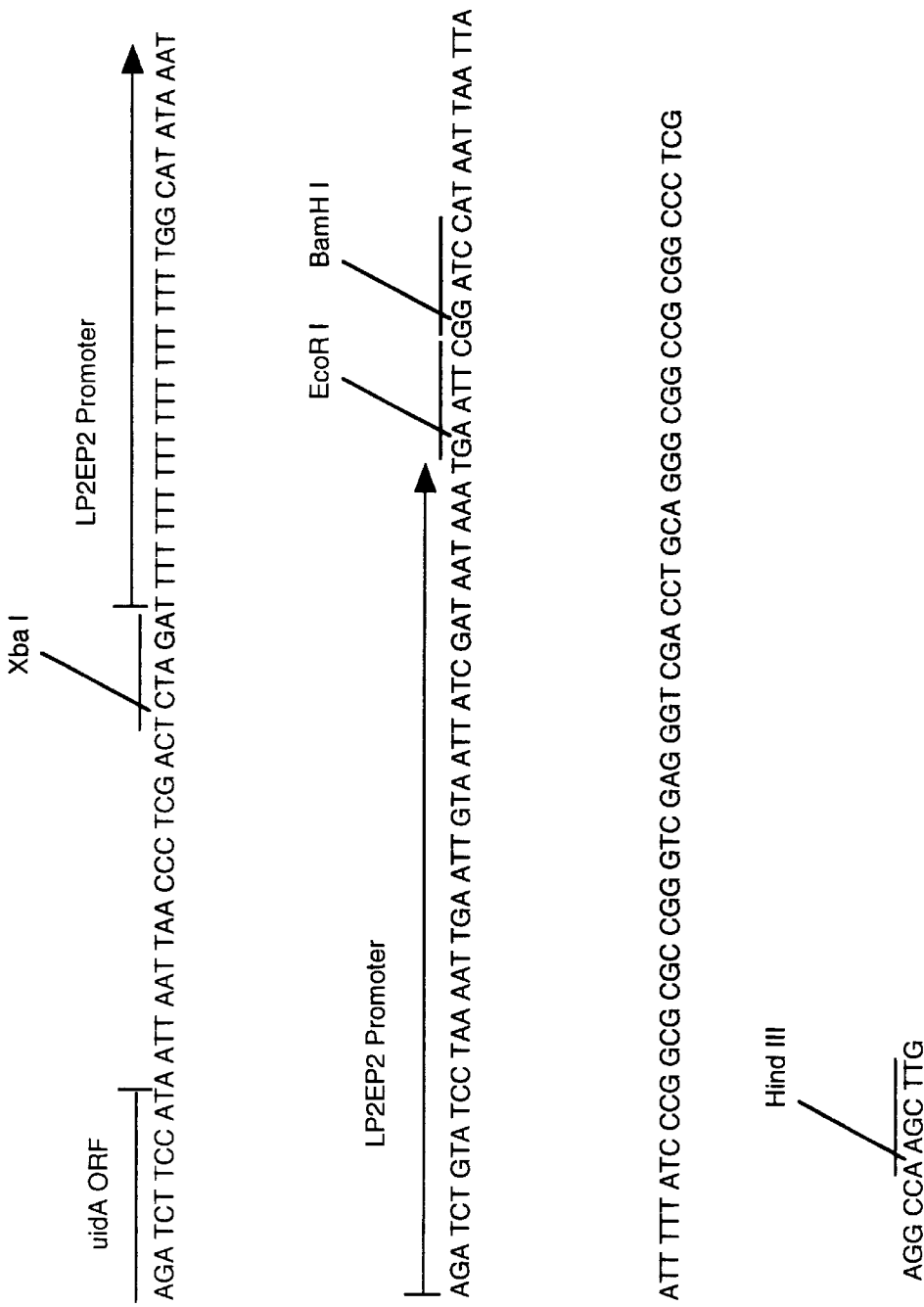
FIG. 5: DNA sequence of the synthetic pox viral promoter LP2EP2 and position of unique EcoRI and BamHI sites (SEQ ID NO. 28) for insertion of foreign DNA under the control of the LP2EP2 promoter in homology vector 919-16.12. The calorimetric marker for positive selection of recombinant raccoonpox virus is the E. coli uidA gene. Recombinant raccoonpox virus, S-RPV-011, was constructed to contain this DNA sequence.
Figure 6:
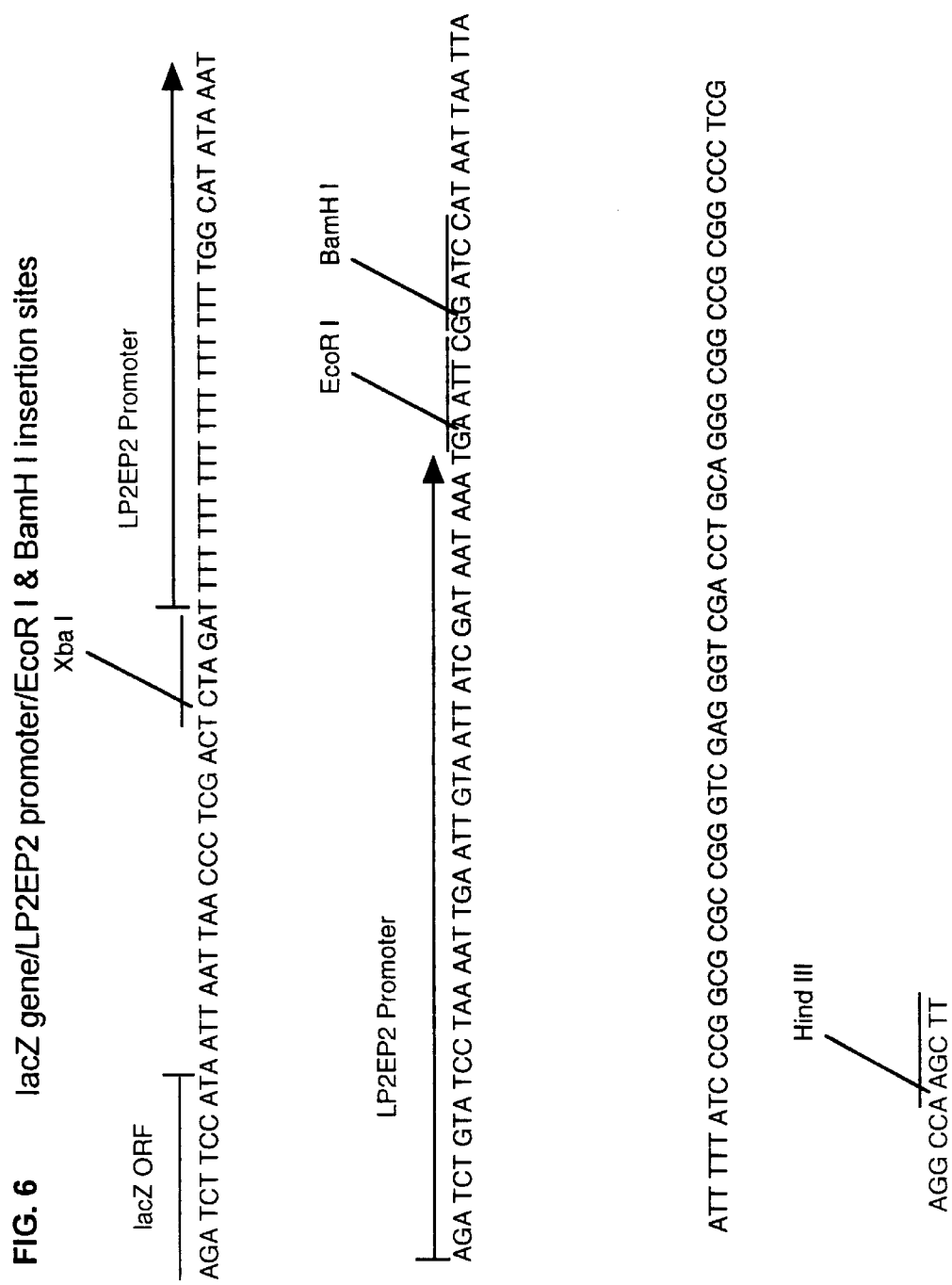
FIG. 6: DNA sequence of the synthetic pox viral promoter LP2EP2 and position of unique EcoRI and BamHI sites (SEQ ID NO. 29) for insertion of foreign DNA under the control of the LP2EP2 promoter in homology vector 902-49.46, 902-67.1, 902-67.14, and 902-67.27. The colorimetric marker for positive selection of recombinant raccoonpox virus is the E. coli lacZ gene. Recombinant raccoonpox viruses, S-RPV-007, S-RPV-008, S-RPV-009, S-RPV-010, was constructed to contain this DNA sequence in different insertion regions of the recombinant raccoonpox virus.

To analyze expression of foreign antigens expressed by recombinant raccoonpox viruses, monolayers of cells (MDCK, CRFK or VERO) were infected with recombinant RPV, overlayed with nutrient agarose media and incubated for 3–5 days at 37° C. for plaque development to occur. The agarose overlay was then removed from the dish, the cells fixed with 100% methanol for 10 minutes at room temperature and the cells air dried. Fixation of the cells results in cytoplasmic antigen as well as surface antigen detection whereas specific surface antigen expression can be detected using non-fixed cells. The primary antibody was then diluted to the appropriate dilution with 1×blotto (5% non-fat dry milk in Tris-sodium chloride, and sodium Azide (TSA: 6.61 g Tris-HCl, 0.97 g Tris-base, 9.0 g NaCl and 2.0 g Sodium Azide per liter $H_2O$) and incubated on the cell monolayer for 2 hours at room temperature. Unbound antibody was then removed by washing the cells three times with TS buffer at room temperature. The secondary antibody, a alkaline-phosphatase conjugate, was diluted 1:1000 with 1×blotto and incubated with the cells for 2 hours at room temperature. Unbound secondary antibody was then removed by washing the cells three times with TS buffer (6.61 g Tris-HCl, 0.97 g Tris-base, 9.0 g NaCl per liter $H_2O$) at room temperature. The cells were then incubated 15–30 minutes at room temperature with freshly prepared substrate solution (100 mM Tris HCl pH. 9.5, 100 mM NaCl, 5 mM $MgCl_2$, 0.3 mg/ml Nitro Blue Tetrazolium and 0.15 mg/ml 5-Bromo-4-chloro-3-Indoyl Phosphatas). Plaques expressing the correct antigen stain black. A fixer solution (20 mM Tris-HCl pH 2.9 and 1 mM EDTA) was used to stop the color development reaction.

Procedure for Purification of Viral Glycoproteins for use as Diagnostics

Viral glycoproteins are purified using antibody affinity columns. To produce monoclonal antibodies, 8 to 10 week old BALB/c female mice are vaccinated intraperitoneally seven times at two to four week intervals with $10^7$ PFU of raccoonpox virus recombinants. Three weeks after the last vaccination, mice are injected intraperitoneally with 40 mg of the corresponding viral glycoprotein. Spleens are removed from the mice three days after the last antigen dose.

Splenocytes are fused with mouse NS1/Ag4 plasmacytoma cells by the procedure modified from Oi and Herzenberg, (23). Splenocytes and plasmacytoma cells are pelleted together by centrifugation at 300×g for 10 minutes. One ml of a 50% solution of polyethylene glycol (m.w. 1300–1600) is added to the cell pellet with stirring over one minute. Dulbecco's modified Eagles's medium (5 ml) is added to the cells over three minutes. Cells are pelleted by centrifugation at 300×g for 10 minutes and resuspended in medium with 10% fetal bovine serum and containing 100 mM hypoxanthine, 0.4 mM aminopterin and 16 mM thymidine (HAT). Cells (100 ml) are added to the wells of eight to ten 96-well tissue culture plates containing 100 ml of normal spleen feeder layer cells and incubated at 37° C. Cells are fed with fresh HAT medium every three to four days.

Hybridoma culture supernatants are tested by the ELISA ASSAY in 96-well microtiter plates coated with 100 ng of viral glycoprotein. Supernatants from reactive hybridomas are further analyzed by black-plaque assay and by Western Blot. Selected hybridomas are cloned twice by limiting dilution. Ascetic fluid is produced by intraperitoneal injection of $5\times10^6$ hybridoma cells into pristane-treated BALB/c mice.

Cell lysates from raccoonpox virus recombinants are obtained as described in PREPARATION OF INFECTED CELL LYSATES. The glycoprotein-containing cell lysates (100 mls) are passed through a 2-ml agarose affinity resin to which 20 mg of glycoprotein monoclonal antibody has been immobilized according to manufacturer's instructions (AFC Medium, New Brunswick Scientific, Edison, N.J.). The column is washed with 100 ml of 0.1% Nonidet P-40 in phosphate-buffered saline (PBS) to remove nonspecifically bound material. Bound glycoprotein is eluted with 100 mM carbonate buffer, pH 10.6 (24). Pre- and posteluted fractions are monitored for purity by reactivity to the RPV monoclonal antibodies in an ELISA system.

Elisa Assay

A standard enzyme-linked immunosorbent assay (ELISA) protocol is used to determine the immune status of cattle following vaccination and challenge.

A glycoprotein antigen solution (100 ml at ng/ml in PBS) is allowed to absorb to the wells of microtiter dishes for 18 hours at 4° C. The coated wells are rinsed one time with PBS. Wells are blocked by adding 250 ml of PBS containing 1% BSA (Sigma) and incubating 1 hour at 37° C. The blocked wells are rinsed one time with PBS containing 0.02% Tween 20. 50 ml of test serum (previously diluted 1:2 in PBS containing 1% BSA) are added to the wells and incubated 1 hour at 37° C. The antiserum is removed and the wells are washed 3 times with PBS containing 0.02% Tween 20. 50 ml of a solution containing anti-bovine IgG coupled to horseradish peroxidase (diluted 1:500 in PBS containing 1% BSA, Kirkegaard and Perry Laboratories, Inc.) is added to visualize the wells containing antibody against the specific antigen. The solution is incubated 1 hour at 37° C., then removed and the wells are washed 3 times with PBS containing 0.02% Tween 20. 100 ml of substrate solution (ATBS, Kirkegaard and Perry Laboratories, Inc.) are added to each well and color is allowed to develop for 15 minutes. The reaction is terminated by addition of 0.1M oxalic acid. The color is read at absorbance 410 nm on an automatic plate reader.

Strategy for the Construction of Synthetic Pox Viral Promoters

For recombinant swinepox vectors synthetic pox promoters offer several advantages including the ability to control the strength and timing of foreign gene expression. Three promoter cassettes LP1, EP1 and LP2 based on promoters that have been defined in the vaccinia virus (1, 7 and 8) were designed. Each cassette was designed to contain the DNA sequences defined in vaccinia flanked by restriction sites which could be used to combine the cassettes in any order or combination. Initiator methionines were also designed into each cassette such that inframe fusions could be made at either EcoRI or BamHI sites. A set of translational stop codons in all three reading frames and an early transcriptional termination signal were also engineered downstream of the inframe fusion site. DNA encoding each cassette was synthesized according to standard techniques and cloned into the appropriate homology vectors (see FIGS. 5, 6, and 7).

Procedure for Production of Murine Polyclonal Antibodies to Proteins Expressed in Recombinant Raccoonpox Virus Three groups of five mice each were vaccinated subcutaneously in the rear leg with 200 ul of a 1:1 mixture of infected cell lysate and Freunds complete adjuvant (S-RPV-003 (SIV NA), S-RPV-004 (PRRS ORF3) and S-RPV-005 (PRRS ORF4)). The infected cell lysates were prepared by harvesting a T225 flask Vero cells at 90%+CPE. The infected cell pellets were washed once in PBS and finally resuspended in 1 ml of PBS. The 1 ml lysate was frozen at −70° C. and thawed on ice. The 1 ml lysate was sonicated one time (lowest setting). The mice received two additional doses of cell lysates mixed with Freunds incomplete adjuvant at 3 weeks post vaccination and 6 weeks post vaccination. The mice were sacrificed at 8 weeks post vaccination. About 2 ml of serum was obtained from 5 mice. The serum was tested for SIV or PRRS specific antibodies by BLACK PLAQUE ASSAY.

Plasmid 880-96.43

The plasmid 880-96.43 was constructed for the purpose of inserting foreign DNA into raccoonpox virus. It comprises the approximately 2055 base pair HindIII U genomic fragment of raccoonpox virus (SEQ ID NO. 1). Two open reading frames within the HindIII U fragment are the vaccinia virus homologs (17) of the O1L ORF (SEQ ID NO. 2) and the E11L ORF (SEQ ID NO. 3). The O1L ORF and E11L ORF are non-essential and foreign DNA is inserted within these ORFs or in the intergenic region between the ORFs. Any restriction site within this region is useful as an insertion site for foreign DNA. A restriction enzyme site within this region which is not unique is altered by insertion of a DNA linker which converts the site to a unique restriction enzyme recognition sequence. Preferably the restriction enzyme site used for insertion of foreign DNA is an XbaI site at approximately nucleotide 1065 within the 2055 base pair HindIII U genomic fragment (SEQ ID NO. 1). The insertion site is within the O1L ORF between amino acids 459 and 460 of the open reading frame. The plasmid vector was derived from an approximately 2999 base pair HindIII restriction fragment of pSP64 (PROMEGA™). Fragment 1 is an approximately 2055 base pair HindIII U genomic fragment of raccoonpox virus (6) (SEQ ID NO. 1). Plasmid 880-96.43 was used to make homology vectors for insertion of foreign DNA in recombinant raccoonpox virus.

Plasmid 902-15.2

The plasmid 902-15.2 was constructed for the purpose of inserting foreign DNA into raccoonpox virus. It comprises the approximately 1801 base pair subfragment (SEQ ID NO. 4) of the HindIII U genomic fragment of raccoonpox virus. Two open reading frames within the HindIII U fragment are the vaccinia virus homologs (17) of the O1L ORF (SEQ ID NO. 2) and the E11L ORF (SEQ ID NO. 3). The O1L ORF and E11L ORF are non-essential and foreign DNA is inserted within these ORFs or in the intergenic region between the ORFs. Any restriction site within this region is useful as an insertion site for foreign DNA. The plasmid vector was derived from an approximately 2999 base pair HindIII restriction fragment of pSP64 (PROMEGA™). Fragment 1 is an approximately 1801 base pair HindIII subfragment of the HindIII U genomic fragment (6) synthesized by POLYMERASE CHAIN REACTION using plasmid 880-96.43 as a template. The primer upstream of the O1L and E1L ORFs was 5-CCG AAGCTTCCGTGCTCCATCTATATAATATATTAAAC-3' (SEQ ID NO 14; 2/97.6). The primer downstream of the O1L and E11L ORFs was 5'-GAAT AAGCTTCCCGTTACTTTAGTAAAATCTTTTACAAA-3' (SEQ ID NO 15; 2/97.7). A unique NotI synthetic linker was inserted within an XbaI site (Nucleotides 1098 to 1113; a unique NotI site is at nucleotide 1105; SEQ ID NO. 4)

The restriction enzyme site used for insertion of foreign DNA is an XbaI site at approximately nucleotide 1065 within the 2055 base pair HindIII U genomic fragment (SEQ ID NO. 1). The insertion site is within the O1L ORF between amino acids 459 and 460 of the open reading frame. Plasmid 902-15.2 was used to make homology vectors for insertion of foreign DNA in recombinant raccoonpox virus.

Homology Vector 902-16.2

The plasmid 902-16.2 was constructed for the purpose of inserting foreign DNA into recombinant raccoonpox virus (RPV). It incorporates an *E. coli* β-galactosidase (lacZ) marker gene and a swine influenza virus (SIV) HA (H1N1) gene flanked by RPV DNA. Upstream of the foreign gene is an approximately 906 base pair fragment of RPV DNA. Downstream of the foreign genes is an approximately 895 base pair fragment of RPV DNA. Direction of transcription of the SIV HA gene is opposite the direction of transcription of the lacZ gene and opposite to the direction of transcription of the RPV O1L ORF. When the plasmid is used according to the HOMOLOGOUS RECOMBINATION PROCEDURE FOR GENERATING RECOMBINANT RPV, a virus containing DNA coding for the foreign genes will result. Note that the β-galactosidase (lacZ) marker gene is under the control of a late promoter (LP1) and the SIV HA (H1N1) gene is under the control of the late/early promoter (LP2EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PRONEGA™). Fragment 1 is an approximately 906 base pair HindIII to XbaI restriction sub-fragment of the RPV HindIII restriction fragment U (6). Fragment 2 is an approximately 1721 base pair BamHI to BamHI restriction fragment synthesized by reverse transcription and polymerase chain reaction (PCR) using genomic RNA from the SIV H1N1 strain (NVSL) To synthesize SIV HA (H1N1, the primer 5'-CCGAGGATCCGGCAATACTATTAGTCTTGCTATG TACATT-3'; 6/95.5) (SEQ ID NO 16) synthesized from the 5' end of the SIV HA (H1N1) gene, introduced an BamHI site at the 5' end of the gene. The primer (5'-CTCTG GGATCCTAATTTAAATACATATTCTGCACTGTA-3'; 6/95.6) (SEQ ID NO 17) was used for reverse transcription and PCR and synthesized from the 3' end of the SIV HA (H1N1) gene and introduced a BamHI site at the 3' end of the gene. The PCR product was digested with BamHI to yield a fragment approximately 1721 base pairs in length corresponding to the SIV HA (H1N1) gene. Fragment 3 is an approximately 3010 base pair BamHI to PvuII restriction fragment of plasmid pJF751 (11) . Fragment 4 is an approximately 895 base pair XbaI to HindIII subfragment of the RPV HindIII fragment U (6). The XbaI sites in fragments 1 and 4 were converted to unique NotI sites using NotI linkers.

Homology Vector 902-19.18

The plasmid 902-19.18 was constructed for the purpose of inserting foreign DNA into recombinant raccoonpox virus (RPV). It incorporates an E. coli β-galactosidase (lacZ) marker gene and a swine influenza virus (SIV) hemagglutinin (HA) (H1N1) gene flanked by RPV DNA. Upstream of the foreign gene is an approximately 906 base pair fragment of RPV DNA. Downstream of the foreign genes is an approximately 895 base pair fragment of RPV DNA. In contrast to homology vector 902-16.2 direction of transcription of the SIV HA gene is the same as the direction of transcription of the lacZ gene and the same as the direction of transcription of the RPV O1L ORF. When the plasmid is used according to the HOMOLOGOUS RECOMBINATION PROCEDURE FOR GENERATING RECOMBINANT RPV, a virus containing DNA coding for the foreign genes will result. Note that the β-galactosidase (lacZ) marker gene is under the control of a late promoter (LP1) and the SIV HA (H1N1) gene is under the control of the late/early promoter (LP2EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an approximately 1721 base pair BamHI to BamHI restriction fragment synthesized by reverse transcription and polymerase chain reaction (PCR) using genomic RNA from the SIV H1N1 strain (NVSL) To synthesize SIV HA (H1N1), the primer 5'-CCGA GGATCCGGCAATACTATTAGTCTTGCTATGTACAT-3'; 6/95.5) (SEQ ID NO 18) synthesized from the 5' end of the SIV HA (H1N1) gene, introduced an BamHI site at the 5' end of the gene. The primer (5'-CTCT GGATCCTAATTTAAATACATATTCTGCACTGTA-3'; 6/95.6) (SEQ ID NO 19) was used for reverse transcription and PCR and synthesized from the 3' end of the SIV HA (H1N1) gene and introduced a BamHI site at the 3' end of the gene. The PCR product was digested with BamHI to yield a fragment approximately 1721 base pairs in length corresponding to the SIV HA (H1N1) gene. Fragment 3 is an approximately 3010 base pair BamHI to PvuII restriction fragment of plasmid pJF751 (11). Fragment 4 is an approximately 895 base pair XbaI to HindIII subfragment of the RPV HindIII fragment U (6). The XbaI sites in fragments 1 and 4 were converted to unique NotI sites using NotI linkers.

Homology Vector 902-49.5

The plasmid 902-49.5 was constructed for the purpose of inserting foreign DNA into recombinant raccoonpox virus (RPV). It incorporates an E. coli β-galactosidase (lacZ) marker gene and a swine influenza virus (SIV) neuraminidase (NA) (H1N1) gene flanked by RPV DNA. Upstream of the foreign gene is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-galactosidase (lacZ) marker gene is under the control of a late promoter (LP1) and the SIV NA (H1N1) gene is under the control of the late/early promoter (LP2EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an approximately 1414 base pair EcoRI to BglII restriction fragment synthesized by reverse transcription and polymerase chain reaction (PCR) using genomic RNA from the SIV H1N1 strain (NVSL) To synthesize SIV NA (H1N) the primer 5'-AAT GAATTCAAAAAATAATAACCATTGGGTCAAT-3'; 6/95.11) (SEQ ID NO 20) synthesized from the 5' end of the SIV NA (H1N1) gene, introduced an EcoRI site at the 5' end of the gene. The primer (5'-GGAAGATCTACTTGTCAATGGTGAATGGCAGAT CAG-31; 6/95.12) (SEQ ID NO 21) was used for reverse transcription and PCR and synthesized from the 3' end of the SIV NA (H1N1) gene and introduced a BglII site at the 3' end of the gene. The PCR product was digested with EcoRI and BglII to yield a fragment approximately 1414 base pairs in length corresponding to the SIV NA (H1N1) gene. Fragment 3 is an approximately 3010 base pair BamHI to PvuII restriction fragment of plasmid pJF751 (25). Fragment 4 is an approximately 895 base pair XbaI to HindIII subfragment of the RPV HindIII fragment U. The XbaI sites in fragments 1 and 4 were converted to unique NotI sites using NotI linkers.

Homology Vector 902-49.14

The plasmid 902-49.14 was constructed for the purpose of inserting foreign DNA into recombinant raccoonpox virus (RPV). It incorporates an E. coli β-galactosidase (lacZ) marker gene and a porcine reproductive and respiratory syndrome virus (PRRS) ORF3 gene flanked by RPV DNA. Upstream of the foreign gene is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-galactosidase (lacZ) marker gene is under the control of a late promoter (LP1) and the PRRS ORF3 gene is under the control of the late/early promoter (LP2EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an EcoRI to BamHI restriction fragment synthesized by reverse transcription and polymerase chain reaction (PCR) using genomic RNA from a U.S. Isolate of PRRS obtained from the NVSL (Reference strain, IA-2). To synthesize PRRS ORF3, the primer 5'-TTC GAATTCGGCTAATAGCTGTACATTCCTCCATATTT-3'; 1/96.7) (SEQ ID NO 22) synthesized from the 5' end of the PRRS ORF3 gene, introduced an EcoRI site at the 5' end of the gene. The primer (5'-GG GGATCCTATCGCCGTACGGCACTGAGGG-3'; 1/96.8) (SEQ ID NO 23) was used for reverse transcription and PCR and synthesized from the 3' end of the PRRS ORF3 gene. The PCR product was digested with EcoRI and BamHI to yield a fragment approximately 768 base pairs in length corresponding to the PRRS ORF3 gene. Fragment 3 is an approximately 3010 base pair BamHI to PvuII restriction fragment of plasmid pJF751 (25). Fragment 4 is an approximately 895 base pair XbaI to HindIII subfragment of the RPV HindIII fragment U. The XbaI sites in fragments 1 and 4 were converted to unique NotI sites using NotI linkers.

Homology Vector 902-49.23

The plasmid 902-49.23 was constructed for the purpose of inserting foreign DNA into recombinant raccoonpox virus (RPV). It incorporates an *E. coli* β-galactosidase (lacZ) marker gene and a porcine reproductive and respiratory syndrome virus (PRRS) ORF4 gene flanked by RPV DNA. Upstream of the foreign gene is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-galactosidase (lacZ) marker gene is under the control of a late promoter (LP1) and the PRRS ORF4 gene is under the control of the late/early promoter (LP2EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an EcoRI to BamHI restriction fragment synthesized by reverse transcription and polymerase chain reaction (PCR) using genomic RNA from a U.S. Isolate of PRRS obtained from the NVSL (Reference strain, IA-2). To synthesize PRRS ORF4, the primer (5'-CC GAATTCGGCTGCGTCCCTTCTTTTCCTCATGG-3'; 1/96.11) (SEQ ID NO 24) synthesized from the 5' end of the PRRS ORF4 gene, introduced an EcoRI site at the 5' end of the gene. The primer (5µ'CT GGATCCTTCAAATTGCCAACAGAATGGCAAAAA GAC-3'; 1/96.12) (SEQ ID NO 25) was used for reverse transcription and PCR and synthesized from the 3' end of the PRRS ORF4 gene. The PCR product was digested with EcoRI and BamHI to yield a fragment approximately 542 base pairs in length corresponding to the PRRS ORF4 gene. Fragment 3 is an approximately 3010 base pair BamHI to PvuII restriction fragment of plasmid pJF751 (25). Fragment 4 is an approximately 895 base pair XbaI to HindIII sub-fragment of the RPV HindIII fragment U. The XbaI sites in fragments 1 and 4 were converted to unique NotI sites using NotI linkers.

Homology Vector 902-49.34

The plasmid 902-49.34 was constructed for the purpose of inserting foreign DNA into RPV. It incorporates an *E. coli* β-galactosidase (lacZ) marker gene and a porcine reproductive and respiratory syndrome virus (PRRS) ORF5 gene flanked by RPV DNA. Upstream of the foreign gene is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-galactosidase (lacZ) marker gene is under the control of a late promoter (LP1) and the PRRS ORF5 gene is under the control of the late/early promoter (LP2EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an EcoRI to BamHI restriction fragment synthesized by reverse transcription and polymerase chain reaction (PCR) using genomic RNA from a U.S. Isolate of PRRS obtained from the NVSL (Reference strain, IA-2). To synthesize PRRS ORF5, the primer (5'-TT GAATTCGTTGGAGAAATGCTTGACCGCGGGC-3'; 1/96.13) (SEQ ID NO 26) synthesized from the 5' end of the PRRS ORF5 gene, introduced an EcoRI site at the 5' end of the gene. The primer (5'-GAA GGATCCTAAGGACGACCCCATTGTTCCGCTG-3'; 1/96.14) (SEQ ID NO 27) was used for reverse transcription and PCR and synthesized from the 3' end of the PRRS ORF5 gene. The PCR product was digested with EcoRI and BamHI to yield a fragment approximately 606 base pairs in length corresponding to the PRRS ORF5 gene. Fragment 3 is an approximately 3010 base pair BamHI to PvuII restriction fragment of plasmid pJF751 (25). Fragment 4 is an approximately 895 base pair XbaI to HindIII subfragment of the RPV HindIII fragment U. The XbaI sites in fragments 1 and 4 were converted to unique NotI sites using NotI linkers.

Homology Vector 902-49.46

The plasmid 902-49.46 was constructed for the purpose of inserting foreign DNA into RPV. It incorporates an *E. coli* β-galactosidase (lacZ) marker gene flanked by RPV DNA. Upstream of the foreign gene is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-galactosidase (lacZ) marker gene is under the control of a late promoter (LP1) and a second foreign DNA is inserted into an EcoRI or BamHI site, and the second foreign DNA is under the control of the late/early promoter (LP2EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an approximately 3010 base pair BamHI to PvuII restriction fragment of plasmid pJF751 (25). Fragment 3 is an approximately 895 base pair XbaI to HindIII subfragment of the RPV HindIII fragment U. The XbaI sites in fragments 1 and 3 were converted to unique NotI sites using NotI linkers. Synthetic DNA between fragments 2 and 3 contains the LP2EP2 promoter and an EcoRI site and a BamHI site for insertion of foreign DNA. (See FIG. 6).

Homology Vector 902-67.1

The plasmid 902-67.1 was constructed for the purpose of inserting foreign DNA into RPV. It incorporates an *E. coli* β-galactosidase (lacZ) marker gene flanked by RPV DNA. Upstream of the foreign gene is an approximately 1500 base pair fragment of RPV DNA. Downstream of the foreign genes is an approximately 3600 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-galactosidase (lacZ) marker gene is under the control of a late promoter (LP1) and a second foreign DNA is inserted into an EcoRI or BamHI site, and the second foreign DNA is under the control of the late/early promoter (LP2EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 2200 base pair HindIII to SnaBI restriction sub-fragment of the RPV HindIII restriction fragment N (6). Fragment 2 is an approximately 3010 base pair BamHI to PvuII restriction fragment of plasmid pJF751 (25). Fragment 3 is an approximately 2900 base pair SnaBI to HindIII subfragment of the RPV HindIII fragment N. The SnaB I sites in fragments 1 and 3 were converted to unique NotI sites using NotI linkers. Synthetic DNA between fragments 2 and 3 contains the LP2EP2 promoter and an EcoRI site and a BamHI site for insertion of foreign DNA. (See FIG. 6).

Homology Vector 902-67.14

The plasmid 902-67.14 was constructed for the purpose of inserting foreign DNA into RPV. It incorporates an *E. coli* β-galactosidase (lacZ) marker gene flanked by RPV DNA. Upstream of the foreign gene is an approximately 1500 base pair fragment of RPV DNA. Downstream of the foreign genes is an approximately 3600 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-galactosidase (lacZ) marker gene is under the control of a late promoter (LP1) and a second foreign DNA is inserted into an EcoRI or BamHI site, and the second foreign DNA is under the control of the late/early promoter (LP2EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 1500 base pair HindIII to EcoRV restriction sub-fragment of the RPV HindIII restriction fragment N (6). Fragment 2 is an approximately 3010 base pair BamHI to PvuII restriction fragment of plasmid pJF751 (25). Fragment 3 is an approximately 3600 base pair EcoRV to HindIII subfragment of the RPV HindIII fragment N. The EcoRV sites in fragments 1 and 3 were converted to unique NotI sites using NotI linkers. Synthetic DNA between fragments 2 and 3 contains the LP2EP2 promoter and an EcoRI site and a BamHI site for insertion of foreign DNA. (See FIG. 6).

Homology Vector 902-67.27

The plasmid 902-67.27 was constructed for the purpose of inserting foreign DNA into RPV. It incorporates an *E. coli* β-galactosidase (lacZ) marker gene flanked by RPV DNA. Upstream of the foreign gene is an approximately 2200 base pair fragment of RPV DNA. Downstream of the foreign genes is an approximately 2900 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-galactosidase (lacZ) marker gene is under the control of a late promoter (LP1) and a second foreign DNA is inserted into an EcoRI or BamHI site, and the second foreign DNA is under the control of the late/early promoter (LP2EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 2200 base pair HindIII to EcoRV restriction sub-fragment of the RPV HindIII restriction fragment N (6). Fragment 2 is an approximately 3010 base pair BamHI to PvuII restriction fragment of plasmid pJF751 (25). Fragment 3 is an approximately 2900 base pair EcoRV to HindIII subfragment of the RPV HindIII fragment N. The EcoRV sites in fragments 1 and 3 were converted to unique NotI sites using NotI linkers. Synthetic DNA between fragments 2 and 3 contains the LP2EP2 promoter and an EcoRI site and a BamHI site for insertion of foreign DNA. (See FIG. 6).

Homology Vector 919-16.12

The plasmid 919-16.12 was constructed for the purpose of inserting foreign DNA into RPV. It incorporates an *E. coli* β-glucuronidase (uidA) marker gene flanked by RPV DNA. Upstream of the foreign gene is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-glucuronidase (uidA) marker gene is under the control of a late promoter (LP1) and a second foreign DNA is inserted into an EcoRI or BamHI site, and the foreign DNA is under the control of the late/early promoter (LP2EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an approximately 1823 base pair NotI restriction fragment of plasmid pRAJ260 (CLONETECH™). Fragment 3 is an approximately 895 base pair XbaI to HindIII subfragment of the RPV HindIII fragment U. The XbaI sites in fragments 1 and 3 were converted to unique NotI sites using NotI linkers. Synthetic DNA between fragments 2 and 3 contains the LP2EP2 promoter and an EcoRI site and a BamHI site for insertion of foreign DNA. (See FIG. 5).

Homology Vector 919-63.21

The plasmid 919-63.21 was constructed for the purpose of inserting foreign DNA into RPV. It incorporates an *E. coli* β-galactosidase (lacZ) marker gene and a porcine parvovirus (PPV) VP2 capsid protein gene flanked by RPV DNA. Upstream of the foreign gene is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-galactosidase (lacZ) marker gene is under the control of a late promoter (LP1) and the PPV VP2 gene is under the control of the late/early promoter (LP2EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is a BamHI restriction fragment synthesized by reverse transcription and polymerase chain reaction (PCR) using genomic RNA from a U.S. Isolate of PPV obtained from the NADL (Strain NADL-2; non-pathogenic vaccine strain). To synthesize PPV VP2, the primer (5'-CTAA GGATCCGAGTGAAAATGTGGAACAACACAACCC-3'; 4/97.50) (SEQ ID NO 31) synthesized from the 5' end of the PPV VP2 gene, introduced an BamHI site at the 5' end of the gene. The primer (5'-GT GGATCCTAGTATAATTTTCTTGGTATAAGTTGT GAA-3'; 4/97.51) (SEQ ID NO 32) was used for reverse transcription and PCR and synthesized from the 3' end of the PPV VP2 gene. The PCR product was digested with BamHI to yield a fragment approximately 1700 base pairs in length corresponding to the PPV VP2 gene. Fragment 3 is an approximately 3010 base pair BamHI to PvuII restriction fragment of plasmid pJF751 (25). Fragment 4 is an approximately 895 base pair XbaI to HindIII subfragment of the RPV HindIII fragment U. The XbaI sites in fragments 1 and 4 were converted to unique NotI sites using NotI linkers.

Homology Vector 934-64.2

The plasmid 934-64.2 was constructed for the purpose of inserting foreign DNA into RPV. It incorporates an *E. coli* β-glucuronidase (uidA) marker gene and the gene for porcine reproductive and respiratory syndrome virus (PRRS) ORF3 (Eichelberger strain) flanked by RPV DNA. Upstream of the foreign genes is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-glucuronidase (uidA) marker gene is under the control of a late promoter (LP1) and the PRRS ORF3 is inserted into an EcoRI and BamHI site, and is under the control of the early promoter (EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an approximately 1823 base pair NotI restriction fragment of plasmid pRAJ260 (CLONETECH™). Fragment 3 is an EcoRI restriction fragment synthesized by reverse transcription and polymerase chain reaction (PCR) using genomic RNA from a U.S. isolate of PRRS obtained from the Eichelberger atypical strain. To synthesize PRRS ORF3, the primer 5'-CAAT GAATTCTAGCTGTGCACTCCTCCATATTTTCCTC-3'; 9/97.9) (SEQ ID NO 45) synthesized from the 5' end of the PRRS ORF3 gene, introduced an EcoRI site at the 5' end of the gene. The primer (5'-CGG GAATTCCTATCGCCGTACGGCACTGAGG-3'; 9/97.10) (SEQ ID NO 46) was used for reverse transcription and PCR and synthesized from the 3' end of the PRRS ORF3 gene, introduced an EcoRI site at the 3' end of the gene. The PCR product was digested with EcoRI and BamHI to yield a fragment approximately 768 base pairs in length corresponding to the PRRS ORF3 gene.

Fragment 4 is an approximately 895 base pair XbaI to HindIII subfragment of the RPV HindIII fragment U. The XbaI sites in fragments 1 and 3 were converted to unique NotI sites using NotI linkers.

Homology Vector 934-65.1

The plasmid 934-65.1 was constructed for the purpose of inserting foreign DNA into RPV. It incorporates an *E. coli* β-glucuronidase (uidA) marker gene and the gene for porcine reproductive and respiratory syndrome virus (PRRS) ORF2 (Eichelberger strain) flanked by RPV DNA. Upstream of the foreign genes is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-glucuronidase (uidA) marker gene is under the control of a late promoter (LP1) and the PRRS ORF2 is inserted into an EcoRI and BamHI site, and is under the control of the early promoter (EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an approximately 1823 base pair NotI restriction fragment of plasmid pRAJ260 (CLONETECH™). Fragment 3 is an EcoRI restriction fragment synthesized by reverse transcription and polymerase chain reaction (PCR) using genomic RNA from a U.S. Isolate of PRRS obtained from the Eichelberger atypical strain. To synthesize PRRS ORF2, the primer 5'-CTGA GAATTCATGGGGGCTATGCAAAGCCTTTTCG-3'; 9/97.13) (SEQ ID NO 43) synthesized from the 5' end of the PRRS ORF2 gene, introduced an EcoRI site at the 5' end of the gene. The primer (5'-GTG GAATTCACCGTGAGTTCGAAAGAAAAATTGC-3'; 9/97.14) (SEQ ID NO 44) was used for reverse transcription and PCR and synthesized from the 3' end of the PRRS ORF2 gene, introduced an EcoRI site at the 3' end of the gene. The PCR product was digested with EcoRI to yield a fragment approximately 771 base pairs in length corresponding to the PRRS ORF2 gene. Fragment 4 is an approximately 895 base pair XbaI to HindIII subfragment of the RPV HindIII fragment U. The XbaI sites in fragments 1 and 3 were converted to unique NotI sites using NotI linkers.

Homology Vector 935-50.1

The plasmid 935-50.1 was constructed for the purpose of inserting foreign DNA into RPV. It incorporates an *E. coli* β-glucuronidase (uidA) marker gene flanked by RPV DNA. Upstream of the foreign gene is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-glucuronidase (uidA) marker gene is under the control of a late promoter (LP1). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an approximately 1823 base pair NotI restriction fragment of plasmid pRAJ260 (CLONETECH™). Fragment 3 is an approximately 895 base pair XbaI to HindIII subfragment of the RPV HindIII fragment U. The XbaI sites in fragments 1 and 3 were converted to unique NotI sites using NotI linkers.

Homology Vector 936-87.2

The plasmid 936-87.2 was constructed for the purpose of inserting foreign DNA into RPV. It incorporates an *E. coli*

β-glucuronidase (uidA) marker gene and the gene for porcine reproductive and respiratory syndrome virus (PRRS) ORF7 (Eichelberger strain) flanked by RPV DNA. Upstream of the foreign genes is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-glucuronidase (uidA) marker gene is under the control of a late promoter (LP1) and the PRRS ORF7 is inserted into an EcoRI and BamHI site, and is under the control of the early promoter (EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an approximately 1823 base pair NotI restriction fragment of plasmid pRAJ260 (CLONETECH™). Fragment 3 is an EcoRI to BamHI restriction fragment synthesized by reverse transcription and polymerase chain reaction (PCR) using genomic RNA from a U.S. Isolate of PRRS obtained from the Eichelberger atypical strain. To synthesize PRRS ORF7, the primer 5'-TATGAATTCTAACAACGGCAAGCAGCA AAAGAAAAAG-3'; 9/97.15) (SEQ ID NO 53) synthesized from the 5' end of the PRRS ORF7 gene, introduced an EcoRI site at the 5' end of the gene. The primer (5μ'- TGT GGATCCATCACGCTGTGGGTGATGCTGTAG-3'; 9/97.16) (SEQ ID NO 54) was used for reverse transcription and PCR and synthesized from the 3' end of the PRRS ORF7 gene, introduced an BamHI site at the 3' end of the gene. The PCR product was digested with EcoRI and BamHI to yield a fragment approximately 372 base pairs in length corresponding to the PRRS ORF7 gene.

Fragment 4 is an approximately 895 base pair XbaI to HindIII subfragment of the RPV HindIII fragment U. The XbaI sites in fragments 1 and 3 were converted to unique NotI sites using NotI linkers.

Homology Vector 938-94.1

The plasmid 938-94.1 was constructed for the purpose of inserting foreign DNA into RPV. It incorporates an *E. coli* β-glucuronidase (uidA) marker gene and the gene for porcine reproductive and respiratory syndrome virus (PRRS) ORF4 (Eichelberger strain) flanked by RPV DNA. Upstream of the foreign genes is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-glucuronidase (uidA) marker gene is under the control of a late promoter (LP1) and the PRRS ORF4 is inserted into an EcoRI and BamHI site, and is under the control of the early promoter (EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an approximately 1823 base pair NotI restriction fragment of plasmid pRAJ260 (CLONETECH™). Fragment 3 is an EcoRI to BamHI restriction fragment synthesized by reverse transcription and polymerase chain reaction (PCR) using genomic RNA from a U.S. Isolate of PRRS obtained from the Eichelberger atypical strain. To synthesize PRRS ORF4, the primer 5'-GG GAATTCTGCGTCCCTTCTTTTCCTCTTGGTTG-3'; 9/97.7) (SEQ ID NO 47) synthesized from the 5' end of the PRRS ORF4 gene, introduced an EcoRI site at the 5' end of the gene. The primer (5'-CTT GGATCCTCAAATTGCCAGCAGGATGGCAAAAAG-3'; 9/97.8) (SEQ ID NO 48) was used for reverse transcription and PCR and synthesized from the 3' end of the PRRS ORF4 gene, introduced an BamHI site at the 3' end of the gene. The PCR product was digested with EcoRI to yield a fragment approximately 542 base pairs in length corresponding to the PRRS ORF4 gene.

Fragment 4 is an approximately 895 base pair XbaI to HindIII subfragment of the RPV HindIII fragment U. The XbaI sites in fragments 1 and 3 were converted to unique NotI sites using NotI linkers.

Homology Vector 938-94.25

The plasmid 938-94.25 was constructed for the purpose of inserting foreign DNA into RPV. It incorporates an *E. coli* β-glucuronidase (uidA) marker gene and the gene for porcine reproductive and respiratory syndrome virus (PRRS) ORF5 (Eichelberger strain) flanked by RPV DNA. Upstream of the foreign genes is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-glucuronidase (uidA) marker gene is under the control of a late promoter (LP1) and the PRRS ORF5 is inserted into an EcoRI and BamHI site, and is under the control of the early promoter (EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an approximately 1823 base pair NotI restriction fragment of plasmid pRAJ260 (CLONETECH™). Fragment 3 is an EcoRI to BamHI restriction fragment synthesized by reverse transcription and polymerase chain reaction (PCR) using genomic RNA from a U.S. Isolate of PRRS obtained from the Eichelberger atypical strain. To synthesize PRRS ORF5, the primer 5'-CAAGGAATTCGGGGAAATGCTTGA CCGCGGGCTG-3'; 9/97.5) (SEQ ID NO 49) synthesized from the 5' end of the PRRS ORF5 gene, introduced an EcoRI site at the 5' end of the gene. The primer (5'-AAAA GGATCCTAGGGACGACCCCATTGTTCAGC-3'; 9/97.6) (SEQ ID NO 50) was used for reverse transcription and PCR and synthesized from the 3' end of the PRRS ORF5 gene, introduced an BamHI site at the 3' end of the gene. The PCR product was digested with EcoRI and BamHI to yield a fragment approximately 606 base pairs in length corresponding to the PRRS ORF5 gene.

Fragment 4 is an approximately 895 base pair XbaI to HindIII subfragment of the RPV HindIII fragment U. The XbaI sites in fragments 1 and 3 were converted to unique NotI sites using NotI linkers.

Homology Vector 950-13.4

The plasmid 950-13.4 was constructed for the purpose of inserting foreign DNA into RPV. It incorporates an E. coli β-glucuronidase (uidA) marker gene and the gene for porcine reproductive and respiratory syndrome virus (PRRS) ORF6 (Eichelberger strain) flanked by RPV DNA. Upstream of the foreign genes is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-glucuronidase (uidA) marker gene is under the control of a late promoter (LP1) and the PRRS ORF6 is inserted into an EcoRI and BamHI site, and is under the control of the early promoter (EP2). It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an approximately 1823 base pair NotI restriction fragment of plasmid pRAJ260 (CLONETECH™). Fragment 3 is an EcoRI to BamHI restriction fragment synthesized by reverse transcription and polymerase chain reaction (PCR) using genomic RNA from a U.S. Isolate of PRRS obtained from the Eichelberger atypical strain. To synthesize PRRS ORF6, the primer 5'-CAAT GAATTCGTCCCTAGACGACTTTTGCAATGATAG-3'; 9/97.5) (SEQ ID NO 51) synthesized from the 5' end of the PRRS ORF6 gene, introduced an EcoRI site at the 5' end of the gene. The primer (5'-CTTGGGATCCTT ATTTGGCATATTTGACAAGGTTTACCAC-3'; 9/97.6) (SEQ ID NO 52) was used for reverse transcription and PCR and synthesized from the 3' end of the PRRS ORF6 gene, introduced an BamHI site at the 3' end of the gene. The PCR product was digested with EcoRI and BamHI to yield a fragment approximately 525 base pairs in length corresponding to the PRRS ORF6 gene.

Fragment 4 is an approximately 895 base pair XbaI to HindIII subfragment of the RPV HindIII fragment U. The XbaI sites in fragments 1 and 3 were converted to unique NotI sites using NotI linkers.

Homology Vector 950-16.34

The plasmid 950-16.34 was constructed for the purpose of inserting foreign DNA into RPV. It incorporates an E. coli β-glucuronidase (uidA) marker gene and the gene for porcine reproductive and respiratory syndrome virus (PRRS) ORF5 and ORF6 (Eichelberger strain) flanked by RPV DNA. Upstream of the foreign genes is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-glucuronidase (uidA) marker gene is under the control of a late promoter (LP1), the PRRS ORF5 is inserted into an EcoRI and BamHI site, and is under the control of the early promoter (EP2), and PRRS ORF6 is inserted into an EcoRI and BamHI site, and is under the control of the late promoter (LP2),. It was constructed utilizing standard recombinant DNA techniques (20, 21), by joining restriction fragments from the following sources with the synthetic DNA sequences. The plasmid vector was derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an approximately 1823 base pair NotI restriction fragment of plasmid pRAJ260 (CLONETECH™). Fragment 3 is an EcoRI to BamHI restriction fragment synthesized by reverse transcription and polymerase chain reaction (PCR) using genomic RNA from a U.S. Isolate of PRRS obtained from the Eichelberger atypical strain. To synthesize PRRS ORF5, the primer 5'-CAAG GAATTCGGGGAAATGCTTGACCGCGGGCTG-3'; 9/97.5) (SEQ ID NO 49) synthesized from the 5' end of the PRRS ORF5 gene, introduced an EcoRI site at the 5' end of the gene. The primer (5'-AAAA GGATCCTAGGGACGACCCCATTGTTCAGC-3'; 9/97.6) (SEQ ID NO 50) was used for reverse transcription and PCR and synthesized from the 3' end of the PRRS ORF5 gene, introduced an BamHI site at the 3' end of the gene. The PCR product was digested with EcoRI and BamHI to yield a fragment approximately 606 base pairs in length corresponding to the PRRS ORF5 gene.

Fragment 4 is an EcoRI to BamHI restriction fragment synthesized by reverse transcription and polymerase chain reaction (PCR) using genomic RNA from a U.S. Isolate of PRRS obtained from the Eichelberger atypical strain. To synthesize PRRS ORF6, the primer 5'-CAAT GAATTCGTCCCTAGACGACTTTTGCAATGATAG-3'; 9/97.5) (SEQ ID NO 51) synthesized from the 5' end of the PRRS ORF6 gene, introduced an EcoRI site at the 5' end of the gene. The primer (5'-CTTGGGATCCTT ATTTGGCATATTTGACAAGGTTTACCAC-3'; 9/97.6) (SEQ ID NO 52) was used for reverse transcription and PCR and synthesized from the 3' end of the PRRS ORF6 gene, introduced an BamHI site at the 3' end of the gene. The PCR product was digested with EcoRI and BamHI to yield a fragment approximately 525 base pairs in length corresponding to the PRRS ORF6 gene.

Fragment 5 is an approximately 895 base pair XbaI to HindIII subfragment of the RPV HindIII fragment U. The XbaI sites in fragments 1 and 3 were converted to unique NotI sites using NotI linkers.

Homology Vector for S-RPV-014

The plasmid is constructed for the purpose of inserting foreign DNA into RPV. It incorporates an E. coli β-galactosidase (lacZ) marker gene flanked by RPV DNA. Upstream of the foreign gene is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-galactosidase (lacZ) marker gene is under the control of a late promoter, swinepox virus I5L (FIG. 9). It is constructed utilizing standard recombinant DNA techniques (20, 21), by joining restriction fragments from the following sources with the synthetic DNA sequences. The plasmid vector is derived from an approximately 2999 base pair HindIII restriction fragment of pSP64 (PROMEGA™). Fragment 1 is an approximately 906 base pair HindIII to XbaI restriction sub-fragment of the RPV HindIII restriction fragment U (6). Fragment 2 is an 3010 base pair BamHI to PvuII restriction fragment of plasmid pJF751 (25). Fragment 3 is an approximately 895 base pair XbaI to HindIII subfragment of the RPV HindIII fragment U. The XbaI sites in fragments 1 and 3 were converted to unique NotI sites using NotI linkers.

EXAMPLE 1

Recombinant raccoonpox virus (RPV) capable of replication which contains foreign DNA encoding an antigenic polypeptide is useful to prevent disease in porcine, bovine, sheep, goats, ovine, caprine, feline, canine, avian, equine, and human species. Useful insertion sites for foreign DNA in non-essential regions in the raccoonpox virus genome are in genomic fragments HindIII U (2.1 kb), HindIII M (6.0 kb), HindIII N (5.1 kb), HindIII W (1.5 kb), HindIII T (2.2 kb, HindIII P (4.5 kb). Open reading frames in each of these fragments which are suitable for insertion of foreign DNA include, but are not limited to: O1L homolog, E11L homolog in HindIII U; D1L homolog, C17L/B23R homolog in HindIII M; D1L homolog, B22R homolog in HindIII N; N1L homolog, N2L homolog, M1L homolog, M2L homolog, K1L homolog, K2L homolog, K7R homolog in HindIII W, T, or P.

EXAMPLE 2

S-RPV-001

S-RPV-001 is a raccoonpox virus that expresses at least two foreign genes. The gene for E. coli β-galactosidase (lacZ) and the gene for swine influenza virus (SIV) HA (H1N1) were inserted into the RPV O1L ORF (a unique NotI restriction site has replaced an XbaI restriction site) within the RPV HindIII "U" genomic fragment. The lacZ gene is under the control of the synthetic late promoter (LP1), and the SIV HA gene is under the control of the synthetic late/early promoter (LP2EP2). Transcription of the SIV HA gene is opposite to the direction of transcription of the lacZ gene and opposite to the direction of transcription of the RPV O1L ORF.

S-RPV-001 was derived from S-RPV-000 (ATCC Strain VR-838). This was accomplished utilizing the homology vector 902-16.2 (see Materials and Methods) and virus S-RPV-000 in the HOMOLOGOUS RECOMBINATION PROCEDURE FOR GENERATING RECOMBINANT RPV. The transfection stock was screened by the SCREEN FOR RECOMBINANT RPV EXPRESSING β-galactosidase (BLUOGAL™ AND CPRG ASSAYS). The final result of red plaque purification was the recombinant virus designated S-RPV-001. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-RPV-001 was assayed for expression of SIV-specific antigens using the BLACK PLAQUE SCREEN FOR FOREIGN GENE EXPRESSION IN RECOMBINANT RPV. Polyclonal swine anti-SIV serum or polyclonal goat anti-HA serum was shown to react specifically with S-RPV-001 plaques and not with S-RPV-000 negative control plaques. All S-RPV-001 observed plaques reacted with the antiserum indicating that the virus was stably expressing the SIV HA protein.

To confirm the expression of the SIV HA protein gene product, cells were infected with S-RPV-001 and samples of infected cell lysates and culture supernatants were subjected to SDS polyacrylamide gel electrophoresis. The gel was blotted and analyzed using the WESTERN BLOTTING PROCEDURE. Polyclonal swine anti-SIV serum or polyclonal goat anti-HA serum was used to detect expression of SIV specific proteins. The cell lysate and culture supernatant from S-RPV-001 infected cells exhibited bands corresponding to 64 kd, which is the expected size of the SIV HA protein.

S-RPV-001 is useful as a vaccine in swine against swine influenza infection. S-RPV-001 is useful as a vaccine in combination with S-RPV-003 which expresses SIV NA. S-RPV-001 is also useful for expression of the SIV HA protein.

EXAMPLE 3

S-RPV-002

S-RPV-002 (ATCC Accession No. VR-2597) is a raccoonpox virus (RPV) that expresses at least two foreign genes. The gene for E. coli β-galactosidase (lacZ) and the gene for swine influenza virus (SIV) HA (H1N1) were inserted into the RPV O1L ORF (a unique NotI restriction site has replaced an XbaI restriction site) within the RPV HindIII "U" genomic fragment. The lacZ gene is under the control of the synthetic late promoter (LP1), and the SIV HA gene is under the control of the synthetic late/early promoter (LP2EP2). In contrast to S-RPV-001, direction of transcription of the SIV HA gene in S-RPV-002 is the same as the direction of transcription of the lacZ gene and the direction of transcription of the RPV O1L ORF.

S-RPV-002 was deposited on Feb. 6, 1998 with the American Type Culture Collection (ATCC), 10801 University Boulevard, Manassas, Va. 20108-0971, U.S.A. under the provisions of the Budapest Treaty for the International Recognition of the Deposit of Microorganisms for the Purposes of Patent Procedure.

S-RPV-002 was derived from S-RPV-000 (ATCC Strain VR-838). This was accomplished utilizing the homology vector 902-19.18 (see Materials and Methods) and virus S-RPV-000 in the HOMOLOGOUS RECOMBINATION PROCEDURE FOR GENERATING RECOMBINANT RPV. The transfection stock was screened by the SCREEN FOR RECOMBINANT RPV EXPRESSING β-galactosidase (BLUOGAL™ AND CPRG ASSAYS). The final result of red plaque purification was the recombinant virus designated S-RPV-002. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-RPV-002 was assayed for expression of SIV-specific antigens using the BLACK PLAQUE SCREEN FOR FOREIGN GENE EXPRESSION IN RECOMBINANT RPV. Polyclonal swine anti-SIV serum or polyclonal goat anti-HA serum was shown to react specifically with S-RPV-002 plaques and not with S-RPV-000 negative control plaques. All S-RPV-002 observed plaques reacted with the antiserum indicating that the virus was stably expressing the SIV HA protein.

To confirm the expression of the SIV HA protein gene product, cells were infected with S-RPV-002 and samples of infected cell lysates and culture supernatants were subjected to SDS polyacrylamide gel electrophoresis. The gel was blotted and analyzed using the WESTERN BLOTTING PROCEDURE. Polyclonal swine anti-SIV serum or polyclonal goat anti-HA serum was used to detect expression of SIV specific proteins. The cell lysate and culture supernatant from S-RPV-002 infected cells exhibited bands corresponding to 64 kd, which is the expected size of the SIV HA protein.

S-RPV-002 is useful as a vaccine in swine against swine influenza infection. S-RPV-002 is useful as a vaccine in combination with S-RPV-003 which expresses SIV NA. S-RPV-002 is also useful for expression of the SIV HA protein.

EXAMPLE 4

S-RPV-003

S-RPV-003 is a raccoonpox virus (RPV) that expresses at least two foreign genes. The gene for *E. coli* β-galactosidase (lacZ) and the gene for swine influenza virus (SIV) NA (H1N1) were inserted into the RPV O1L ORF (a unique NotI restriction site has replaced an XbaI restriction site) within the RPV HindIII "U" genomic fragment. The lacZ gene is under the control of the synthetic late promoter (LP1), and the SIV NA gene is under the control of the synthetic late/early promoter (LP2EP2).

S-RPV-003 was derived from S-RPV-000 (ATCC Strain VR-838). This was accomplished utilizing the homology vector 902-49.5 (see Materials and Methods) and virus S-RPV-000 in the HOMOLOGOUS RECOMBINATION PROCEDURE FOR GENERATING RECOMBINANT RPV. The transfection stock was screened by the SCREEN FOR RECOMBINANT RPV EXPRESSING β-galactosidase (BLUOGAL™ AND CPRG ASSAYS). The final result of red plaque purification was the recombinant virus designated S-RPV-003. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-RPV-003 was assayed for expression of SIV-specific antigens using the BLACK PLAQUE SCREEN FOR FOREIGN GENE EXPRESSION IN RECOMBINANT RPV. Polyclonal swine anti-SIV serum was shown to react specifically with S-RPV-003 plaques and not with S-RPV-000 negative control plaques. All S-RPV-003 observed plaques reacted with the antiserum indicating that the virus was stably expressing the SIV NA protein.

To confirm the expression of the SIV NA protein gene product, cells were infected with S-RPV-003 and samples of infected cell lysates and culture supernatants were subjected to SDS polyacrylamide gel electrophoresis. The gel was blotted and analyzed using the WESTERN BLOTTING PROCEDURE. Polyclonal goat anti-NA serum was used to detect expression of SIV specific proteins. The cell lysate and culture supernatant from S-RPV-003 infected cells exhibited bands corresponding to 64 kd, which is the expected size of the SIV NA protein.

S-RPV-003 is useful as a vaccine in swine against swine influenza infection. S-RPV-003 is useful as a vaccine in combination with S-RPV-001 or S-RPV-002 which express SIV HA. S-RPV-003 is also useful for expression of the SIV NA protein.

Polyclonal murine antibodies to SIV NA were produced using S-RPV-003 according to the PROCEDURE TO PRODUCE MURINE POLYCLONAL ANTIBODIES TO PROTEINS EXPRESSED IN RECOMBINANT RACCOONPOX VIRUS. BLACK PLAQUE ASSAYS were conducted, using the mouse anti S-RPV-003 serum, against recombinant swinepox virus (SPV) expressing swine influenza virus HA or NA proteins. The mouse anti S-RPV-003 serum (1:100 dil) was shown to react specifically with recombinant SPV expressing NA. The serum did not cross react to either recombinant SPV expressing SIV HA or -galactosidase.

EXAMPLE 5

S-RPV-004

S-RPV-004 is a raccoonpox virus (RPV) that expresses at least two foreign genes. The gene for *E. coli* β-galactosidase (lacZ) and the gene for porcine reproductive and respiratory syndrome virus (PRRS) ORF3 were inserted into the RPV O1L ORF (a unique NotI restriction site has replaced an XbaI restriction site) within the RPV HindIII "U" genomic fragment. The lacZ gene is under the control of the synthetic late promoter (LP1), and the PRRS ORF3 gene is under the control of the synthetic late/early promoter (LP2EP2).

S-RPV-004 was derived from S-RPV-000 (ATCC Strain VR-838). This was accomplished utilizing the homology vector 902-49.14 (see Materials and Methods) and virus S-RPV-000 in the HOMOLOGOUS RECOMBINATION PROCEDURE FOR GENERATING RECOMBINANT RPV. The transfection stock was screened by the SCREEN FOR RECOMBINANT RPV EXPRESSING β-galactosidase (BLUOGAL™ AND CPRG ASSAYS). The final result of red plaque purification was the recombinant virus designated S-RPV-004. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-RPV-004 was assayed for expression of PRRS-specific antigens using the BLACK PLAQUE SCREEN FOR FOREIGN GENE EXPRESSION IN RECOMBINANT RPV. Polyclonal swine anti-PRRS serum was shown to react specifically with S-RPV-004 plaques and not with S-RPV-000 negative control plaques. All S-RPV-004 observed plaques reacted with the antiserum indicating that the virus was stably expressing the PRRS ORF3 protein.

To confirm the expression of the PRRS ORF3 protein gene product, cells were infected with S-RPV-004 and samples of infected cell lysates and culture supernatants were subjected to SDS polyacrylamide gel electrophoresis. The gel was blotted and analyzed using the WESTERN BLOTTING PROCEDURE. A polyclonal swine anti-PRRS serum was used to detect expression of PRRS specific proteins. The cell lysate a nd culture supernatant from S-RPV-004 infected cells exhibited a band corresponding to 45 kd, which is the expected size of the PRRS ORF3 protein. ORF3 protein is secreted from infected cells into the culture media.

S-RPV-004 is useful as a vaccine in swine against PRRS infection. S-RPV-004 is useful as a vaccine in combination with S-RPV-005 and S-RPV-006 which express PRRS ORF4 and PRRS ORF5, respectively. S-RPV-004 is also useful for expression of the PRRS ORF3 protein.

Polyclonal murine antibodies to PRRS ORF3 were produced using S-RPV-004 according to the PROCEDURE TO PRODUCE MURINE POLYCLONAL ANTIBODIES TO PROTEINS EXPRESSED IN RECOMBINANT RACCOONPOX VIRUS. BLACK PLAQUE ASSAYS are conducted, using the mouse anti S-RPV-004 serum, against recombinant swinepox virus (SPV) expressing PRRS ORF3, ORF4 or ORF5 proteins.

EXAMPLE 6

S-RPV-005

S-RPV-005 is a raccoonpox virus (RPV) that expresses at least two foreign genes. The gene for *E. coli* β-galactosidase (lacZ) and the gene for porcine reproductive and respiratory syndrome virus (PRRS) ORF4 were inserted into the RPV O1L ORF (a unique NotI restriction site has replaced an XbaI restriction site) within the RPV HindIII "U" genomic fragment. The lacZ gene is under the control of the synthetic late promoter (LP1), and the PRRS ORF4 gene is under the control of the synthetic late/early promoter (LP2EP2).

S-RPV-005 was derived from S-RPV-000 (ATCC Strain VR-838). This was accomplished utilizing the homology vector 902-49.23 (see Materials and Methods) and virus S-RPV-000 in the HOMOLOGOUS RECOMBINATION PROCEDURE FOR GENERATING RECOMBINANT RPV. The transfection stock was screened by the SCREEN FOR RECOMBINANT RPV EXPRESSING β-galactosidase (BLOUGAL™ AND CPRG ASSAYS). The final result of red plaque purification was the recombinant virus designated S-RPV-005. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-RPV-005 was assayed for expression of PRRS-specific antigens using the BLACK PLAQUE SCREEN FOR FOREIGN GENE EXPRESSION IN RECOMBINANT RPV. Polyclonal swine anti-PRRS serum was shown to react specifically with S-RPV-005 plaques and not with S-RPV-000 negative control plaques. All S-RPV-005 observed plaques reacted with the antiserum indicating that the virus was stably expressing the PRRS ORF4 protein.

To confirm the expression of the PRRS ORF4 protein gene product, cells were infected with S-RPV-005 and samples of infected cell lysates were subjected to SDS polyacrylamide gel electrophoresis. The gel was blotted and analyzed using the WESTERN BLOTTING PROCEDURE. A polyclonal swine anti-PRRS serum was used to detect expression of PRRS specific proteins. The cell lysate from S-RPV-005 infected cells exhibited a band corresponding to 3' kd, which is the expected size of the PRRS ORF4 protein (202 amino acids).

S-RPV-005 is useful as a vaccine in swine against PRRS infection. S-RPV-005 is useful as a vaccine in combination with S-RPV-004 and S-RPV-006 which express PRRS ORF3 and PRRS ORF5, respectively. S-RPV-005 is also useful for expression of the PRRS ORF4 protein.

Polyclonal murine antibodies to PRRS ORF4 were produced using S-RPV-005 according to the PROCEDURE TO PRODUCE MURINE POLYCLONAL ANTIBODIES TO PROTEINS EXPRESSED IN RECOMBINANT RACCOONPOX VIRUS. BLACK PLAQUE ASSAYS are conducted, using the mouse anti S-RPV-005 serum, against recombinant swinepox virus (SPV) expressing PRRS ORF3, ORF4 or ORF5 proteins.

EXAMPLE 7

S-RPV-006

S-RPV-006 is a raccoonpox virus (RPV) that expresses at least two foreign genes. The gene for *E. coli* β-galactosidase (lacZ) and the gene for porcine reproductive and respiratory syndrome virus (PRRS) ORF5 were inserted into the RPV O1L ORF (a unique NotI restriction site has replaced an XbaI restriction site) within the RPV HindIII "U" genomic fragment. The lacZ gene is under the control of the synthetic late promoter (LP1), and the PRRS ORF5 gene is under the control of the synthetic late/early promoter (LP2EP2).

S-RPV-006 was derived from S-RPV-000 (ATCC Strain VR-838). This was accomplished utilizing the homology vector 902-49.34 (see Materials and Methods) and virus S-RPV-000 in the HOMOLOGOUS RECOMBINATION PROCEDURE FOR GENERATING RECOMBINANT RPV. The transfection stock was screened by the SCREEN FOR RECOMBINANT RPV EXPRESSING β-galactosidase (BLUOGAL™ AND CPRG ASSAYS). The final result of red plaque purification was the recombinant virus designated S-RPV-006. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

To confirm the expression of the PRRS ORF5 protein gene product, cells were infected with S-RPV-006 and samples of infected cell lysates were subjected to SDS polyacrylamide gel electrophoresis. The gel was blotted and analyzed using the WESTERN BLOTTING PROCEDURE. A polyclonal swine anti-PRRS serum was used to detect expression of PRRS specific proteins. The cell lysate from S-RPV-006 infected cells exhibited a band corresponding to 26 kd, which is the expected size of the PRRS ORF5 protein.

S-RPV-006 is useful as a vaccine in swine against PRRS infection. S-RPV-006 is useful as a vaccine in combination with S-RPV-004 and S-RPV-005 which express PRRS ORF3 and PRRS ORF4, respectively. S-RPV-006 is also useful for expression of the PRRS ORF5 protein.

EXAMPLE 8

S-RPV-007

S-RPV-007 is a raccoonpox virus (RPV) that expresses at least one foreign gene. The gene for *E. coli* β-galactosidase (lacZ) was inserted into the RPV O1L ORF (a unique NotI restriction site has replaced an XbaI restriction site) within the RPV HindIII "U" genomic fragment. The lacZ gene is under the control of the synthetic late promoter (LP1), and second foreign DNA is inserted into a unique EcoRI or BamHI site under the control of the synthetic late/early promoter (LP2EP2).

S-RPV-007 was derived from S-RPV-000 (ATCC Strain VR-838). This was accomplished utilizing the homology vector 902-49.46 (see Materials and Methods) and virus S-RPV-000 in the HOMOLOGOUS RECOMBINATION PROCEDURE FOR GENERATING RECOMBINANT RPV. The transfection stock was screened by the SCREEN FOR RECOMBINANT RPV EXPRESSING β-galactosidase (BLOUGAL™ AND CPRG ASSAYS). The final result of red plaque purification was the recombinant virus designated S-RPV-007. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-RPV-007 is useful as a vaccine in mammalian and avian species. When a foreign DNA encoding an antigenic polypeptide form an avian or mammalian pathogen, or encoding a cytokine or immune-modulating protein is inserted under the control of the LP2EP2 promoter in an EcoRI or BamHI site in S-RPV-007, the resulting recombinant virus is useful as a vaccine against the avian or mammalian pathogen.

The XbaI site within the RPV genomic fragment HindIII U is a useful insertion site for foreign DNA. A second foreign DNA is inserted into S-RPV-007 at a unique EcoRI or BamHI insertion site and is under control of the synthetic late/early promoter, LP2EP2. When the second foreign DNA encodes an antigenic polypeptide from an avian or mammalian pathogen, or encodes a cytokine or immune-modulating protein, the resulting recombinant virus is useful as a vaccine against the avian or mammalian pathogen.

EXAMPLE 9

S-RPV-008

S-RPV-008 (ATTC Accession No. VR-2598) is a raccoonpox virus (RPV) that expresses at least one foreign gene. The gene for *E. coli* β-galactosidase (lacZ) was inserted into a unique SnaB I site within the RPV genomic fragment HindIII N (a unique NotI restriction site has replaced a SnaBI restriction site). The lacZ gene is under the control of the synthetic late promoter (LP1), and second foreign DNA is inserted into a unique EcoRI or BamHI site under the control of the synthetic late/early promoter (LP2EP2).

S-RPV-008 was deposited on February 6, 1998 with the American Type Culture Collection (ATCC), 10801 University Boulevard, Manassas, Va 20108-0971, U.S.A. under the provisions of the Budapest Treaty for the International Recognition of the Deposit of Microorganisms for the Purposes of Patent Procedure.

S-RPV-008 was derived from S-RPV-000 (ATCC Strain VR-838). This was accomplished utilizing the homology vector 902-67.1 (see Materials and Methods) and virus S-RPV-000 in the HOMOLOGOUS RECOMBINATION PROCEDURE FOR GENERATING RECOMBINANT RPV. The transfection stock was screened by the SCREEN FOR RECOMBINANT RPV EXPRESSING β-galactosidase (BLUOGAL™ AND CPRG ASSAYS). The final result of red plaque purification was the recombinant virus designated S-RPV-008. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-RPV-008 is useful as a vaccine in mammalian and avian species. When a foreign DNA encoding an antigenic polypeptide form an avian or mammalian pathogen, or encoding a cytokine or immune-modulating protein is inserted under the control of the LP2EP2 promoter in an EcoRI or BamHI site in S-RPV-008, the resulting recombinant virus is useful as a vaccine against the avian or mammalian pathogen.

The SnaBI site within the RPV genomic fragment HindIII N is a useful insertion site for foreign DNA. A second foreign DNA is inserted into S-RPV-008 at a unique EcoRI or BamHI insertion site and is under control of the synthetic late/early promoter, LP2EP2. When the second foreign DNA encodes an antigenic polypeptide from an avian or mammalian pathogen, or encodes a cytokine or immune-modulating protein, the resulting recombinant virus is useful as a vaccine against the avian or mammalian pathogen.

EXAMPLE 10

S-RPV-009

S-RPV-009 (ATCC Accession No. VR-2599) is a raccoonpox virus (RPV) that expresses at least one foreign gene. The gene for *E. coli* β-galactosidase (lacZ) was inserted into a unique EcoRV site within the RPV genomic fragment HindIII N (a unique NotI restriction site has replaced an EcoRV restriction site). The lacZ gene is under the control of the synthetic late promoter (LP1).

S-RPV-009 was deposited on Feb. 6, 1998 with the American Type Culture Collection (ATCC), 10801 University Boulevard, Manassas, Va. 20108-0971, U.S.A. under the provisions of the Budapest Treaty for the International Recognition of the Deposit of Microorganisms for the Purposes of Patent Procedure.

S-RPV-009 was derived from S-RPV-000 (ATCC Strain VR-838). This was accomplished utilizing the homology vector 902-67.14 (see Materials and Methods) and virus S-RPV-000 in the HOMOLOGOUS RECOMBINATION PROCEDURE FOR GENERATING RECOMBINANT RPV. The transfection stock was screened by the SCREEN FOR RECOMBINANT RPV EXPRESSING 1-galactosidase (BLOUGAL™ AND CPRG ASSAYS). The final result of red plaque purification was the recombinant virus designated S-RPV-009. This virus was assayed for 1-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-RPV-009 is useful as a vaccine in mammalian and avian species. When a foreign DNA encoding an antigenic polypeptide form an avian or mammalian pathogen, or encoding a cytokine or immune-modulating protein is inserted under the control of the LP2EP2 promoter in an EcoRI or BamHI site in S-RPV-009, the resulting recombinant virus is useful as a vaccine against the avian or mammalian pathogen.

The EcoRV site within the RPV genomic fragment HindIII N is a useful insertion site for foreign DNA. A second foreign DNA is inserted into S-RPV-009 at a unique EcoRI or BamHI insertion site and is under control of the synthetic late/early promoter, LP2EP2. When the second foreign DNA encodes an antigenic polypeptide from an avian or mammalian pathogen, or encodes a cytokine or immune-modulating protein, the resulting recombinant virus is useful as a vaccine against the avian or mammalian pathogen.

EXAMPLE 11

S-RPV-010

S-RPV-010 is a raccoonpox virus (RPV) that expresses at least one foreign gene. The gene for *E. coli* β-galactosidase (lacZ) was inserted into a unique HpaI site within the RPV genomic fragment HindIII M (a unique NotI restriction site has replaced a HpaI restriction site). The lacZ gene is under the control of the synthetic late promoter (LP1).

S-RPV-010 was derived from S-RPV-000 (ATCC Strain VR-838). This was accomplished utilizing the homology vector 902-67.27(see Materials and Methods) and virus S-RPV-000 in the HOMOLOGOUS RECOMBINATION PROCEDURE FOR GENERATING RECOMBINANT RPV. The transfection stock was screened by the SCREEN FOR RECOMBINANT RPV EXPRESSING β-galactosidase (BLOUGAL™ AND CPRG ASSAYS). The final result of red plaque purification was the recombinant virus designated S-RPV-010. This virus was assayed for β-galactosidase expression, purity, and insert stability by multiple passages monitored by the blue plaque assay as described in Materials and Methods.

S-RPV-010 is useful as a vaccine in mammalian and avian species. When a foreign DNA encoding an antigenic polypeptide form an avian or mammalian pathogen, or encoding a cytokine or immune-modulating protein is inserted under the control of the LP2EP2 promoter in an EcoRI or BamHI site in S-RPV-010, the resulting recombinant virus is useful as a vaccine against the avian or mammalian pathogen.

The HpaI site within the RPV genomic fragment HindIII M is a useful insertion site for foreign DNA. A second foreign DNA is inserted into S-RPV-010 at a unique EcoRI or BamHI insertion site and is under control of the synthetic late/early promoter, LP2EP2. When the second foreign DNA encodes an antigenic polypeptide from an avian or mammalian pathogen, or encodes a cytokine or immune-modulating protein, the resulting recombinant virus is useful as a vaccine against the avian or mammalian pathogen.

EXAMPLE 12

S-RPV-011

S-RPV-011 is a raccoonpox virus (RPV) that expresses at least one foreign gene. The gene for *E. coli* β-glucuronidase (uidA) was inserted into the RPV O1L ORF (a unique NotI restriction site has replaced an XbaI restriction site) within the RPV HindIII "U" genomic fragment. The uida gene is under the control of the synthetic late promoter (LP1).

S-RPV-011 was derived from S-RPV-000 (ATCC Strain VR-838). This was accomplished utilizing the homology vector 919-16.12 (see Materials and Methods) and virus S-RPV-000 in the HOMOLOGOUS RECOMBINATION PROCEDURE FOR GENERATING RECOMBINANT RPV. The transfection stock was screened by the SCREEN FOR RECOMBINANT RPV EXPRESSING β-glucuronidase (X-GLUC™ ASSAYS). The final result of blue plaque purification was the recombinant virus designated S-RPV-011. This virus was assayed for β-glucuronidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-RPV-011 is useful as a vaccine in mammalian and avian species. When a second foreign DNA encoding an antigenic polypeptide from an avian or mammalian pathogen, or encoding a cytokine or immune-modulating protein is inserted under the control of the LP2EP2 promoter in a unique EcoRI or BamHI site in S-RPV-011, the resulting recombinant virus is useful as a vaccine against the avian or mammalian pathogen.

EXAMPLE 13

S-RPV-012

S-RPV-012 is a raccoonpox virus (RPV) that expresses at least two foreign genes. The gene for *E. coli* β-galactosidase (lacZ) and the gene for porcine parvovirus (PPV) VP2 capsid protein were inserted into the RPV O1L ORF (a unique NotI restriction site has replaced an XbaI restriction site) within the RPV HindIII "U" genomic fragment. The lacZ gene is under the control of the synthetic late promoter (LP1), and the PPV VP2 gene is under the control of the synthetic late/early promoter (LP2EP2).

S-RPV-012 was derived from S-RPV-000 (ATCC Strain VR-838). This was accomplished utilizing the homology vector 919-63.21 (see Materials and Methods) and virus S-RPV-000 in the HOMOLOGOUS RECOMBINATION PROCEDURE FOR GENERATING RECOMBINANT RPV. The transfection stock was screened by the SCREEN FOR RECOMBINANT RPV EXPRESSING β-galactosidase (BLOUGAL™ AND CPRG ASSAYS). The final result of red plaque purification was the recombinant virus designated S-RPV-012. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-RPV-012 is useful as a vaccine in swine against porcine parvovirus infection. S-RPV-012 is also useful for expression of the PPV VP2 protein.

EXAMPLE 14

S-RPV-013

S-RPV-013 is a raccoonpox virus (RPV) that expresses at least one foreign gene. The gene for *E. coli* β-glucuronidase (uidA) is inserted into the RPV O1L ORF (a unique NotI restriction site has replaced an XbaI restriction site) within the RPV HindIII "U" genomic fragment. The uida gene is under the control of the synthetic late promoter (LP1).

S-RPV-013 is derived from S-RPV-000 (ATCC Strain VR-838). This is accomplished utilizing the HOMOLOGY VECTOR 935-50.1 (see Materials and Methods) and virus S-RPV-000 in the HOMOLOGOUS RECOMBINATION PROCEDURE FOR GENERATING RECOMBINANT RPV. The transfection stock is screened by the SCREEN FOR RECOMBINANT RPV EXPRESSING β-glucuronidase (X-GLUC™ ASSAYS). The final result of blue plaque purification is the recombinant virus designated S-RPV-013. This virus is assayed for β-glucuronidase expression, purity, and insert stability by multiple passages monitored by the blue plaque assay as described in Materials and Methods. After the initial three rounds of purification, all plaques observed are blue indicating that the virus is pure, stable, and expressing the foreign gene.

S-RPV-013 is useful as a vaccine in mammalian and avian species. When a second foreign DNA encoding an antigenic polypeptide from an avian or mammalian pathogen, or encoding a cytokine or immune-modulating protein is inserted under the control of a promoter in a unique site in S-RPV-013, the resulting recombinant virus is useful as a vaccine against the avian or mammalian pathogen.

EXAMPLE 15

S-RPV-014

S-RPV-014 is a raccoonpox virus (RPV) that expresses at least one foreign gene. The gene for *E. coli* β-galactosidase (lacZ) is inserted into the RPV O1L ORF (a unique NotI restriction site has replaced an XbaI restriction site) within the RPV HindIII "U" genomic fragment. The lacZ gene is under the control of the swinepox virus I5L promoter (see FIG. 9).

S-RPV-014 is derived from S-RPV-000 (ATCC Strain VR-838). This is accomplished utilizing the HOMOLOGY VECTOR FOR S-RPV-014 (see Materials and Methods) and virus S-RPV-000 in the HOMOLOGOUS RECOMBINATION PROCEDURE FOR GENERATING RECOMBINANT RPV. The transfection stock is screened by the SCREEN FOR RECOMBINANT RPV EXPRESSING β-GALACTOSIDASE (BLUOGAL ASSAY). The final result of blue plaque purification is the recombinant virus designated S-RPV-014. This virus is assayed for β-galactosidase expression, purity, and insert stability by multiple passages monitored by the blue plaque assay as described in Materials and Methods. After the initial three rounds of purification, all plaques observed are blue indicating that the virus is expressing the foreign gene.

S-RPV-014 is useful as a vaccine in mammalian and avian species. When a second foreign DNA encoding an antigenic polypeptide from an avian or mammalian pathogen, or encoding a cytokine or immune-modulating protein is inserted under the control of a promoter in a unique site in S-RPV-014, the resulting recombinant virus is useful as a vaccine against the avian or mammalian pathogen. The SPV I5L promoter is a useful heterologous promoter in a recombinant raccoonpox virus. THE SPV I5L promoter is a strong late promoter.

EXAMPLE 16

S-RPV-015

S-RPV-015 is a raccoonpox virus (RPV) that expresses at least two foreign genes. The gene for *E. coli* β-glucuronidase (uidA) and the gene for porcine reproductive and respiratory syndrome virus (PRRS) ORF2 (Eichelberger strain) are inserted into the RPV O1L ORF (a unique NotI restriction site has replaced an XbaI restriction site) within the RPV HindIII "U" genomic fragment. The uida gene is under the control of the synthetic late promoter (LP1), and the PRRS ORF2 gene is under the control of the synthetic early promoter (EP2).

S-RPV-015 is derived from S-RPV-000 (ATCC Strain VR-838). This is accomplished utilizing the HOMOLOGY VECTOR 934-65.1 (see Materials and Methods) and virus S-RPV-000 in the HOMOLOGOUS RECOMBINATION PROCEDURE FOR GENERATING RECOMBINANT RPV. The transfection stock is screened by the SCREEN FOR RECOMBINANT RPV EXPRESSING β-glucuronidase (X-GLUC™ ASSAYS). The final result of blue plaque purification is the recombinant virus designated S-RPV-015. This virus is assayed for β-glucuronidase expression, purity, and insert stability by multiple passages monitored by the blue plaque assay as described in Materials and Methods. After the initial three rounds of purification, all plaques observed were blue indicating that the virus is pure, stable, and expressing the foreign gene.

S-RPV-015 is assayed for expression of PRRS-specific antigens using the BLACK PLAQUE SCREEN FOR FOREIGN GENE EXPRESSION IN RECOMBINANT RPV. Rabbit polyclonal anti β-glucuronidase antibody is shown to react specifically with S-RPV-015 plaques and not with S-RPV-000 negative control plaques.

S-RPV-015 is useful as a vaccine in swine against PRRS infection. S-RPV-015 is useful as a vaccine in combination with S-RPV-016, S-RPV-017, S-RPV-018, S-RPV-019, and S-RPV-020 which express PRRS ORF3, ORF4, ORF5, ORF6 and ORF7, respectively. S-RPV-015 is also useful for expression of the PRRS ORF2 protein for purposes of raising antibodies to PRRS ORF2 and for diagnostic assays.

EXAMPLE 17

S-RPV-016

S-RPV-016 is a raccoonpox virus (RPV) that expresses at least two foreign genes. The gene for E. coli β-glucuronidase (uidA) and the gene for porcine reproductive and respiratory syndrome virus (PRRS) ORF3 (Eichelberger strain) are inserted into the RPV O1L ORF (a unique NotI restriction site has replaced an XbaI restriction site) within the RPV HindIII "U" genomic fragment. The uida gene is under the control of the synthetic late promoter (LP1), and the PRRS ORF3 gene is under the control of the synthetic late/early promoter (LP2EP2).

S-RPV-016 is derived from S-RPV-000 (ATCC Strain VR-838). This is accomplished utilizing the HOMOLOGY VECTOR 934-64.2 (see Materials and Methods) and virus S-RPV-000 in the HOMOLOGOUS RECOMBINATION PROCEDURE FOR GENERATING RECOMBINANT RPV. The transfection stock is screened by the SCREEN FOR RECOMBINANT RPV EXPRESSING β-glucuronidase (X-GLUC™ ASSAYS). The final result of blue plaque purification is the recombinant virus designated S-RPV-016. This virus is assayed for β-glucuronidase expression, purity, and insert stability by multiple passages monitored by the blue plaque assay as described in Materials and Methods. After the initial three rounds of purification, all plaques observed were blue indicating that the virus is pure, stable, and expressing the foreign gene.

S-RPV-016 is assayed for expression of PRRS-specific antigens using the BLACK PLAQUE SCREEN FOR FOREIGN GENE EXPRESSION IN RECCMBINANT RPV. Rabbit polyclonal anti β-glucuronidase antibody is shown to react specifically with S-RPV-016 plaques and not with S-RPV-000 negative control plaques.

S-RPV-016 is useful as a vaccine in swine against PRRS infection. S-RPV-016 is useful as a vaccine in combination with S-RPV-015, S-RPV-017, S-RPV-018, S-RPV-019, and S-RPV-020 which express PRRS ORF2, ORF4, ORF5, ORF6 and ORF7, respectively. S-RPV-016 is also useful for expression of the PRRS ORF3 protein for purposes of raising antibodies to PRRS ORF3 and for diagnostic assays.

EXAMPLE 18

S-RPV-017

S-RPV-017 is a raccoonpox virus (RPV) that expresses at least two foreign genes. The gene for E. coli β-glucuronidase (uidA) and the gene for porcine reproductive and respiratory syndrome virus (PRRS) ORF4 (Eichelberger strain) are inserted into the RPV O1L ORF (a unique NotI restriction site has replaced an XbaI restriction site) within the RPV HindIII "U" genomic fragment. The uidA gene is under the control of the synthetic late promoter (LP1), and the PRRS ORF4 gene is under the control of the synthetic late/early promoter (LP2EP2).

S-RPV-017 is derived from S-RPV-000 (ATCC Strain VR-838). This is accomplished utilizing the HOMOLOGY VECTOR 938-94.1 (see Materials and Methods) and virus S-RPV-000 in the HOMOLOGOUS RECOMBINATION PROCEDURE FOR GENERATING RECOMBINANT RPV. The transfection stock is screened by the SCREEN FOR RECOMBINANT RPV EXPRESSING β-glucuronidase (X-GLUC™ ASSAYS). The final result of blue plaque purification is the recombinant virus designated S-RPV-017. This virus is assayed for β-glucuronidase expression, purity, and insert stability by multiple passages monitored by the blue plaque assay as described in Materials and Methods. After the initial three rounds of purification, all plaques observed were blue indicating that the virus is pure, stable, and expressing the foreign gene.

S-RPV-017 is assayed for expression of PRRS-specific antigens using the BLACK PLAQUE SCREEN FOR FOREIGN GENE EXPRESSION IN RECOMBINANT RPV. Rabbit polyclonal anti β-glucuronidase antibody is shown to react specifically with S-RPV-017 plaques and not with S-RPV-000 negative control plaques.

S-RPV-017 is useful as a vaccine in swine against PRRS infection. S-RPV-017 is useful as a vaccine in combination with S-RPV-015, S-RPV-016, S-RPV-018, S-RPV-019, and S-RPV-020 which express PRRS ORF2, ORF3, ORF5, ORF6 and ORF7, respectively. S-RPV-017 is also useful for expression of the PRRS ORF4 protein for purposes of raising antibodies to PRRS ORF4 and for diagnostic assays.

EXAMPLE 19

S-RPV-018

S-RPV-018 is a raccoonpox virus (RPV) that expresses at least two foreign genes. The gene for E. coli β-glucuronidase (uidA) and the gene for porcine reproductive and respiratory syndrome virus (PRRS) ORF5 (Eichelberger strain) are inserted into the RPV O1L ORF (a unique NotI restriction site has replaced an XbaI restriction site) within the RPV HindIII "U" genomic fragment. The uidA gene is under the control of the synthetic late promoter (LP1), and the PRRS ORF5 gene is under the control of the synthetic early promoter (EP2).

S-RPV-018 is derived from S-RPV-000 (ATCC Strain VR-838). This is accomplished utilizing the HOMOLOGY VECTOR 938-94.25 (see Materials and Methods) and virus S-RPV-000 in the HOMOLOGOUS RECOMBINATION PROCEDURE FOR GENERATING RECOMBINANT RPV. The transfection stock is screened by the SCREEN FOR RECOMBINANT RPV EXPRESSING β-glucuronidase (X-GLUC™ ASSAYS). The final result of blue plaque purification is the recombinant virus designated S-RPV-018. This virus is assayed for β-glucuronidase expression, purity, and insert stability by multiple passages monitored by the blue plaque assay as described in Materials and Methods. After the initial three rounds of purification, all plaques observed were blue indicating that the virus is pure, stable, and expressing the foreign gene.

S-RPV-018 is assayed for expression of PRRS-specific antigens using the BLACK PLAQUE SCREEN FOR FOREIGN GENE EXPRESSION IN RECOMBINANT RPV. Rabbit polyclonal anti β-glucuronidase antibody is shown to react specifically with S-RPV-018 plaques and not with S-RPV-000 negative control plaques.

S-RPV-018 is useful as a vaccine in swine against PRRS infection. S-RPV-018 is useful as a vaccine in combination with S-RPV-015, S-RPV-016, S-RPV-017, S-RPV-019, and S-RPV-020 which express PRRS ORF2, ORF3, ORF4, ORF6 and ORF7, respectively. S-RPV-018 is also useful for expression of the PRRS ORF5 protein for purposes of raising antibodies to PRRS ORF5 and for diagnostic assays.

EXAMPLE 20

S-RPV-019

S-RPV-019 is a raccoonpox virus (RPV) that expresses at least two foreign genes. The gene for *E. coli* β-glucuronidase (uidA) and the gene for porcine reproductive and respiratory syndrome virus (PRRS) ORF6 (Eichelberger strain) are inserted into the RPV O1L ORF (a unique NotI restriction site has replaced an XbaI restriction site) within the RPV HindIII "U" genomic fragment. The uidA gene is under the control of the synthetic late promoter (LP1), and the PRRS ORF6 gene is under the control of the synthetic late promoter (LP2).

S-RPV-019 is derived from S-RPV-000 (ATCC Strain VR-838). This is accomplished utilizing the HOMOLOGY VECTOR 950-13.4 (see Materials and Methods) and virus S-RPV-000 in the HOMOLOGOUS RECOMBINATION PROCEDURE FOR GENERATING RECOMBINANT RPV. The transfection stock is screened by the SCREEN FOR RECOMBINANT RPV EXPRESSING β-glucuronidase (X-GLUC™ ASSAYS). The final result of blue plaque purification is the recombinant virus designated S-RPV-019. This virus is assayed for β-glucuronidase expression, purity, and insert stability by multiple passages monitored by the blue plaque assay as described in Materials and Methods. After the initial three rounds of purification, all plaques observed are blue indicating that the virus is expressing the foreign gene.

S-RPV-019 is useful as a vaccine in swine against PRRS infection. S-RPV-019 is useful as a vaccine in combination with S-RPV-015, S-RPV-016, S-RPV-017, S-RPV-018, and S-RPV-020 which express PRRS ORF2, ORF3, ORF4, ORF5 and ORF7, respectively. S-RPV-019 is also useful for expression of the PRRS ORF6 protein for purposes of raising antibodies to PRRS ORF6 and for diagnostic assays.

EXAMPLE 21

S-RPV-020

S-RPV-020 is a raccoonpox virus (RPV) that expresses at least two foreign genes. The gene for *E. coli* β-glucuronidase (uidA) and the gene for porcine reproductive and respiratory syndrome virus (PRRS) ORF7 (Eichelberger strain) are inserted into the RPV O1L ORF (a unique NotI restriction site has replaced an XbaI restriction site) within the RPV HindIII "U" genomic fragment. The uida gene is under the control of the synthetic late promoter (LP1), and the PRRS ORF7 gene is under the control of the synthetic early promoter (EP2).

S-RPV-020 is derived from S-RPV-000 (ATCC Strain VR-838). This is accomplished utilizing the HOMOLOGY VECTOR 936-87.2 (see Materials and Methods) and virus S-RPV-000 in the HOMOLOGOUS RECOMBINATION PROCEDURE FOR GENERATING RECOMBINANT RPV. The transfection stock is screened by the SCREEN FOR RECOMBINANT RPV EXPRESSING β-glucuronidase (X-GLUC™ ASSAYS). The final result of blue plaque purification is the recombinant virus designated S-RPV-020. This virus is assayed for β-glucuronidase expression, purity, and insert stability by multiple passages monitored by the blue plaque assay as described in Materials and Methods.

After the initial three rounds of purification, all plaques observed were blue indicating that the virus is pure, stable, and expressing the foreign gene.

S-RPV-020 is assayed for expression of PRRS-specific antigens using the BLACK PLAQUE SCREEN FOR FOREIGN GENE EXPRESSION IN RECOMBINANT RPV. Rabbit polyclonal anti β-glucuronidase antibody is shown to react specifically with S-RPV-020 plaques and not with S-RPV-000 negative control plaques.

S-RPV-020 is useful as a vaccine in swine against PRRS infection. S-RPV-020 is useful as a vaccine in combination with S-RPV-015, S-RPV-016, S-RPV-017, S-RPV-018, and S-RPV-019 which express PRRS ORF2, ORF3, ORF4, ORF5 and ORF6, respectively. S-RPV-020 is also useful for expression of the PRRS ORF7 protein for purposes of raising antibodies to PRRS ORF7 and for diagnostic assays.

EXAMPLE 22

S-RPV-028

S-RPV-028 is a raccoonpox virus (RPV) that expresses at least three foreign genes. The gene for *E. coli* β-glucuronidase (uidA) and the genes for porcine reproductive and respiratory syndrome virus (PRRS) ORF5 and ORF6 (Eichelberger strain) are inserted into the RPV O1L ORF (a unique NotI restriction site has replaced an XbaI restriction site) within the RPV HindIII "U" genomic fragment. The uida gene is under the control of the synthetic late promoter (LP1), the PRRS ORF5 gene is under the control of the synthetic early promoter (EP2) and the PRRS ORF6 gene is under the control of the synthetic late promoter (LP1).

S-RPV-028 is derived from S-RPV-000 (ATCC Strain VR-838). This is accomplished utilizing the HOMOLOGY VECTOR 950-16.34 (see Materials and Methods) and virus S-RPV-000 in the HOMOLOGOUS RECOMBINATION PROCEDURE FOR GENERATING RECOMBINANT RPV. The transfection stock is screened by the SCREEN FOR RECOMBINANT RPV EXPRESSING β-glucuronidase (X-GLUC™ ASSAYS). The final result of blue plaque purification is the recombinant virus designated S-RPV-028. This virus is assayed for β-glucuronidase expression, purity, and insert stability by multiple passages monitored by the blue plaque assay as described in Materials and Methods. After the initial three rounds of purification, all plaques observed were blue indicating that the virus is pure, stable, and expressing the foreign gene.

S-RPV-028 is assayed for expression of PRRS-specific antigens using the BLACK PLAQUE SCREEN FOR FOREIGN GENE EXPRESSION IN RECOMBINANT RPV. Rabbit polyclonal anti β-glucuronidase antibody is shown to react specifically with S-RPV-020 plaques and not with S-RPV-000 negative control plaques.

S-RPV-028 is useful as a vaccine in swine against PRRS infection. S-RPV-028 is useful as a vaccine in combination with S-RPV-015, S-RPV-016, S-RPV-017, which express PRRS ORF2, ORF3, and ORF4, respectively. S-RPV-028 is also useful for expression of the PRRS ORF5 and ORF6 proteins for purposes of raising antibodies to PRRS ORF5 and ORF6 and for diagnostic assays.

EXAMPLE 23

Expression of the RPV K1L or C7L Genes in Recombinant Swinepox Virus to Broaden the Host Range of Recombinant Swinepox Virus The K1L gene in vaccinia virus determines the range of replication of the virus in the animal host. Deletion of this gene in vaccinia virus restricts viral replication in the host animal. Sequencing of the near terminal region of the swinepox virus genome indicates that the K1L gene is not present in this region and may be absent in the swinepox virus genome. (26). The K1L homologue in raccoonpox virus is located within the HindIII "T" RPV genomic fragment (SEQ ID NO. 5 and 10). The host range of raccoonpox is broader than swinepox virus (which replicates mainly in swine); Raccoonpox host range includes raccoons, dogs, cats, swine, cattle, monkeys and other mammals (See Table 1). A recombinant swinepox virus comprising the RPV K1L ORF under the control of the synthetic pox promoter, K1L promoter or LP2EP2 (or LP1 or LP2 or EP1 or EP2), has a broader host range to include raccoons, dogs, cats, and other mammals. Preferably, the promoter is the K1L promoter from raccoonpox which will express the K1L protein at the correct stage of the viral life cycle. A modified host range recombinant swinepox virus, which also expresses foreign DNA coding for an antigen from a disease pathogen, is an improved vaccine in raccoons, dogs, cats, and other mammals since it will replicate in the animals, expressing the foreign DNA and elicit a strong immune response against the antigen from the disease pathogen. The modified host range recombinant swinepox virus does not cause disease in the vaccinated animal.

In an alternative embodiment, recombinant swinepox virus comprising the RPV C7L ORF (host range gene) under the control of the synthetic pox promoter, C7L promoter or LP2EP2 (or LP1 or LP2 or EP1 or EP2), has a broader host range to include raccoons, dogs, cats, and other mammals. Preferably, the promoter is the C7L promoter from raccoonpox which will express the C7L protein at the correct stage of the viral life cycle. A modified host range recombinant swinepox virus, which also expresses foreign DNA coding for an antigen from a disease pathogen, is an improved vaccine in raccoons, dogs, cats, and other mammals since it will replicate in the animals, expressing the foreign DNA and elicit a strong immune response against the antigen from the disease pathogen. The modified host range recombinant swinepox virus does not cause disease in the vaccinated animal.

S-SPV-248:

S-SPV-248 is a swinepox virus (SPV) that expresses at least two foreign genes. The gene for raccoonpox virus K1L host range is inserted into a unique NotI restriction site located distal to the E. Coli β-galactosidase (lacZ) gene contained in a plasmid homology vector which deletes the swinepox virus I4L and I5L genes. The lacZ gene is under the control of the swinepox I5L and the K1L gene is under control of the raccoonpox virus K1L promoter.

SPV-248 is derived from S-SPV-001 (Kasza Strain). This was accomplished utilizing a homology vector and virus S-SPV-001 in the HOMOLOGOUS RECOMBINATION PROCEDURE FOR GENERATING RECOMBINANT SPV. The transfection stock is screened using the SCREEN FOR RECOMBINANT SPV EXPRESSING β-galactosidase (SCREEN FOR RECOMBINANT HERPESVIRUS EXPRESSING ENZYMATIC MARKER GENES). The final result of blue plaque purification is the recombinant virus designated S-SPV-248. This virus is assayed for β-galactosidase expression, purity, and insert stability by multiple passages monitored by the blue plaque assay as described in Materials and Methods.

S-SPV-248 is useful as a vaccine against disease in mammals. S-SPV-248 has a broader host range than other recombinant SPV due to expression of the RPV K1L gene. The host range includes, but is not limited to, raccoons, dogs, cats, horses, cows, sheep, goats, and other mammals. S-SPV-248 is also useful as a vaccine in avian species.

S-SPV-249:

S-SPV-249 is a swinepox virus (SPV) that expresses at least two foreign genes. The gene for raccoonpox virus C7L host range is inserted into a unique NotI restriction site located distal to the E. Coli β-galactosidase (lacZ) gene contained in a plasmid homology vector which deletes the swinepox virus I4L and I5L genes. The lacZ gene is under the control of the swinepox I5L promoter and the C7L gene is under the control of the raccoonpox virus C7L promoter.

SPV-249 is derived from S-SPV-001 (Kasza Strain). This was accomplished utilizing a homology vector and virus S-SPV-001 in the HOMOLOGOUS RECOMBINATION PROCEDURE FOR GENERATING SPV. The transfection stock is screened using the SCREEN FOR RECOMBINANT SPV EXPRESSING β-galactosidase (SCREEN FOR RECOMBINANT HERPESVIRUS EXPRESSING ENZYMATIC MARKER GENES). The final result of blue plaque purification is the recombinant virus designated S-SPV-249. This virus is assayed for β-galactosidase expression, purity, and insert stability by multiple passages monitored by the blue plaque assay as described in Material and Methods.

S-SPV-249 is useful as a vaccine against disease in mammals. S-SPV-249 has a broader host range than other recombinant SPV due to expression of the RPV C7L gene. The host range includes, but is not limited to, raccoons, dogs, cats, horses, cows, sheep, goats and other mammals. S-SPV-249 is also useful as a vaccine in avian species.

Deletion of Host Range Genes from Recombinant Raccoonpox Virus:

In a further embodiment, deletion of the host range genes selected from the group consisting of C7L, C6L, C5L, C4L, C3L, C2L, C1L, N1L, N2L, M1L, M2L, and K1L ("C7L to K1L") in a raccoonpox virus vector results in limited replication of the recombinant raccoonpox in Vero cells and no replication in other cell types, such as CRFK or MDCK cells. The recombinant raccoonpox with a deletion of some or all of the C7L to K1L host range genes is useful as a vaccine which is safe and less virulent than recombinant raccoonpox containing the C7L to K1L genes. To select for recombinant raccoonpox expressing a foreign DNA of interest, a homology vector containing some or all of the host range genes C7L to K1L and a foreign gene of interest under the control of a promoter is combined with recombinant raccoonpox virus deleted for the C7L to K1L genes in the HOMOLOGOUS RECOMBINATION PROCEDURE FOR GENERATING RECOMBINANT RPV and selected for growth in cell types other than Vero cells, such as CRFK or MDCK cells. Any recombinant virus which grows in the other cell types must contain the host range genes C7L to K1L and the foreign gene of interest.

TABLE 1

| Virus | ESK-4 (Porcine) | PKWRL (Porcine) | VERO (Monkey) | CRFK (Feline) | MDCK (Canine) | MDBK (Bovine) |
|---|---|---|---|---|---|---|
| Raccoon pox virus | + | + | +++ | +++ | +++ | +/- |
| Swinepox virus | +++ | +++ | +++ | – | – | – |
| Vaccinia virus | +++ | ND | +++ | +++ | +++ | +++ |
| Swinepox virus with RcnPV K1L gene | +++ | +++ | +++ | +++ | +++ | +/- |

+++ Extensive CPE
– No CPE
ND Not Determined

Figure 2:
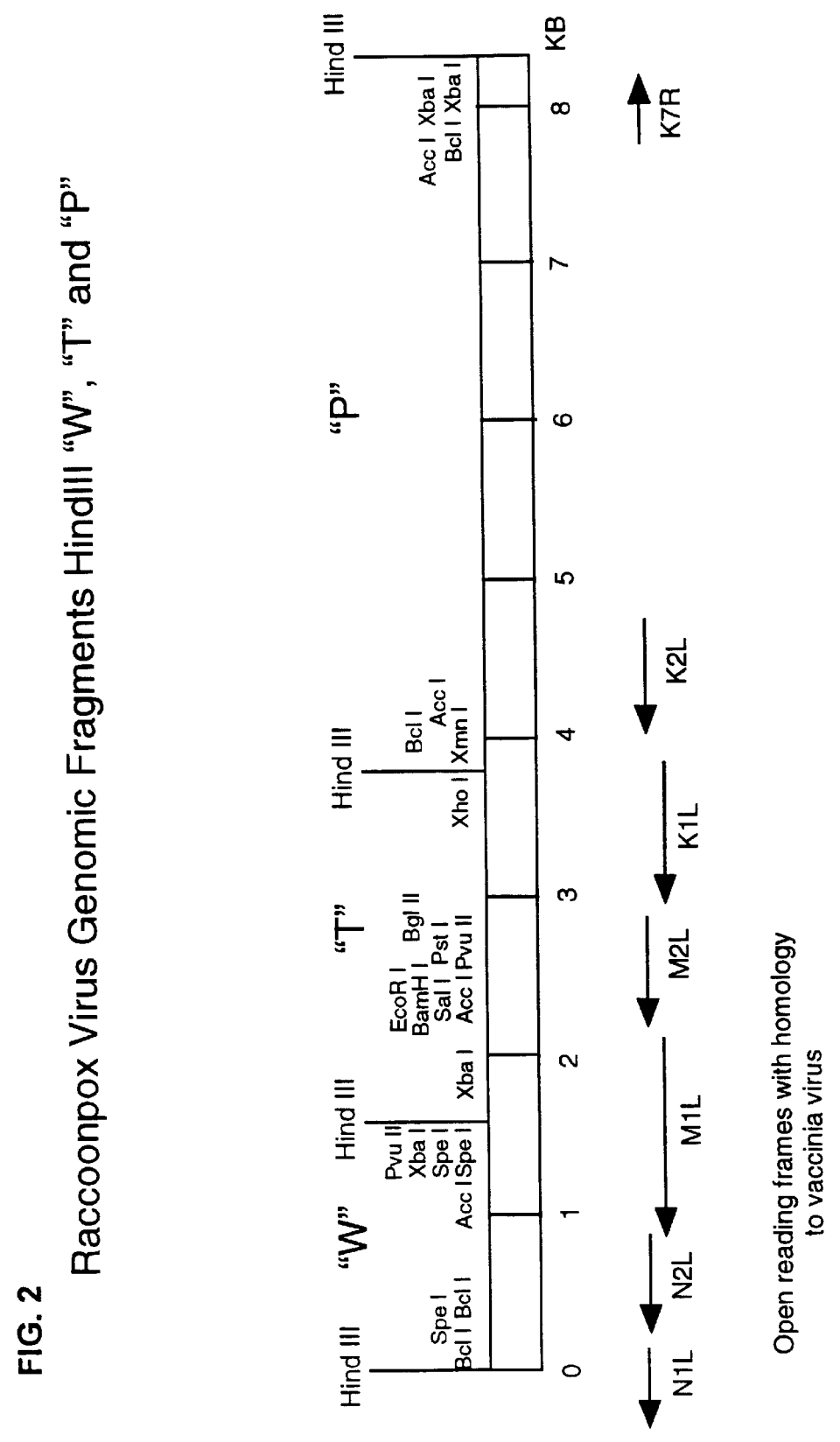

EXAMPLE 24
Nonessential Regions in RPV Genomic Fragments W, T, and P for Insertion of Foreign DNA into a Recombinant Raccoonpox Virus Nonessential insertion regions in RPV genomic fragments W, T, and P are useful for constructing recombinant raccoonpox viruses expressing foreign DNA which is inserted into a genomic region of the recombinant RPV. RPV genomic fragments W, T, and P contain open reading frames for vaccinia virus homologues N1L, N2L, M1L, M2L, K1L, K2L, and K7R. (SEQ ID NO. 5–13) (17) These are all nonessential genes and are useful for insertion of foreign DNA to produce a recombinant raccoonpox virus. Intergenic regions between the ORFs are also useful for insertion of foreign DNA. Some of the restriction sites which are useful for insertion of foreign DNA in this region are shown in FIG. 2. Preferred insertion sites for foreign DNA in the HindIII W genomic fragment are Bcl I, Acc I, Pvu II, and Xba I; Preferred insertion sites for foreign DNA in the HindIII T genomic fragment are EcoR I, BamH I, Sal I, Bgl II, Pst I, Acc I, Pvu II, Xho I, and Xba I; Preferred insertion sites for foreign DNA in the HindIII P genomic fragment are Bcl I, Acc I, Xmn I and Xba I.

N1L is a virulence gene (virokine); K1L is a host range gene. It is important for use in swinepox virus vector to broaden the host range of SPV; K2L is a serine protease inhibitor (SPI-3); K3L is a translation initiation factor; confers interferon resistance; K4L is a member of the phospholipase D superfamily.

Figure 8:
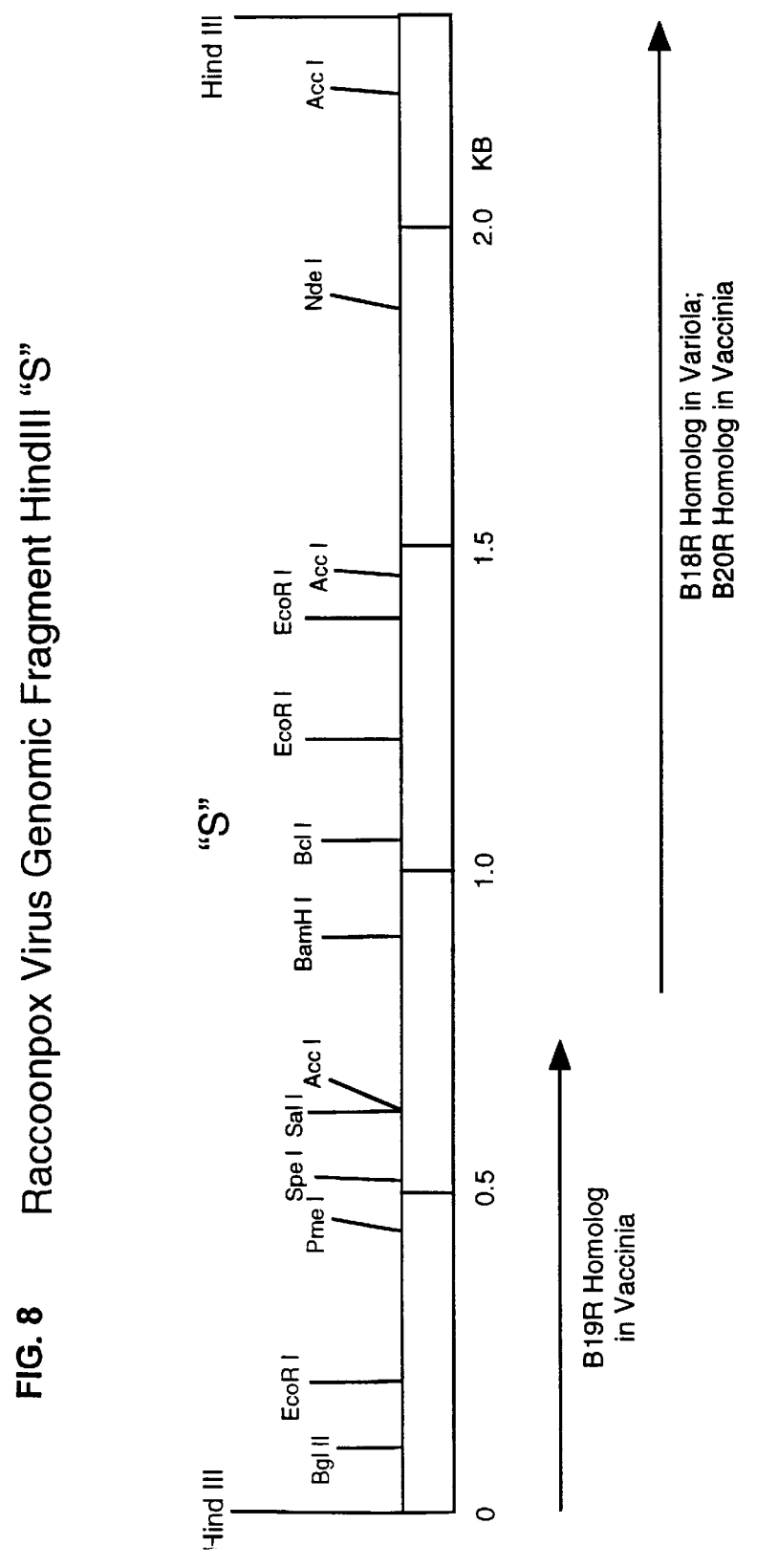

EXAMPLE 25
Nonessential Regions in RPV Genomic Fragment S for Insertion of Foreign DNA into a Recombinant Raccoonpox Virus Nonessential insertion regions in RPV genomic fragment S are useful for constructing recombinant raccoonpox viruses expressing foreign DNA which is inserted into a genomic region of the recombinant RPV. RPV genomic fragment S contains open reading frames for vaccinia virus homologues B19R, B20R and variola B18R. (SEQ ID NO. 33 to 35) (27). Amino acids 7 to 523 of SEQ ID NO 35 has homology to variola virus B18R ORF. Amino acids 235 to 399 has homology to vaccinia virus B20R ORF. These are all nonessential genes and are useful for insertion of foreign DNA to produce a recombinant raccoonpox virus. Intergenic regions between the ORFs are also useful for insertion of foreign DNA. Some of the restriction sites which are useful for insertion of foreign DNA in this region are shown in FIG. 8. Preferred insertion sites for foreign DNA in the HindIII S genomic fragment are Bgl II, EcoR I, Pme I, Spe I, Sal I, Acc I, BamH I, Bcl I, and Nde I.

Vaccinia B19R is a surface antigen present on infected cells. Vaccinia B20R and Variola B18R are homologous to neuraxin protein and map 1B protein (25).

EXAMPLE 26
Mapping of Raccoonpox Virus Genomic Fragments HindIII M and HindIII R Restriction endonuclease mapping and DNA sequencing of the raccoonpox virus genome indicates differences in the HindIII restriction map compared to the published HindIII restriction map. In the present invention, the size of the HindIII M genomic region of RPV is 6.0 kb. The previously published size of the HindIII M genomic region of RPV is 5.4 kb (5). In the present invention, the HindIII J and HindIII W genomic fragments of RPV are immediately adjacent. An earlier published HindIII restriction map of the RPV genome shows HindIII R genomic fragment between HindIII J and HindIII W genomic fragments (6).

EXAMPLE 27
Raccoonpox Virus E11L Promoter

Figure 7:
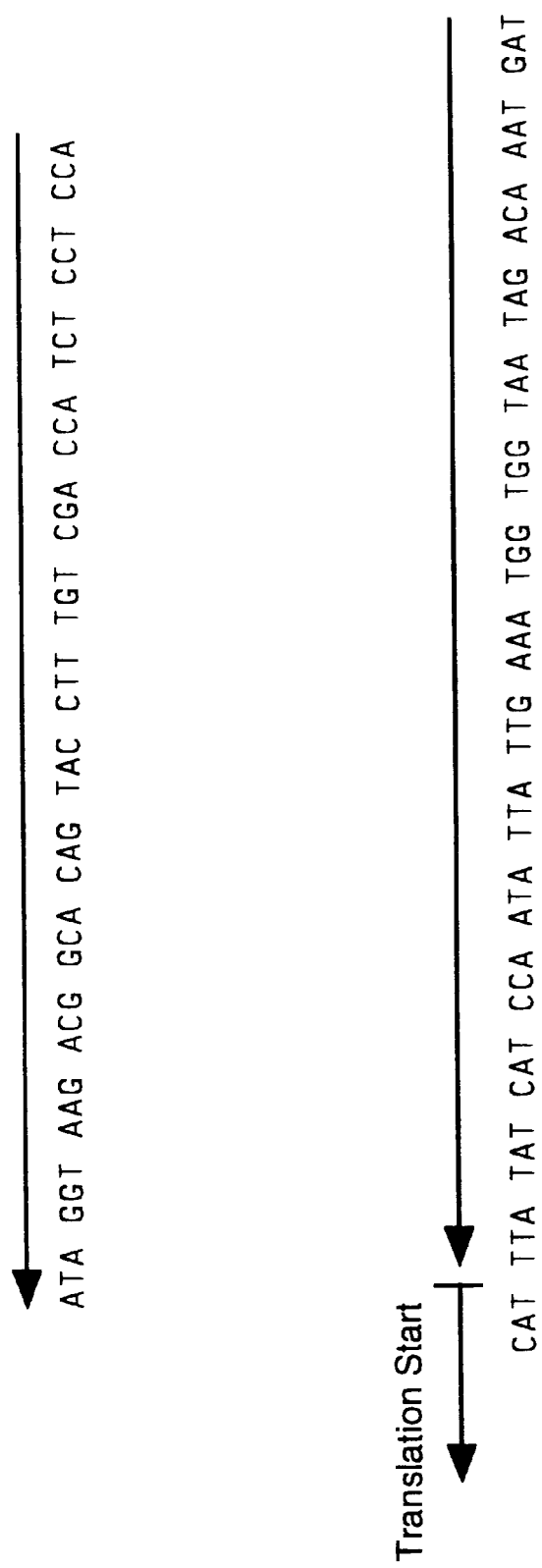
FIG. 7: DNA sequence of the raccoonpox virus E11L promoter and location of the translation start codon. Direction of transcription is from right to left. (SEQ ID NO. 30) The raccoonpox virus E11L promoter is useful for expression of foreign DNA in recombinant poxvirus vectors, including, but not limited to raccoonpox, swinepox, avipox, fowlpox, canarypox, cowpox, capripox, and vaccinia virus.

The raccoonpox virus E11L promoter is useful as a homologous promoter in raccoonpox or a heterologous promoter in other poxviruses for the expression of foreign DNA in a recombinant poxvirus (FIG. 7; SEQ ID NO: 30). Other poxviruses include, but are not limited to, swinepox, fowlpox, avipox, canarypox, cowpox and vaccinia virus.

EXAMPLE 28
Swinepox Virus I5L Promoter

The swinepox virus (SPV) I5L promoter is useful as a homologous promoter in swinepox or a heterologous promoter in other poxviruses for the expression of foreign DNA in a recombinant poxvirus (FIG. 9; SEQ ID NO: 55). Other poxviruses include, but are not limited to, raccoonpox, fowlpox, avipox, canarypox, cowpox and vaccinia virus. The SPV I5L promoter is contained within the SPV HindIII N genomic fragment. The SPV I5L promoter is a strong late promoter.

References

1. Herman, J. F., (1964), *Bacteriol. Proc.* 64th Annual Meeting Amer. Soc. Microbiol, p. 117.
2. Alexander, A. D., et al., (1975), *J. Wildl. Dis.* 8, 119.
3. Thomas, E. K., et al., (1975), *Archives of Virology* 49, 217–227.
4. Esposito and Knight, (1985), *Virology* 143, 230–251.
5. Parsons, B. L. and Pickup, D. J. (1987), *Virology* 161, 45–53.
6. Knight, J. C., et al., (1992), *Virology* 190, 423–433.
7. Cavallaro, K. F., et al., (1992), *Virology* 190, 434–439.
8. Esposito, J. J., et al., (1989), *Vaccines* 89: Modern approaches to new vaccines including the prevention of AIDS (ed. R. Chanock et al.), p. 403. Cold Spring Harbor Laboratory Press, New York.
9. DeMartini, J. C., et al., (1993), *Archives of Virology* 133, 211–222.
10. Lodmell, D. L., (1991), *Journal of Virology* 65, 3400–3405.

11. Esposito J. J., et al. (1992), *Vaccines* 92, pp.321–329, Cold Spring Harbor Laboratory Press.
12. U.S. Pat. No. 5,266,313, J. J. Esposito and G. M. Baer, USA/Dept HHS.
13. PCT International application WO 93/01284, F. W Scott and Ngichabe, C. K., Cornell Research Foundation.
14. European application number EP 652 287 A2, Wasmoen, T. et al., American Home Products Corporation
15. Hakes, D. J., et al., (1993) *Proc. Natl. Acad. Sci. USA* 90, 4017–4021.
16. Lutze-Wallace, C., et al., (1995), *Virus Genes*, 10, 81–84.
17. Massung, et al. (1993), *Nature* 366 (6457), 748–751.
18. Safronov, et al. (1996), *Dokl. Akad. Nauk* 349 (6), 829–833.
19. U. K. Laemnli, (1970), *Nature* 227, 680–685.
20. J. Sambrook, et al., *Molecular Cloning: A Laboratory Manual, Second Edition*, Cold Spring Harbor Press, Cold Spring Harbor, N.Y. (1989).
21. *Current Protocols in Molecular Biology* (E's. Affable, Brent, Kingston, More, Footman, Smith and Stuhl, Greene Publ. Assoc., Wiley-Interscience, New York, N.Y., 1992).
22. M. A. Innis, et al., *PCR Protocols: A Guide to Methods and Applications*, Academic Press, Inc., San Diego (1990).
23. M. W. Mellencamp, et al., *Journal of Clinical Microbiology*, volume 27, pp. 2208–2213 (1989)
24. L. A. Herzenberg, et al., *Selected Methods in Cellular Immunology*, Freeman Publ. Co., San Francisco, 351–372 (1980).
25. F. A. Ferrari, et al., *Journal of Bacteriology* (1985) 161, 556–562.
26. Massung, et al., Virology (1993) 197: 511–528
27. Perkus, et al., (1991) *Virology* 180, 406–410

What is claimed is:

1. A recombinant raccoonpox virus comprising a raccoonpox virus viral genome which contains a foreign DNA sequence inserted into a non-essential region within the HindIII "U" genomic region (SEQ ID NO:1) of the raccoonpox virus genome.

2. The recombinant raccoonpox virus of claim 1, wherein the foreign DNA sequence is inserted into an O1L open reading frame (SEQ ID NO:3).

3. The recombinant raccoonpox virus of claim 1, wherein the foreign DNA sequence is inserted into an E11L open reading frame (SEQ ID NO:2).

4. The recombinant raccoonpox virus of claim 1, wherein the foreign DNA sequence is inserted into an intergenic region.

5. The recombinant raccoonpox virus of claim 2, wherein the foreign DNA sequence is inserted into an XbaI restriction endonuclease site.

6. The recombinant raccoonpox virus of claim 1, which further comprises the foreign DNA sequence inserted into the HindIII "U" genomic region, wherein the foreign DNA is capable of being expressed in a recombinant raccoonpox virus host cell.

7. The recombinant raccoonpox virus of claim 1, wherein the foreign DNA sequence encodes a screenable marker.

8. The recombinant raccoonpox virus of claim 7, wherein the screenable marker is *E. coli* beta-galactosidase.

9. The recombinant raccoonpox virus of claim 7, wherein the screenable marker is *E. coli* beta-glucuronidase.

10. The recombinant raccoonpox virus of claim 1, wherein the foreign DNA sequence encodes an antigenic polypeptide.

11. The recombinant raccoonpox virus of claim 10, wherein the antigenic polypeptide when introduced into the host cell, induces production of antibodies against a feline disease-causing agent from which the antigenic polypeptide is derived or derivable.

12. The recombinant raccoonpox virus of claim 11, wherein the antigenic polypeptide is derived or derivable from a group consisting of feline pathogen, canine pathogen, equine pathogen, bovine pathogen, caprine pathogen, avian pathogen, porcine pathogen, or human pathogen.

13. The recombinant raccoonpox virus of claim 1, wherein the foreign DNA sequence is selected from a group consisting of swine influenza virus hemagglutinin, swine influenza virus neuraminidase, porcine reproductive and respiratory virus (PRRS) ORF2, PRRS ORF3, PRRS ORF4, PRRS ORF5, PRRS ORF6, PRRS ORF7, porcine parvovirus VP2.

14. The recombinant raccoonpox virus of claim 1, wherein the foreign gene is under control of an endogenous upstream, raccoonpox virus promoter.

15. The recombinant raccoonpox virus of claim 14, wherein the promoter is selected from a group consisting of the raccoonpox virus E11L promoter and the raccoonpox virus O1L promoter.

16. The recombinant raccoonpox virus of claim 1, wherein the foreign gene is under control of a heterologous upstream promoter.

17. The recombinant raccoonpox virus of claim 16, wherein the promoter is selected from a group consisting of the synthetic pox late promoter 1 (LP1), the synthetic pox early promoter 1 (EP1), the synthetic pox early promoter 2 (EP2), the synthetic pox late promoter 2 early promoter 2 (LP2EP2), the synthetic pox late promoter 1 (LP1), the synthetic pox late promoter 2 (LP2), and the swinepox virus I5L promoter.

18. The recombinant raccoonpox virus of claim 1 designated S-RPV-002.

19. A host cell infected with the recombinant raccoonpox virus of claim 1.

20. A host cell of claim 19, wherein the host cell is mammalian cell.

21. An immunological composition against an animal pathogen which comprises an effective immunizing amount of the recombinant raccoonpox virus of claim 1 and a suitable carrier.

22. A method of immunizing an animal against an animal pathogen which comprises administering to the animal an effective immunizing dose of the immunological composition of claim 21.

23. A method of immunizing an animal against a feline pathogen which comprises administering to the animal an effective immunizing dose of the immunological composition of claim 21.

24. The recombinant raccoonpox virus of claim 1, wherein the foreign DNA sequence is inserted into an intergenic region. claim 21.

* * * * *

SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
      (A) LENGTH: 2061 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Raccoonpox virus ATCC# VR-838

(ix) FEATURE:
      (A) NAME/KEY: CDS
      (B) LOCATION: 386..1

(ix) FEATURE:
      (A) NAME/KEY: CDS
      (B) LOCATION: 2061..372

(xi) SEQUENCE DESCRIPTION: SEQ ID NO:1:

```
AAGCTTAATC CATCATAAAA TTTATGGTTA GTAACGACTG AAATAACTGC GTAATCATTT      60

TTTGGTACAA TTCTAGTCGG CATAGATTCT GTAACAATGA ATTCGATTCC CGTTACTTTA     120

GTAAAATCTT TTACAAATAA CAAGGATTCA TCAAATACGT AAAACTCATT ATTTACTATA     180

GAAATTGATC CCCTATCACA CTTGAAATAA AAAATATCTT TATCCTTTAA CACCAAATAA     240

AATTCAGATT GGTCAATATG AATGTATTCA CTTAGTAATT CAACGAACTT ATTTATTAAT     300

TCTGATACAC ACACTGATTC TGTATTGTTT ATCGAAAACT TTACTCTTCC TGTATCAGTT     360

TCTAAAAAAA TATTAACAAG TTCCATTTAT ATCATCCAAT ATTATTGAAA TGGTGGTAAT     420

AGACAAATGA TATAGGTAAG ACGGCACAGT ACCTTTGTCG ACCATCTCCT CCATTTCATG     480

CTCTATCTTA TCATGAACTT TGATATGTGA AAACAATACA CCACATGCTT CTATAACAGT     540

ATGTAACACT TTAGATACAA AATGCTTGAT ACCATCGTAA TTGTTCAACA CGGCCAATCT     600
```

-continued

```
ATAATAGATA GTAGCTACTA TATATTCTAT GATAGTATTG AAGAAGATAA CCACCTTGGC    660

ATATTGGTCA TTTAATACAG ACATGGTATC AACAGATAGC TTAAACGATA GGGAATCCGT    720

GAATGGAATA AGCGTTTCAT TGATTGAATA TCCATATACT AACATATCGG ATATCCTGAT    780

GTGTTCCATT AAATCGTTAA GTTTTTTCTT TTTAACCTCG TTGAACATCA TTTCTGTTAA    840

CGGTCCCCAA CATCTTTGAC CAATTAATTT TTGATTTATT TTTCCATGTA TGGCGTATCT    900

AGTCAGGTCG TATAACCTAT CCAATAATCC ATCATCGGTA TCCAAATTAC ATACTATGCT    960

TTTCAATTCT CTATAGAAAA GATTAATACA TCTAGAACAA CAACATGATG TAATATCTTT   1020

ATCATCAACA GATGTGATAT ATTTGAAGAT TTTTCTATGA TAATGAAGAA TTTTTGAGAA   1080

TACTGTATTA ATGGTGTCTG TTACCATGAT CCCTTTGATT GCTGACAGAG TCAGCGAGCA   1140

TGATTTCCAA TCTTTAACAA TTTTTATTAC CATTATCTTT GTTTTAATGT CTATAGATGA   1200

TAACATAACA CGTCTAACAA TACACGGATT AAGACGGAAA GATGAAATTA TTCTTTCAAC   1260

ATCTCCAATG GATAACTTAC TATTTCGACG TGCATTGTCT ATATGCTCGA GAACATCCTC   1320

CAACGAGTCT GTATCTTTTT TGATTATCGT CGATCTCAAC GATTTGGGTC GTCTAGATCG   1380

TCGGACTCTA TCACCAGATG GCATAGTTAT TAGTCTTCTT TCTGTTTTCA TAATGAAATT   1440

TCTAAATTCA TCTGCGAATC TTCTATATCT AAAATCATAA TATGCGATAT TTGTTTCAAC   1500

AAATTTCCGT TCGTCCAATG TCAACATATC TATCTCGGTT TCATACCCTA AATTGAACAT   1560

GGCTACGGAT TTAATTTTAT ATTCATCTAT CAACTCTTCT TCAACAATAA CAGAGTATAG   1620

ATAATCATTT AATCCATCAT ACATAGTAGG AAGATTCTCG TTAACAAATT GTTTAACTGC   1680

ACTGATAAAA CTGGGACTAT ATTTGATATC TTGTCTAATA AAATTAATAA CATTGTCCAA   1740

AGGATACTTT TTAACTAGAT TTATACATAT CTGTTCATCA GTGAGGTTAT GCAAAACATC   1800

GTGAATAGGT GGCACATTAT ATTCATCAGA TATACTAATA ACAATTTCCA GATCTATATT   1860

GTTTAATATA TTATATAGAT GGAGCACGGA TCCAACGGGG ATCTCTTTAA CCACATCACG   1920

GATTTCATCA ACTGTTAAAT CTATTTTAAA GTTAATCATG TACGCGTTAA TTTTTAAAAG   1980

ATGTGTGGCT CTAACTATAT TCTCACGAAT TAGCCATTCC AAGTCACTAC GTGAGAGAAG   2040

ATCGTATTCT ATCATAAGCT T                                            2061
```

(2) INFORMATION FOR SEQ ID NO:2:

(i) SEQUENCE CHARACTERISTICS:
        (A) LENGTH: 128 amino acids
        (B) TYPE: amino acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

```
Met Glu Leu Val Asn Ile Phe Leu Glu Thr Asp Thr Gly Arg Val Lys
 1               5                  10                  15

Phe Ser Ile Asn Asn Thr Glu Ser Val Cys Val Ser Glu Leu Ile Asn
            20                  25                  30

Lys Phe Val Glu Leu Leu Ser Glu Tyr Ile His Ile Asp Gln Ser Glu
        35                  40                  45

Phe Tyr Leu Val Leu Lys Asp Lys Asp Ile Phe Tyr Phe Lys Cys Asp
    50                  55                  60
```

-continued

Arg Gly Ser Ile Ser Ile Val Asn Asn Glu Phe Tyr Val Phe Asp Glu
65                  70                  75                  80

Ser Leu Leu Phe Val Lys Asp Phe Thr Lys Val Thr Gly Ile Glu Phe
                85                  90                  95

Ile Val Thr Glu Ser Met Pro Thr Arg Ile Val Pro Lys Asn Asp Tyr
            100                 105                 110

Ala Val Ile Ser Val Val Thr Asn His Lys Phe Tyr Asp Gly Leu Ser
            115                 120                 125

(2) INFORMATION FOR SEQ ID NO:3:

(i) SEQUENCE CHARACTERISTICS:
        (A) LENGTH: 688 amino acids
        (B) TYPE: amino acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

Trp Pro Cys Ser Ser Phe Lys Asx Met Gln Lys Asp Glx Leu Asp His
1               5                   10                  15

Met Pro Ser Thr Cys Glx Val Gln Lys Lys Xaa Val Glu Pro Pro Phe
            20                  25                  30

Trp Leu Gln Tyr Asp Pro Gln Lys His Thr Phe Trp Pro Glu His
            35                  40                  45

Thr Glx Leu Ala Ser Thr Gln Glu Ser His Ala His Val Ser Val Lys
    50                  55                  60

Xaa Cys Cys Thr Trp His Thr Asp Asn Ser Ala Asn Tyr His Gly Phe
65                  70                  75                  80

His Glx Glx Arg Ser Ile Val Asx Glu Xaa Asx Pro Trp His Pro Leu
                85                  90                  95

Ala Ser Glu Arg Glu Thr Pro Leu Ser His Pro Leu Ser Pro Arg
            100                 105                 110

Ser Gln Arg Xaa Cys Arg Ile Glu Arg Xaa Leu Cys Arg Xaa Lys Leu
            115                 120                 125

Met Ile Glu Tyr Asp Leu Leu Ser Arg Ser Asp Leu Glu Trp Leu Ile
    130                 135                 140

Arg Glu Asn Ile Val Arg Ala Thr His Leu Leu Lys Ile Asn Ala Tyr
145                 150                 155                 160

Met Ile Asn Phe Lys Ile Asp Leu Thr Val Asp Glu Ile Arg Asp Val
                165                 170                 175

Val Lys Glu Ile Pro Val Gly Ser Val Leu His Leu Tyr Asn Ile Leu
            180                 185                 190

Asn Asn Ile Asp Leu Glu Ile Val Ile Ser Ile Ser Asp Glu Tyr Asn
        195                 200                 205

Val Pro Pro Ile His Asp Val Leu His Asn Leu Thr Asp Glu Gln Ile
        210                 215                 220

Cys Ile Asn Leu Val Lys Lys Tyr Pro Leu Asp Asn Val Ile Asn Phe
225                 230                 235                 240

Ile Arg Gln Asp Ile Lys Tyr Ser Pro Ser Phe Ile Ser Ala Val Lys
                245                 250                 255

Gln Phe Val Asn Glu Asn Leu Pro Thr Met Tyr Asp Gly Leu Asn Asp
            260                 265                 270

-continued

```
Tyr Leu Tyr Ser Val Ile Val Glu Glu Leu Ile Asp Glu Tyr Lys
            275                 280                 285
Ile Lys Ser Val Ala Met Phe Asn Leu Gly Tyr Glu Thr Glu Ile Asp
        290                 295                 300
Met Leu Thr Leu Asp Glu Arg Lys Phe Val Glu Thr Asn Ile Ala Tyr
305                 310                 315                 320
Tyr Asp Phe Arg Tyr Arg Arg Phe Ala Asp Glu Phe Arg Asn Phe Ile
                325                 330                 335
Met Lys Thr Glu Arg Arg Leu Ile Thr Met Pro Ser Gly Asp Arg Val
            340                 345                 350
Arg Arg Ser Arg Arg Pro Lys Ser Leu Arg Ser Thr Ile Ile Lys Lys
        355                 360                 365
Asp Thr Asp Ser Leu Glu Asp Val Leu Glu His Ile Asp Asn Ala Arg
370                 375                 380
Arg Asn Ser Lys Leu Ser Ile Gly Asp Val Glu Arg Ile Ile Ser Ser
385                 390                 395                 400
Phe Arg Leu Asn Pro Cys Ile Val Arg Arg Val Met Leu Ser Ser Ile
                405                 410                 415
Asp Ile Lys Thr Lys Ile Met Val Ile Lys Ile Val Lys Asp Trp Lys
            420                 425                 430
Ser Cys Ser Leu Thr Leu Ser Ala Ile Lys Gly Ile Met Val Thr Asp
        435                 440                 445
Thr Ile Asn Thr Val Phe Ser Lys Ile Leu His Tyr His Arg Lys Ile
    450                 455                 460
Phe Lys Tyr Ile Thr Ser Val Asp Asp Lys Asp Ile Thr Ser Cys Cys
465                 470                 475                 480
Cys Ser Arg Cys Ile Asn Leu Phe Tyr Arg Glu Leu Lys Ser Ile Val
                485                 490                 495
Cys Asn Leu Asp Thr Asp Asp Gly Leu Leu Asp Arg Leu Tyr Asp Leu
            500                 505                 510
Thr Arg Tyr Ala Ile His Gly Lys Ile Asn Gln Lys Leu Ile Gly Gln
        515                 520                 525
Arg Cys Trp Gly Pro Leu Thr Glu Met Met Phe Asn Glu Val Lys Lys
    530                 535                 540
Lys Lys Leu Asn Asp Leu Met Glu His Ile Arg Ile Ser Asp Met Leu
545                 550                 555                 560
Val Tyr Gly Tyr Ser Ile Asn Glu Thr Leu Ile Pro Phe Thr Asp Ser
                565                 570                 575
Leu Ser Phe Lys Leu Ser Val Asp Thr Met Ser Val Leu Asn Asp Gln
            580                 585                 590
Tyr Ala Lys Val Val Ile Phe Phe Asn Thr Ile Ile Glu Tyr Ile Val
        595                 600                 605
Ala Thr Ile Tyr Tyr Arg Leu Ala Val Leu Asn Asn Tyr Asp Gly Ile
    610                 615                 620
Lys His Phe Val Ser Lys Val Leu His Thr Val Ile Glu Ala Cys Gly
625                 630                 635                 640
Val Leu Phe Ser His Ile Lys Val His Asp Lys Ile Glu His Glu Met
                645                 650                 655
Glu Glu Met Val Asp Lys Gly Thr Val Pro Ser Tyr Leu Tyr His Leu
            660                 665                 670
Ser Ile Thr Thr Ile Ser Ile Ile Leu Asp Asp Ile Asn Gly Thr Cys
        675                 680                 685
```

(2) INFORMATION FOR SEQ ID NO:4:

(i) SEQUENCE CHARACTERISTICS:
    (A) LENGTH: 1793 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Raccoonpox virus ATCC# VR-838

(xi) SEQUENCE DESCRIPTION: SEQ ID NO:4:

```
AAGCTTCCCG TTACTTTAGT AAAATCTTTT ACAAATAACA AGGATTCATC AAATACGTAA      60

AACTCATTAT TTACTATAGA AATTGATCCC CTATCACACT TGAAATAAAA AATATCTTTA     120

TCCTTTAACA CCAAATAAAA TTCAGATTGG TCAATATGAA TGTATTCACT TAGTAATTCA     180

ACGAACTTAT TTATTAATTC TGATACACAC ACTGATTCTG TATTGTTTAT CGAAAACTTT     240

ACTCTTCCTG TATCAGTTTC TAAAAAAATA TTAACAAGTT CCATTTATAT CATCCAATAT     300

TATTGAAATG GTGGTAATAG ACAAATGATA TAGGTAAGAC GGCACAGTAC CTTTGTCGAC     360

CATCTCCTCC ATTTCATGCT CTATCTTATC ATGAACTTTG ATATGTGAAA ACAATACACC     420

ACATGCTTCT ATAACAGTAT GTAACACTTT AGATACAAAA TGCTTGATAC CATCGTAATT     480

GTTCAACACG GCCAATCTAT AATAGATAGT AGCTACTATA TATTCTATGA TAGTATTGAA     540

GAAGATAACC ACCTTGGCAT ATTGGTCATT TAATACAGAC ATGGTATCAA CAGATAGCTT     600

AAACGATAGG GAATCCGTGA ATGGAATAAG CGTTTCATTG ATTGAATATC CATATACTAA     660

CATATCGGAT ATCCTGATGT GTTCCATTAA ATCGTTAAGT TTTTTCTTTT TAACCTCGTT     720

GAACATCATT TCTGTTAACG GTCCCCAACA TCTTTGACCA ATTAATTTTT GATTTATTTT     780

TCCATGTATG GCGTATCTAG TCAGGTCGTA TAACCTATCC AATAATCCAT CATCGGTATC     840

CAAATTACAT ACTATGCTTT TCAATTCTCT ATAGAAAAGA TTAATACATC TAGAACAACA     900

ACATGATGTA ATATCTTTAT CATCAACAGA TGTGATATAT TTGAAGATTT TTCTATGATA     960

ATGAAGAATT TTTGAGAATA CTGTATTAAT GGTGTCTGTT ACCATGATCC CTTTGATTGC    1020

TGACAGAGTC AGCGAGCATG ATTTCCAATC TTTAACAATT TTTATTACCA TTATCTTTGT    1080

TTTAATGTCT ATAGATGATA ACATAACACG TCTAACAATA CACGGATTAA GACGGAAAGA    1140

TGAAATTATT CTTTCAACAT CTCCAATGGA TAACTTACTA TTTCGACGTG CATTGTCTAT    1200

ATGCTCGAGA ACATCCTCCA ACGAGTCTGT ATCTTTTTTG ATTATCGTCG ATCTCAACGA    1260

TTTGGGTCGT CTAGATCGTC GGACTCTATC ACCAGATGGC ATAGTTATTA GTCTTCTTTC    1320

TGTTTTCATA ATGAAATTTC TAAATTCATC TGCGAATCTT CTATATCTAA AATCATAATA    1380

TGCGATATTT GTTTCAACAA ATTTCCGTTC GTCCAATGTC AACATATCTA TCTCGGTTTC    1440

ATACCCTAAA TTGAACATGG CTACGGATTT AATTTTATAT TCATCTATCA ACTCTTCTTC    1500

AACAATAACA GAGTATAGAT AATCATTTAA TCCATCATAC ATAGTAGGAA GATTCTCGTT    1560

AACAAATTGT TTAACTGCAC TGATAAAACT GGGACTATAT TTGATATCTT GTCTAATAAA    1620

ATTAATAACA TTGTCCAAAG GATACTTTTT AACTAGATTT ATACATATCT GTTCATCAGT    1680

GAGGTTATGC AAAACATCGT GAATAGGTGG CACATTATAT TCATCAGATA TACTAATAAC    1740

AATTTCCAGA TCTATATTGT TTAATATATT ATATAGATGG AGCACGGAAG CTT           1793
```

(2) INFORMATION FOR SEQ ID NO:5:

(i) SEQUENCE CHARACTERISTICS:
        (A) LENGTH: 4491 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Raccoonpox virus ATCC# VR-838

(ix) FEATURE:
        (A) NAME/KEY: CDS
(B) LOCATION: 81..1

(ix) FEATURE:
(A) NAME/KEY: CDS
(B) LOCATION: 855..181

(ix) FEATURE:
(A) NAME/KEY: CDS
(B) LOCATION: 2152..812

(ix) FEATURE:
(A) NAME/KEY: CDS
(B) LOCATION: 2850..2194

(ix) FEATURE:
(A) NAME/KEY: CDS
(B) LOCATION: 3816..2950

(ix) FEATURE:
(A) NAME/KEY: CDS
(B) LOCATION: 4491..3970

(xi) SEQUENCE DESCRIPTION: SEQ ID NO:5:

```
AAGCTTTTTA AAATGATCAC TGTAATATGA TGAATCTGTA TCATTTCTCC AAATAATGTA     60

TCTGAATAGG AGATTTCTCA TATCTACTAA TGTATTTAGT TAGTAAACTA TTATTGTGTT    120

AAATAAGTAT TTATGAATTA GATAACAATT TTTAAAAGAC TATGTTTGAT ACAAAAAAAA    180

TTAATTTTGG AAATACTTGT CCCTCAAGTA ATCGGCAAAG CAATCTATAT AATCATATGT    240

GACATTATCA TATAATACAT GAATATATAC TGGATCGTAA CTAGTTAAGA TATACACGAA    300

TCCGATAACC TTTTTTACAT AATCAACAGG ATCTATTTTA AATGTATCGT ATCTAGTTCG    360

CTTTATTTTT CTGAATAGAT TAATGTTGTA ATTAGGATTT CTATGTATGT CTTTTATGGT    420

GTATTCCACG TAGCTACCAT AATGATCAAT AGCCAATTGT TTGTAAGTCA TTAGCTCTTT    480

TATTATGTTA CATTTGGTGT TACGTAGTTC ATCGCTGTTC ATTGCCAAGA ATCTATCTAC    540

AATTTTAAAT ACTTCAACGC CTGGATTATT AACCTGTTTC ATATACTGGG CTATATAATT    600

ATCAATATAT CGAGATGATA CAGCACCGTC GTACATTACA TACACATCTT CTCCTGAGTT    660

ATTCTGTGCT GATGGGCAGT TTAATACCTC CAGCATCTTG GTAACTTTAT TAGTATCCAT    720

TTTTTTAATA TCATCGAGTA ACACGGCTGA AGAATCACCA TCCATTACGA TAGCTATAAA    780

CACTAATCTA TATATTATTT TTATGTTATT TTTAAAGATC ATCAAAAACT TCATACGATA    840

CTCCTTCATG GACATAATTT GTTACAAAAT GTTTATATGT AGTAAAGTAT CTGCGATTTT    900

TGCAAAAATC TGGACGCATA AGACCAAAGT ATGCCAGGAA TGGAATAATA ATAGATTTAT    960

CGAGTTTATC CTTTTCTACT GATTTCATTG TTAGATACAT GGTCTCGGAA GTCGGATTAT   1020
```

-continued

```
GCAACATCAG TTTCGATAAT ATAACTGGAT TATTTAACCT GACACATTCG CTCATACAAG   1080

TATGCCCATT AACAACTGAG TCTACGCTAA AATGATTAAA CAATAGATAG TCTATCATCG   1140

TTTCGTATTC GAACAGAACA GCGTAGTACA TGGCATCTTC ACAAATTATA TCATTATCCA   1200

ATAGATATTT AACACATCTT ATAGATCCTG ACTTAACAGC TGTTTTAAAA TCATTAGAAT   1260

CAAATTGTCG TCCTTTATCA TTAATACTTT CTAGAATGTC ACATCTATCG TAAATGATAC   1320

ACAGATTAAC TAGTTGATCT GTTATAGAAT CACTAGTTGA TATCAATTTG TTAAAGAGAG   1380

ATACAGGAGT TAATGTTTTA ATGAGAATGG TAAGAGGACT ATCGCCGAAC TTGTTTTGTT   1440

TATTAACATC TGTTGATGGA AGCAAAAGAT CGATTATATC TATATTCTTG ACTGCTTTAG   1500

AACATGCAAT ATGGATAGGT GTATTTCCGT CATAATCTGC TCTTGAGGAA CTAATACCGA   1560

GTTTCATCAT CCACTCAATT GTACAAGCTT TTGGATTCTC AGACATAAGA TGTCTATGAA   1620

TATGATTTCT GCCAACTTTA TCTACTATCT TGGCCTCGAA TCCTATAGAC ATTAGTTTTT   1680

TGAACACTAT TTCTGACGGA TCTGTGCATG ATAGTAATGG TCCACATCCT TCTACATCAA   1740

CTGAGTTATT AATCTTAGCT CCGTGTTCCA CTAATAAATT TATTTTATCA ATTACATCAT   1800

CCTCGTTTCC GGAGAGATAA TACAGTGGAG TCTTATTTTG TTTATCGCAC GCGTTTGGAT   1860

TTGCACCATG CGTCAATAGC GTTGATATAA TTCTATTATT ATTGATTCTA GACGCTATAT   1920

GTAATGGATA ATCACCGTCA TCATTTGCTT CATTAGGCGA GTAGCCTTTA TTGATAAGTT   1980

CTTCTATGAA CTGCTCGTCT ATTCCTTTAA TTCCACAATA GATGTGTAAA ATACTATATT   2040

TTCCAGATGG TATTGTTGAC TGCAATATAT TTCTAAATAC ATCTAAATTC TTATGTTTTG   2100

ATTTGGCGTA AAGCGTTAGA TAATACTCGC TGTCAGGCAT GGTATCGTCC ATTGTTTCAT   2160

AAAAATGATA TTTCAATTTC TACTTTCTAC TTTTTACTCT CTATAACAAA TGTCGTAACT   2220

AACATTTTTT ATGTCAAGAA AGCAACTGTT TAGTTCATCT TTGAATGTTA CGCCATAACT   2280

ACCTTGTGAA GCGTAATCGG AATTCCGATA AAGAAATTTA TCAACTGGAT GAACAAACTT   2340

TGGATTAATA TTAATAGGAT CCATGCGGAG GTCGACACAT TTGACGCATG ATCCATTGAT   2400

AGTTATAGCA CATTCTGTTT CATGATTCAT TGCTTCTGTA AGTTCTGAAT CGTATTTTGT   2460

AGTTCCACAA TTCATTTCGG TACATGTTAT GGTTACACTA ATATTGTGCT GAAGTTTATC   2520

TAGTCGTTGA GTAGTAAACA ACAGAACTGA TAGTTTATAA TCTTCACCTA CTCCCTCTGC   2580

AGCTGCGACA AATCTCTGAT CCGTATCATA TATGGTCATA TTTATTTGTA ATCCATATCC   2640

TGTCAAACCT ATGTTTGCAT CTCTACCAGT GTAATTTTCA TACATGTGAC ACTCACCCAT   2700

AATAGTTTTG ATATCATAAT TAACACCAAT AGTGAGTTCG GCGGCAAAGT ACCAATAACG   2760

ATAATCACTT CGAGACGGAC ATTGCGTGTC TTTGTATTCT GAATAACCAA GAGATATGAC   2820

ACAAAAGAGT AAGAATAATC TGTAAACCAT CTTTAAAGAC TGCAACAGAT CTACTAGACA   2880

AGAGTCAATG ATAGAAACCA CTACTAAAAA AAATAATTAT TCTATCAATT TTAACCAATT   2940

GATCTTATTT TAAAATTGGG ATCTAAATAT TTTTGCAGAA TTGACATACA TGATTCTGAG   3000

TTCCTTATTT TTGCTAATTA TCTCATCCAA TTTATTATTC TTGACAACAT CGAGTTCTTT   3060

TATTAAATCA TCAGTCTTAT AGTCAACATG TTTTTCTATA ATCATTCTAG CTATTACAGG   3120

ATCATCCAAC AATACATTTT CCAGATTAAC AGAATAGATA TTAATGTCAT ATTTGAACAG   3180

AGTCCGTAGC AAATCTAAGT CTTTGTTCTC TATAGCCAAT TTGATGTCTG GGATGAAGAG   3240

AAGAGAGTTA TTGGTATTTG TTGCCATCAT ATAGTCTAGT AACAGAATCA GCATATCAAC   3300

ATTTCCATTT TTAATTGTGT CATGAATGCA ACTATAGAGA ATTGCCAGAT CAAAACTAGC   3360

TTTTAGCTCT GAAATAAAGT ATTCAGTAAT GCTGACATCA TTAAGCATAA CCGCCTTATA   3420
```

```
AAATGGGGTT TTCCATCCGG TTTTTCCATA GAACATCAGT TTCCATTTTT TCTTAATAAA    3480

CAGTTTTATA GTTTGGATAT TGCCGGCCTC CACGGCGTAA TACAATGGAG TATTACCTCG    3540

ATCATCAAAT TGCGAATCAT CCATCCCACT GAATAACAAA ATCTTTACTA TTTTAGTATC    3600

CTCTAACTTG GCTGCCTGAT GCAATGGAAA CTCATTCTCG AGAAGATTTT TCAATACCCC    3660

AGCATTAAGT AATTCACAAA CAAGACGCAC GTTATTATTA TCAATTGCAT AATACAACGC    3720

CGTACGTCCA TGAATATCAG CCTTAAATAA GTCCTTTCCG CCGATGAAGC TTTTCAACTG    3780

CTTAGACTTC CAGGTATTAA TTCGTGACAG ATCCATGTCT GAAACGAGAC GCTAAATACA    3840

GTGTATGTTT CATTTTTTAT AATTTTGCAT TACATCAATC CTCCAGAGTC AATAATATCT    3900

CTGATCGATG TGATCAATAG ATAAATGGCT ATCGCAAAAC AACACAACCA CATTTAATAA    3960

AAATAATATT CAAGGAGATT CAACCTTACC AATAAATAAT ATAAATCCAG TAATATCATG    4020

TCGGATGATA AACACAAATG GTTTATTGAA CTCTAGTTCT ACAGGTGCCG ATCTTCCTGT    4080

AGCCAACATT ATAGTAGACG CCTCTGCTAC TGTTCCTTGT TCATCAACAT CAATTTTAGC    4140

ATTCTGAAAC ATTTTATAGA TATATAATGG ATACTTGGTC ATGCGTTTAA ATGATGCATT    4200

GTCTGGATTA AACATACTGG GTGCAATCAT TTCGGCTATA GTCTTAATAT CTCTCTTATT    4260

TTCGATAGAA AATCTAGGAA GACTAAGATC ATACATTTTA TCCATTAATT GAGATGACCA    4320

ATAATCTAAT TTTGTGGTTG TGATAGAGTC CACAAAATGC GTGATATTAT CTCCAATTGC    4380

TATGTACATG CTAACATTAC TACCTTTATA TGGAAGTCTT ACCATGTCAT ATTCATAGTC    4440

ATCTACAGTA ATTGTGTTTC CTTGTAATTT AGCAACTAAA TTCATTGTTG G             4491
```

(2) INFORMATION FOR SEQ ID NO:6:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
Met Val Ile Leu Gln Pro Cys Tyr Ser Met Ile Leu Lys Lys Trp Ile
1               5                  10                  15

Leu Ile Lys Leu Pro Arg Cys Trp Arg Tyr
            20                  25
```

(2) INFORMATION FOR SEQ ID NO:7:

(i) SEQUENCE CHARACTERISTICS:
        (A) LENGTH: 224 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
Met Ser Met Lys Glu Tyr Arg Met Lys Phe Leu Met Ile Phe Lys Asn
1               5                  10                  15

Asn Ile Lys Ile Ile Tyr Arg Leu Val Phe Ile Ala Ile Val Met Asp
            20                  25                  30

Gly Asp Ser Ser Ala Val Leu Leu Asp Asp Ile Lys Lys Met Asp Thr
        35                  40                  45

Asn Lys Val Thr Lys Met Leu Glu Val Leu Asn Cys Pro Ser Ala Gln
```

```
            50                  55                  60
Asn Asn Ser Gly Glu Asp Val Tyr Val Met Tyr Asp Gly Ala Val Ser
 65                  70                  75                  80

Ser Arg Tyr Ile Asp Asn Tyr Ile Ala Gln Tyr Met Lys Gln Val Asn
                     85                  90                  95

Asn Pro Gly Val Glu Val Phe Lys Ile Val Asp Arg Phe Leu Ala Met
                    100                 105                 110

Asn Ser Asp Glu Leu Arg Asn Thr Lys Cys Asn Ile Ile Lys Glu Leu
                    115                 120                 125

Met Thr Tyr Lys Gln Leu Ala Ile Asp His Tyr Gly Ser Tyr Val Glu
                    130                 135                 140

Tyr Thr Ile Lys Asp Ile His Arg Asn Pro Asn Tyr Asn Ile Asn Leu
145                 150                 155                 160

Phe Arg Lys Ile Lys Arg Thr Arg Tyr Asp Thr Phe Lys Ile Asp Pro
                    165                 170                 175

Val Asp Tyr Val Lys Lys Val Ile Gly Phe Val Tyr Ile Leu Thr Ser
                    180                 185                 190

Tyr Asp Pro Val Tyr Ile His Val Leu Tyr Asp Asn Val Thr Tyr Asp
                    195                 200                 205

Tyr Ile Asp Cys Phe Ala Asp Tyr Leu Arg Asp Lys Tyr Phe Gln Asn
210                 215                 220
```

(2) INFORMATION FOR SEQ ID NO:8:

(i) SEQUENCE CHARACTERISTICS:
        (A) LENGTH: 446 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
Met Asp Asp Thr Met Pro Asp Ser Glu Tyr Tyr Leu Thr Leu Tyr Ala
 1               5                  10                  15

Lys Ser Lys His Lys Asn Leu Asp Val Phe Arg Asn Ile Leu Gln Ser
                 20                  25                  30

Thr Ile Pro Ser Gly Lys Tyr Ser Ile Leu His Ile Tyr Cys Gly Ile
                 35                  40                  45

Lys Gly Ile Asp Glu Gln Phe Ile Glu Glu Leu Ile Asn Lys Gly Tyr
 50                  55                  60

Ser Pro Asn Glu Ala Asn Asp Asp Gly Asp Tyr Pro Leu His Ile Ala
 65                  70                  75                  80

Ser Arg Ile Asn Asn Asn Arg Ile Ile Ser Thr Leu Leu Thr His Gly
                     85                  90                  95

Ala Asn Pro Asn Ala Cys Asp Lys Gln Asn Lys Thr Pro Leu Tyr Tyr
                    100                 105                 110

Leu Ser Gly Asn Glu Asp Asp Val Ile Asp Lys Ile Asn Leu Leu Val
                    115                 120                 125

Glu His Gly Ala Lys Ile Asn Asn Ser Val Asp Val Glu Gly Cys Gly
                    130                 135                 140

Pro Leu Leu Ser Cys Thr Asp Pro Ser Glu Ile Val Phe Lys Lys Leu
145                 150                 155                 160

Met Ser Ile Gly Phe Glu Ala Lys Ile Val Asp Lys Val Arg Gly Asn
                    165                 170                 175

His Ile His Arg His Leu Met Ser Glu Asn Pro Lys Ala Cys Thr Ile
```

-continued

```
                180                 185                 190
Glu Trp Met Met Lys Leu Gly Ile Ser Ser Arg Ala Asp Tyr Asp
        195                 200                 205
Gly Asn Thr Pro Ile His Ile Ala Cys Ser Lys Ala Val Lys Asn Ile
    210                 215                 220
Asp Ile Ile Asp Leu Leu Pro Ser Thr Asp Val Asn Lys Gln Asn
225                 230                 235                 240
Lys Phe Gly Asp Ser Pro Leu Thr Ile Leu Ile Lys Thr Lys Thr Pro
                245                 250                 255
Val Ser Leu Phe Asn Lys Leu Ile Ser Thr Ser Asp Ser Ile Thr Asp
            260                 265                 270
Gln Leu Val Asn Leu Cys Ile Ile Tyr Asp Arg Cys Asp Ile Leu Glu
        275                 280                 285
Ser Ile Asn Asp Lys Gly Arg Gln Phe Asp Ser Asn Asp Phe Lys Thr
    290                 295                 300
Ala Val Lys Ser Gly Ser Ile Arg Cys Val Lys Tyr Leu Leu Asp Asn
305                 310                 315                 320
Asp Ile Ile Cys Glu Asp Ala Met Tyr Tyr Ala Val Leu Phe Glu Tyr
                325                 330                 335
Glu Thr Met Ile Asp Tyr Leu Leu Phe Asn His Phe Ser Val Asp Ser
            340                 345                 350
Val Val Asn Gly His Thr Cys Met Ser Glu Cys Val Arg Leu Asn Asn
        355                 360                 365
Pro Val Ile Leu Ser Lys Leu Met Leu His Asn Pro Thr Ser Glu Thr
    370                 375                 380
Met Tyr Leu Thr Met Lys Ser Val Glu Lys Asp Lys Leu Asp Lys Ser
385                 390                 395                 400
Ile Ile Ile Pro Phe Leu Ala Tyr Phe Gly Leu Met Arg Pro Asp Phe
                405                 410                 415
Cys Lys Asn Arg Arg Tyr Phe Thr Thr Tyr Lys His Phe Val Thr Asn
            420                 425                 430
Tyr Val His Glu Gly Val Ser Tyr Glu Val Phe Asp Asp Leu
        435                 440                 445
```

(2) INFORMATION FOR SEQ ID NO:9:

(i) SEQUENCE CHARACTERISTICS:
        (A) LENGTH: 218 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
Met Val Tyr Arg Leu Phe Leu Leu Phe Cys Val Ile Ser Leu Gly Tyr
1               5                   10                  15
Ser Glu Tyr Lys Asp Thr Gln Cys Pro Ser Arg Ser Asp Tyr Arg Tyr
                20                  25                  30
Trp Tyr Phe Ala Ala Glu Leu Thr Ile Gly Val Asn Tyr Asp Ile Lys
            35                  40                  45
Thr Ile Met Gly Glu Cys His Met Tyr Glu Asn Tyr Thr Gly Arg Asp
        50                  55                  60
Ala Asn Ile Gly Leu Thr Gly Tyr Gly Leu Gln Ile Asn Met Thr Ile
65                  70                  75                  80
Tyr Asp Thr Asp Gln Arg Phe Val Ala Ala Ala Glu Gly Val Gly Glu
```

-continued

```
                        85                   90                    95
Asp Tyr Lys Leu Ser Val Leu Phe Thr Gln Arg Leu Asp Lys
                100                 105                 110

Leu Gln His Asn Ile Ser Val Thr Ile Thr Cys Thr Glu Met Asn Cys
            115                 120                 125

Gly Thr Thr Lys Tyr Asp Ser Glu Leu Thr Glu Ala Met Asn His Glu
        130                 135                 140

Thr Glu Cys Ala Ile Thr Ile Asn Gly Ser Cys Val Lys Cys Val Asp
145                 150                 155                 160

Leu Arg Met Asp Pro Ile Asn Ile Asn Pro Lys Phe Val His Pro Val
                165                 170                 175

Asp Lys Phe Leu Tyr Arg Asn Ser Asp Tyr Ala Ser Gln Gly Ser Tyr
            180                 185                 190

Gly Val Thr Phe Lys Asp Glu Leu Asn Ser Cys Phe Leu Asp Ile Lys
            195                 200                 205

Asn Val Ser Tyr Asp Ile Cys Tyr Arg Glu
            210                 215
```

(2) INFORMATION FOR SEQ ID NO:10:

(i) SEQUENCE CHARACTERISTICS:
        (A) LENGTH: 288 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
Met Asp Leu Ser Arg Ile Asn Thr Trp Lys Ser Lys Gln Leu Lys Ser
1               5                   10                  15

Phe Ile Gly Gly Lys Asp Leu Phe Lys Ala Asp Ile His Gly Arg Thr
            20                  25                  30

Ala Leu Tyr Tyr Ala Ile Asp Asn Asn Asn Val Arg Leu Val Cys Glu
            35                  40                  45

Leu Leu Asn Ala Gly Val Leu Lys Asn Leu Leu Glu Asn Glu Phe Pro
50                  55                  60

Leu His Gln Ala Ala Lys Leu Glu Asp Thr Lys Ile Val Lys Ile Leu
65                  70                  75                  80

Leu Phe Ser Gly Met Asp Asp Ser Gln Phe Asp Asp Arg Gly Asn Thr
            85                  90                  95

Pro Leu Tyr Tyr Ala Val Glu Ala Gly Asn Ile Gln Thr Ile Lys Leu
            100                 105                 110

Phe Ile Lys Lys Lys Trp Lys Leu Met Phe Tyr Gly Lys Thr Gly Trp
            115                 120                 125

Lys Thr Pro Phe Tyr Lys Ala Val Met Leu Asn Asp Val Ser Ile Thr
        130                 135                 140

Glu Tyr Phe Ile Ser Glu Leu Lys Ala Ser Phe Asp Leu Ala Ile Leu
145                 150                 155                 160

Tyr Ser Cys Ile His Asp Thr Ile Lys Asn Gly Asn Val Asp Met Leu
                165                 170                 175

Ile Leu Leu Leu Asp Tyr Met Met Ala Thr Asn Thr Asn Asn Ser Leu
            180                 185                 190

Leu Phe Ile Pro Asp Ile Lys Leu Ala Ile Glu Asn Lys Asp Leu Asp
            195                 200                 205

Leu Leu Arg Thr Leu Phe Lys Tyr Asp Ile Asn Ile Tyr Ser Val Asn
```

-continued

```
        210             215             220
Leu Glu Asn Val Leu Leu Asp Asp Pro Val Ile Ala Arg Met Ile Ile
225             230             235             240

Glu Lys His Val Asp Tyr Lys Thr Asp Asp Leu Ile Lys Glu Leu Asp
            245             250             255

Val Val Lys Asn Asn Lys Leu Asp Glu Ile Ile Ser Lys Asn Lys Glu
            260             265             270

Leu Arg Ile Met Tyr Val Asn Ser Ala Lys Ile Phe Arg Ser Gln Phe
        275             280             285
```

(2) INFORMATION FOR SEQ ID NO:11:

(i) SEQUENCE CHARACTERISTICS:
        (A) LENGTH: 173 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
Pro Thr Met Asn Leu Val Ala Lys Leu Gln Gly Asn Thr Ile Thr Val
1               5               10              15

Asp Asp Tyr Glu Tyr Asp Met Val Arg Leu Pro Tyr Lys Gly Ser Asn
            20              25              30

Val Ser Met Tyr Ile Ala Ile Gly Asp Asn Ile Thr His Phe Val Asp
        35              40              45

Ser Ile Thr Thr Thr Lys Leu Asp Tyr Trp Ser Ser Gln Leu Met Asp
    50              55              60

Lys Met Tyr Asp Leu Ser Leu Pro Arg Phe Ser Ile Glu Asn Lys Arg
65              70              75              80

Asp Ile Lys Thr Ile Ala Glu Met Ile Ala Pro Ser Met Phe Asn Pro
            85              90              95

Asp Asn Ala Ser Phe Lys Arg Met Thr Lys Tyr Pro Leu Tyr Ile Tyr
            100             105             110

Lys Met Phe Gln Asn Ala Lys Ile Asp Val Asp Glu Gln Gly Thr Val
            115             120             125

Ala Glu Ala Ser Thr Ile Met Leu Ala Thr Gly Arg Ser Ala Pro Val
            130             135             140

Glu Leu Glu Phe Asn Lys Pro Phe Val Phe Ile Ile Arg His Asp Ile
145             150             155             160

Thr Gly Phe Ile Leu Phe Ile Gly Lys Val Glu Ser Pro
            165             170
```

(2) INFORMATION FOR SEQ ID NO:12:

(i) SEQUENCE CHARACTERISTICS:
        (A) LENGTH: 672 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Raccoonpox virus ATCC# VR-838

(ix) FEATURE:

(A) NAME/KEY: CDS
           (B) LOCATION: 95..547

(xi) SEQUENCE DESCRIPTION: SEQ ID NO:12:

TATAACAGCT CGTGGAGTTG CTATATTATT TTTATGTTTT ATTGATAATT GTAAAAAAAA      60

CACACAATTA AATCGATAAG ATTGGGTAAT AACCATGGAG AGTAAATTAG ATTACGAGGA     120

CGCTGTTTTT TACTTTGTAT ACGACGACGA GTTATGCAGT CGTGACCTCA TTATCGATCT     180

AATTGATGAA TACGTCACGT GGAGAAATTA TATTATTGTA TTCGGTAAAG ATATTAACAA     240

ATGCGGAAGA CTATACAAGG AGTTGATGAA ATTTGACGAT GTTGCCATTA ATTACTATGG     300

GATGGATAAG ATCAATGAGA TTATTGATAC TATGAATGTC GGAGATAGAT ATATTAATCT     360

TAAAGAAGTC CATGATCAGG AAAGTCTGTT TGCCACCATC GGTATATGTG CCAAAATCAC     420

TGAAAATTGG GGTTATAAAA ATTTTTCAGA ATCTAGATTT CAATCATTAG GAAATATTAA     480

AGATTTGATG ACTGATGACA ACATAAATAC GTTGATGATT TTTCTAGAAA AAAAATTAGC     540

AGTATAATAT AGTTTTTTAT AAAAAGCATT AAATAGACTC GTATTATATT TTTGTTAAAA     600

AATTCATTAA CCCATTATAT ATTTTAAAGT CTTATATGTC ACAAACATGA AAACTGTAAT     660

TCCTATAAGC TT                                                         672

(2) INFORMATION FOR SEQ ID NO:13:

(i) SEQUENCE CHARACTERISTICS:
           (A) LENGTH: 150 amino acids
           (B) TYPE: amino acid
           (C) STRANDEDNESS: single
           (D) TOPOLOGY: linear (ii) MOLECULE TYPE: DNA (genomic)

(xi) SEQUENCE DESCRIPTION: SEQ ID NO:13:

Met Glu Ser Lys Leu Asp Tyr Glu Asp Ala Val Phe Tyr Phe Val Tyr
 1               5                  10                  15

Asp Asp Glu Leu Cys Ser Arg Asp Leu Ile Ile Asp Leu Ile Asp Glu
            20                  25                  30

Tyr Val Thr Trp Arg Asn Tyr Ile Ile Val Phe Gly Lys Asp Ile Asn
        35                  40                  45

Lys Cys Gly Arg Leu Tyr Lys Glu Leu Met Lys Phe Asp Asp Val Ala
    50                  55                  60

Ile Asn Tyr Tyr Gly Met Asp Lys Ile Asn Glu Ile Ile Asp Thr Met
65                  70                  75                  80

Asn Val Gly Asp Arg Tyr Ile Asn Leu Lys Glu Val His Asp Gln Glu
                85                  90                  95

Ser Leu Phe Ala Thr Ile Gly Ile Cys Ala Lys Ile Thr Glu Asn Trp
           100                 105                 110

Gly Tyr Lys Asn Phe Ser Glu Ser Arg Phe Gln Ser Leu Gly Asn Ile
       115                 120                 125

Lys Asp Leu Met Thr Asp Asp Asn Ile Asn Thr Leu Met Ile Phe Leu
   130                 135                 140

Glu Lys Lys Leu Ala Val
145                 150

(2) INFORMATION FOR SEQ ID NO:14:

(i) SEQUENCE CHARACTERISTICS:
           (A) LENGTH: 38 base pairs
           (B) TYPE: nucleic acid
           (C) STRANDEDNESS: double (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Raccoonpox virus ATCC# VR-838

(xi) SEQUENCE DESCRIPTION: SEQ ID NO:14:

CCGAAGCTTC CGTGCTCCAT CTATATAATA TATTAAAC 38

(2) INFORMATION FOR SEQ ID NO:15:

(i) SEQUENCE CHARACTERISTICS:
(A) LENGTH: 38 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Raccoonpox virus ATCC# VR-838

(xi) SEQUENCE DESCRIPTION: SEQ ID NO:15:

AATAAGCTTC CCGTTACTTT AGTAAAATCT TTTACAAA 38

(2) INFORMATION FOR SEQ ID NO:16:

(i) SEQUENCE CHARACTERISTICS:
(A) LENGTH: 40 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Swine influenza virus (xi) SEQUENCE DESCRIPTION: SEQ ID NO:16:

CCGAGGATCC GGCAATACTA TTAGTCTTGC TATGTACATT 40

(2) INFORMATION FOR SEQ ID NO:17:

(i) SEQUENCE CHARACTERISTICS:
(A) LENGTH: 39 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Swine influenza virus (xi) SEQUENCE DESCRIPTION: SEQ ID NO:17:

```
CTCTGGGATC CTAATTTTAA ATACATATTC TGCACTGTA                                    39

(2) INFORMATION FOR SEQ ID NO:18:

(i) SEQUENCE CHARACTERISTICS:
         (A) LENGTH: 39 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Swine influenza virus (xi) SEQUENCE DESCRIPTION: SEQ ID NO:18:

CCGAGGATCC GGCAATACTA TTAGTCTTGC TATGTACAT                                    39

(2) INFORMATION FOR SEQ ID NO:19:

(i) SEQUENCE CHARACTERISTICS:
         (A) LENGTH: 37 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Swine influenza virus (xi) SEQUENCE DESCRIPTION: SEQ ID NO:19:

CTCTGGATCC TAATTTAAAT ACATATTCTG CACTGTA                                      37

(2) INFORMATION FOR SEQ ID NO:20:

(i) SEQUENCE CHARACTERISTICS:
         (A) LENGTH: 39 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Swine influenza virus (xi) SEQUENCE DESCRIPTION: SEQ ID NO:20:

AATGAATTCA AATCAAAAAA TAATAACCAT TGGGTCAAT                                    39

(2) INFORMATION FOR SEQ ID NO:21:

(i) SEQUENCE CHARACTERISTICS:
         (A) LENGTH: 36 base pairs
         (B) TYPE: nucleic acid
         (C) STRANDEDNESS: double
         (D) TOPOLOGY: linear (ii) MOLECULE TYPE: DNA (genomic)
```

(iii) HYPOTHETICAL: NO (iv) ANTI-SENSE: NO (vi) ORIGINAL SOURCE:
              (A) ORGANISM: Swine influenza virus (xi) SEQUENCE DESCRIPTION: SEQ ID NO:21:

GGAAGATCTA CTTGTCAATG GTGAATGGCA GATCAG                                      36

(2) INFORMATION FOR SEQ ID NO:22:

(i) SEQUENCE CHARACTERISTICS:
              (A) LENGTH: 38 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Porcine respiratory reproductive syndrome virus (xi) SEQUENCE DESCRIPTION: SEQ ID NO:22:

TTCGAATTCG GCTAATAGCT GTACATTCCT CCATATTT                                    38

(2) INFORMATION FOR SEQ ID NO:23:

(i) SEQUENCE CHARACTERISTICS:
              (A) LENGTH: 30 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Porcine respiratory reproductive syndrome virus (xi) SEQUENCE DESCRIPTION: SEQ ID NO:23:

GGGGATCCTA TCGCCGTACG GCACTGAGGG                                             30

(2) INFORMATION FOR SEQ ID NO:24:

(i) SEQUENCE CHARACTERISTICS:
              (A) LENGTH: 34 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Porcine respiratory reproductive syndrome virus (xi) SEQUENCE DESCRIPTION: SEQ ID NO:24:

CCGAATTCGG CTGCGTCCCT TCTTTTCCTC ATGG                                        34

(2) INFORMATION FOR SEQ ID NO:25:

(i) SEQUENCE CHARACTERISTICS:
            (A) LENGTH: 38 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Porcine respiratory reproductive syndrome virus (xi) SEQUENCE DESCRIPTION: SEQ ID NO:25:

CTGGATCCTT CAAATTGCCA ACAGAATGGC AAAAAGAC                                38

(2) INFORMATION FOR SEQ ID NO:26:

(i) SEQUENCE CHARACTERISTICS:
            (A) LENGTH: 33 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Porcine respiratory reproductive syndrome virus (xi) SEQUENCE DESCRIPTION: SEQ ID NO:26:

TTGAATTCGT TGGAGAAATG CTTGACCGCG GGC                                     33

(2) INFORMATION FOR SEQ ID NO:27:

(i) SEQUENCE CHARACTERISTICS:
            (A) LENGTH: 34 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Porcine respiratory reproductive syndrome virus (xi) SEQUENCE DESCRIPTION: SEQ ID NO:27:

GAAGGATCCT AAGGACGACC CCATTGTTCC GCTG                                    34

(2) INFORMATION FOR SEQ ID NO:28:

(i) SEQUENCE CHARACTERISTICS:
            (A) LENGTH: 201 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO

```
      (vi) ORIGINAL SOURCE:
           (A) ORGANISM: Escherichia coli (xi) SEQUENCE DESCRIPTION: SEQ ID NO:28:

AGATCTTCCA TAATTAATTA ACCCTCGACT CTAGATTTTT TTTTTTTTTT TTTTTGGCAT      60

ATAAATAGAT CTGTATCCTA AAATTGAATT GTAATTATCG ATAATAAATG AATTCGGATC     120

CATAATTAAT TAATTTTTAT CCCGGCGCGC CGGGTCGAGG GTCGACCTGC AGGGCGGCCG     180

CGGCCCTCGA GGCCAAGCTT G                                              201

(2) INFORMATION FOR SEQ ID NO:29:

(i) SEQUENCE CHARACTERISTICS:
          (A) LENGTH: 189 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Escherichia coli (xi) SEQUENCE DESCRIPTION: SEQ ID NO:29:

AGATCTTCCA TAATTAATTA ACCCTCGACT CTAGATTTTT TTTTTTTTTT TTTTTGGCAT      60

ATAAATAGAT CTGTATCCTA AAATTGAATT GTAATTATCG ATAATAAATG AATTCGGATC     120

CATAATTAAT TAATTTTTAT CCCGGCGCGC CGGGTCGAGG GTCGACCTGC AGGGCGGCCG     180

CGGCCCTCG                                                            189

(2) INFORMATION FOR SEQ ID NO:30:

(i) SEQUENCE CHARACTERISTICS:
          (A) LENGTH: 90 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Raccoonpox virus ATCC# VR-838

(xi) SEQUENCE DESCRIPTION: SEQ ID NO:30:

ATAGGTAAGA CGGCACAGTA CCTTTGTCGA CCATCTCCTC CACATTTATA TCATCCAATA      60

TTATTGAAAT GGTGGTAATA GACAAATGAT                                      90

(2) INFORMATION FOR SEQ ID NO:31:

(i) SEQUENCE CHARACTERISTICS:
          (A) LENGTH: 37 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO
```

(vi) ORIGINAL SOURCE:
    (A) ORGANISM: Porcine parvovirus (xi) SEQUENCE DESCRIPTION: SEQ ID NO:31:

```
CTAAGGATCC GAGTGAAAAT GTGGAACAAC ACAACCC                                37
```

(2) INFORMATION FOR SEQ ID NO:32:

(i) SEQUENCE CHARACTERISTICS:
      (A) LENGTH: 38 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Porcine parvovirus (xi) SEQUENCE DESCRIPTION: SEQ ID NO:32:

```
GTGGATCCTA GTATAATTTT CTTGGTATAA GTTGTGAA                               38
```

(2) INFORMATION FOR SEQ ID NO:33:

(i) SEQUENCE CHARACTERISTICS:
      (A) LENGTH: 2375 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 1..738

(ix) FEATURE:
      (A) NAME/KEY: CDS
      (B) LOCATION: 799..2375

(ix) FEATURE:
      (A) NAME/KEY: unsure
      (B) LOCATION: 1106

(ix) FEATURE:
      (A) NAME/KEY: unsure
      (B) LOCATION: 1109

(xi) SEQUENCE DESCRIPTION: SEQ ID NO:33:

```
AAGCTTGTTA AACATGGCGA TTTATGGATA GCCAATTATA CATCTAAAGA CAGTCACCGT        60

AGGTATTTGT GTACTGTAAC GACAAAGAAT GGAGATTGTG TTCAGGGTAT AGTTAGATCT       120

CATATTAGGA AACCTTCATG TATTCCACAA ACCTATGAAC TAGGTACTCA CGATAAGTAT       180

GGTATAGACT TATATTGTGG AATTCTTTAC GCAAACCATT ATGATAATAT AACTTGGTAT       240

AAAAATAATC AAGAAATCAA TATCGACGGT ATTAAGTATT CTCAATCGGA TAAGAATTTA       300

ATTATTCACA GTCCAGAGTT AGAAGATAGT GGAAGATACA ATTGTTATGT TCACTACAAT       360

GACGTTAAAA ACAAGGACGA TATCATCGTA TCAAGATGTA GAATGCTTAC AGTTATACCG       420

TCACAAGACC ACAGGTTTAA ACTAATACTA GATCCGAAAA TCAATGCGAC AATAGGAAAA       480
```

```
CCTGCCAACA TAACATGTAT GGCGGTTACT AGTTCGCTAT CGATTGATGA TTTACTAATA     540

GAATGGGAAG ATCCATCCGG ATGGTTTATA GGATTCGATT TTGATGTATA TGCGGTTTTA     600

TATAGTGAAG GTGGTGGTAT CACCAGGTCG ACATTGTATT TTGAAAATGT TACTGAAGAA     660

TATATAGGTA ATACATATAC CTGTCGTGGA CACAACTATT ATTTTCAGAA AACCCTTACG     720

ACCACAGTAG TATTGGAGTA AACAACTAAC ATTTTTATAT TACTGAAATT TAACGTATAA     780

TCCTCGTTTC TATATAAAAT GGATGAAGAT AGGATGCTAC TAACTAAGTA TATGTATCTC     840

ACTGATAGAG AACATATAAA TATAGACTCT GTTAAACGGT TATGTGAAAT ATCGGATCCT     900

AATGCGTGTT ATAGATCAGG ATGTACCGCT TTACACGAGT ACTTTTATAA TTGTAGATCA     960

ATCAAAGGAA AATACGATTA TAGGTATAAT GGTTATTATA AATATTATTA TTCAGGAGAT    1020

TATGAAAACT ATAACAGTAA TTATGATCAT GCTATAGATA TGACAGACGA TGACGACACG    1080

GAAGATGATG AATCATCTGA AACAANATNT GAATTTTATG ATGAAACACA AGATCAAAAT    1140

AATCAGCTAA TATGTTCTAA TATTAAACTC ACAAATAGAG TAGATGATTT CGTAGATGAA    1200

TTCTATGGTT ACGATCAGAA TATCGACATA AATGATTATG TAGATAAATC TATAAAACAT    1260

GTAGTATATG GAAGCGATAA TAGGCGAATG CGATGGTGTG ATGTATGGAG ATGTCACCAT    1320

AGCGGATCAT ACAGATTCGG TAAGGAATGT ATAGACAATA TATATGAAGA TAATAATACA    1380

AAAATAGAAT TCGATAATTT CGATTCGTTG TCAAACCTTA CTGATGCGGA ATATGTAATT    1440

CGGGTAACTA GAGATGCGTC TACACAAATA TGGGAAAAGA AATCAGTGTT AGATAGATAC    1500

ATGGAGTCAT ATAGCCGTAA CCGATATAGT AAACATTCTG TCTTTAAGGG ATTTTCTGAT    1560

TACGTTAGAA AAAATGATTT AGATATGAAT ATTGTTAAAG AACTACTTTC GAACGGCGCA    1620

TCGCTGACAA TCAATGATGG AAGTCGTTGG GACCCCATCT TAGTGTACTT CAGAAGAACT    1680

ATAATGAATT TAGACATGAT CGATATTATT AACAATCATA CAACTATAGA TGAACGAAAG    1740

TATATAGTAC ACATCTATCT AAACAATTAC AGAAATTTCG ATTACCCATT CTTTAGGAAG    1800

TTAGTCATAA CCAATAAACA TTGTCTTAAG AATTATTATA CTAATCATGA TGATATATAC    1860

GGCACACCAC TTCATATGTT ATCATCTAAT AAAAAATTAA TAACGCCTAA TTACATTAAA    1920

TTATTGGTAT ATAACGGAAA TGATATAAAC GCGCGAGGGA ATGAGTCATA TATGAGAACT    1980

CCATTACATC ATTATTTAAG TAAAATGGTT TATCACGATA GAGAATATGA TGTTGGATAT    2040

TATAATGAAA AGATTATAGA TGCCTTTATA GAATTAGGAG CCGATCTAAC GATTGCGGAT    2100

AATAATGAGA TGATACCAGT AATTCATGCT ATTCATAGAA ATTCCGCATG TGATGGTTAC    2160

ATCAATACCA ATAATATAAA GATAATAAGT AAACTACTTA ATCTCAGTAG ACACGCACCG    2220

CATAATCTAT TTAGGGATCG CGTAATGCAT GATTATATAA TTAATTCATA TACTAATCTT    2280

GAATGTTTGG ATATTATTAG ATCACTGGAT GGATTTGATA TTAATTGTTA CTTTAACGGA    2340

CATACACCAC TTCATTGTGC CATAATTAAA AGCTT                                2375
```

(2) INFORMATION FOR SEQ ID NO:34:

(i) SEQUENCE CHARACTERISTICS:
        (A) LENGTH: 246 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

```
Lys Leu Val Lys His Gly Asp Leu Trp Ile Ala Asn Tyr Thr Ser Lys
1               5                   10                  15
```

```
Asp Ser His Arg Arg Tyr Leu Cys Thr Val Thr Thr Lys Asn Gly Asp
             20                  25                  30

Cys Val Gln Gly Ile Val Arg Ser His Ile Arg Lys Pro Ser Cys Ile
         35                  40                  45

Pro Gln Thr Tyr Glu Leu Gly Thr His Asp Lys Tyr Gly Ile Asp Leu
     50                  55                  60

Tyr Cys Gly Ile Leu Tyr Ala Asn His Tyr Asp Asn Ile Thr Trp Tyr
 65                  70                  75                  80

Lys Asn Asn Gln Glu Ile Asn Ile Asp Gly Ile Lys Tyr Ser Gln Ser
                 85                  90                  95

Asp Lys Asn Leu Ile Ile His Ser Pro Glu Leu Glu Asp Ser Gly Arg
             100                 105                 110

Tyr Asn Cys Tyr Val His Tyr Asn Asp Val Lys Asn Lys Asp Asp Ile
             115                 120                 125

Ile Val Ser Arg Cys Arg Met Leu Thr Val Ile Pro Ser Gln Asp His
         130                 135                 140

Arg Phe Lys Leu Ile Leu Asp Pro Lys Ile Asn Ala Thr Ile Gly Lys
145                 150                 155                 160

Pro Ala Asn Ile Thr Cys Met Ala Val Thr Ser Ser Leu Ser Ile Asp
                 165                 170                 175

Asp Leu Leu Ile Glu Trp Glu Asp Pro Ser Gly Trp Phe Ile Gly Phe
             180                 185                 190

Asp Phe Asp Val Tyr Ala Val Leu Tyr Ser Glu Gly Gly Gly Ile Thr
             195                 200                 205

Arg Ser Thr Leu Tyr Phe Glu Asn Val Thr Glu Glu Tyr Ile Gly Asn
         210                 215                 220

Thr Tyr Thr Cys Arg Gly His Asn Tyr Tyr Phe Gln Lys Thr Leu Thr
225                 230                 235                 240

Thr Thr Val Val Leu Glu
                 245

(2) INFORMATION FOR SEQ ID NO:35:

(i) SEQUENCE CHARACTERISTICS:
        (A) LENGTH: 525 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

Met Asp Glu Asp Arg Met Leu Leu Thr Lys Tyr Met Tyr Leu Thr Asp
 1               5                  10                  15

Arg Glu His Ile Asn Ile Asp Ser Val Lys Arg Leu Cys Glu Ile Ser
             20                  25                  30

Asp Pro Asn Ala Cys Tyr Arg Ser Gly Cys Thr Ala Leu His Glu Tyr
         35                  40                  45

Phe Tyr Asn Cys Arg Ser Ile Lys Gly Lys Tyr Asp Tyr Arg Tyr Asn
 50                  55                  60

Gly Tyr Tyr Lys Tyr Tyr Tyr Ser Gly Asp Tyr Glu Asn Tyr Asn Ser
 65                  70                  75                  80

Asn Tyr Asp His Ala Ile Asp Met Thr Asp Asp Asp Thr Glu Asp
                 85                  90                  95

Asp Glu Ser Ser Glu Thr Xaa Xaa Glu Phe Tyr Asp Glu Thr Gln Asp
             100                 105                 110
```

-continued

```
Gln Asn Asn Gln Leu Ile Cys Ser Asn Ile Lys Leu Thr Asn Arg Val
            115                 120                 125
Asp Asp Phe Val Asp Glu Phe Tyr Gly Tyr Asp Gln Asn Ile Asp Ile
130                 135                 140
Asn Asp Tyr Val Asp Lys Ser Ile Lys His Val Val Tyr Gly Ser Asp
145                 150                 155                 160
Asn Arg Arg Met Arg Trp Cys Asp Val Trp Arg Cys His His Ser Gly
                165                 170                 175
Ser Tyr Arg Phe Gly Lys Glu Cys Ile Asp Asn Ile Tyr Glu Asp Asn
            180                 185                 190
Asn Thr Lys Ile Glu Phe Asp Asn Phe Asp Ser Leu Ser Asn Leu Thr
            195                 200                 205
Asp Ala Glu Tyr Val Ile Arg Val Thr Arg Asp Ala Ser Thr Gln Ile
            210                 215                 220
Trp Glu Lys Lys Ser Val Leu Asp Arg Tyr Met Glu Ser Tyr Ser Arg
225                 230                 235                 240
Asn Arg Tyr Ser Lys His Ser Val Phe Lys Gly Phe Ser Asp Tyr Val
                245                 250                 255
Arg Lys Asn Asp Leu Asp Met Asn Ile Val Lys Glu Leu Leu Ser Asn
            260                 265                 270
Gly Ala Ser Leu Thr Ile Asn Asp Gly Ser Arg Trp Asp Pro Ile Leu
            275                 280                 285
Val Tyr Phe Arg Arg Thr Ile Met Asn Leu Asp Met Ile Asp Ile Ile
            290                 295                 300
Asn Asn His Thr Thr Ile Asp Glu Arg Lys Tyr Ile Val His Ile Tyr
305                 310                 315                 320
Leu Asn Asn Tyr Arg Asn Phe Asp Tyr Pro Phe Phe Arg Lys Leu Val
                325                 330                 335
Ile Thr Asn Lys His Cys Leu Lys Asn Tyr Tyr Thr Asn His Asp Asp
            340                 345                 350
Ile Tyr Gly Thr Pro Leu His Met Leu Ser Ser Asn Lys Lys Leu Ile
            355                 360                 365
Thr Pro Asn Tyr Ile Lys Leu Leu Val Tyr Asn Gly Asn Asp Ile Asn
370                 375                 380
Ala Arg Gly Asn Glu Ser Tyr Met Arg Thr Pro Leu His His Tyr Leu
385                 390                 395                 400
Ser Lys Met Val Tyr His Asp Arg Glu Tyr Asp Val Gly Tyr Tyr Asn
                405                 410                 415
Glu Lys Ile Ile Asp Ala Phe Ile Glu Leu Gly Ala Asp Leu Thr Ile
            420                 425                 430
Ala Asp Asn Asn Glu Met Ile Pro Val Ile His Ala Ile His Arg Asn
            435                 440                 445
Ser Ala Cys Asp Gly Tyr Ile Asn Thr Asn Asn Ile Lys Ile Ile Ser
            450                 455                 460
Lys Leu Leu Asn Leu Ser Arg His Ala Pro His Asn Leu Phe Arg Asp
465                 470                 475                 480
Arg Val Met His Asp Tyr Ile Ile Asn Ser Tyr Thr Asn Leu Glu Cys
                485                 490                 495
Leu Asp Ile Ile Arg Ser Leu Asp Gly Phe Asp Ile Asn Cys Tyr Phe
            500                 505                 510
Asn Gly His Thr Pro Leu His Cys Ala Ile Ile Lys Ser
            515                 520                 525
```

(2) INFORMATION FOR SEQ ID NO:36:

(i) SEQUENCE CHARACTERISTICS:
        (A) LENGTH: 3295 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Porcine reproductive respiratory virus
        (Eichelberger strain)

(ix) FEATURE:
        (A) NAME/KEY: CDS
        (B) LOCATION: 1..738

(ix) FEATURE:
        (A) NAME/KEY: CDS
        (B) LOCATION: 799..2375

(ix) FEATURE:
        (A) NAME/KEY: CDS
        (B) LOCATION: 1..738

(ix) FEATURE:
        (A) NAME/KEY: CDS
        (B) LOCATION: 799..2375

(ix) FEATURE:
        (A) NAME/KEY: CDS
        (B) LOCATION: 1..738

(ix) FEATURE:
        (A) NAME/KEY: CDS
        (B) LOCATION: 799..2375

(xi) SEQUENCE DESCRIPTION: SEQ ID NO:36:

```
GAATTCCCGG GCCCTGTCAT TGAACCAACT TTGGGCCTGA ACTGAAATGA AATGGGGCT      60
ATGCAAAGCC TTTTCGACAA AATTGGCCAA CTTTTTGTGG ATGCTTTCAC GGAATTTTTG    120
GTGTCCATTG TTGATATCAT CATATTTTTG GCCATTTTGT TTGGCTTCAC CATCGCAGGT    180
TGGCTGGTGG TCTTCTGCAT CCGATTGGTT TGCTCCGCGG TACTCCGTGC GCGCCCTACC    240
ATTCACCCTG AGCAATTACA GAAGATCCTA TGAAGCCTTT CTTTCTCAGT GCCAGGTGGA    300
CATTCCCACC TGGGGAATCA ACATCCCTT GGGGATGTTT TGGCACCATA AGGTGTCAAC     360
CCTGATTGAT GAAATGGTGT CGCGTCGAAT GTACCGCATC ATGGAAAAAG CAGGACAGGC    420
TGCCTGGAAA CAGGTGGTGA GGGAGGTTAC GCTGTCTCGC ATTAGTGGTT TGGACGTGGT    480
GGCTCATTTT CAGCATCTTG CCGCCATTGA AGCCGAGACC TGTAAATATT TGGCCTCTCG    540
GCTGCCCATG CTACACAACC TGCGCATGAC AGGGTCAAAT GTAACCATAG TGTATAATAG    600
CACTTCAAAT CAGGTGTTTG CTATTTTCC AACCCCTGGG TCCCGGCCAA AGCTTCATGA     660
TTTTCAGCAA TGGCTAATAG CTGTGCACTC CTCCATATTT TCCTCCGTAG CGGCTTCTTG    720
TACTCTTTTT GTTGTGCTGT GGTTGCGGAT CCCAATGCTA CGTTCTGTTT TTGGTTTCCA    780
CTGGTTAGGG GCAATTTTTC TTTCGAACTC ACGTGAATT ACACAGTGTG CCCACCTTGC     840
CTCACCCGGC AAGCAGCCGC TGAGATCTAC GAACCCGGCA GGTCTCTTTG GTGCAGGATA    900
GGGCATGACC GATGTGGTGA GGACGATCAT GACGAACTAG GGTTCATGGT TCCGCCTGGC    960
CTCTCCAGCG AAGGCCACTT GACCAGTGTT TACGCTTGGT TGGCGTTCCT GTCCTTCAGC   1020
```

-continued

```
TACACGGCCC AGTTCCATCC CGAGATATTT GGGATAGGGA ATGTGAGTAA AGTTTATGTT    1080

GACATCAAGC ACCAATTCAT CTGCGCCGAA CACGACGGGC GGAACGCCAC CCTGCTTCGC    1140

CATGACAATA TTTCAGCCGT GTTTCAGACC TACTACCAAC ATCAGGTCGA TGGCGGCAAT    1200

TGGTTTCACC TGGAATGGCT GCGTCCCTTC TTTTCCTCTT GGTTGGTTTT AAATGTTTCG    1260

TGGTTTCTCA GGCGTTCGCC TGCAAGCCAT GTTTCAGTTC GAGTCTTTCA GACATCAAAA    1320

CCAACACTAC CGCAGCATCA AACTTTGTTG TCCTCCAGGA CGTCAGCTGC CTTAGGCATG    1380

GCGACCCGTC CTCTCCGGCG ATTCGCAAAA GCCCTCAGTG CCGTACGGCG ATAGGAACAC    1440

CCGTGTATAT CACCACCACA GCCAATGTGA CAGATGAGAA TTATTTACAT TCTTCTGATC    1500

TCCTCATGCT TTCTTCTTGC CTTTTCTATG CTTCTGAAAT GAGTGAAAAG GGGTTCAAGG    1560

TGGTATTTGG CAATGTGTCA GGCATCGTGG CTGTGTGTGT CAACTTTACC AGCTACGTCC    1620

AACATGTCAA GGAGTTCACC CAACGCTCCT TGGTGGTCGA TCATGTGCGG CTGCTTCATT    1680

TCATGACACC TGAGACCATG AGGTGGGCAA CCGTTTTAGC CTGTCTTTTT GCCATCCTGC    1740

TGGCAATTTG AATGTTCAAG TATGTTGGGG AAATGCTTGA CCGCGGGCTG TTGCTCGCGA    1800

TTGCTTTCTT TGTGGTTTAT CGTGCCGTTC TGGTTTGCTG TGCTCGTCAA CGCCAACAGC    1860

AGCAGCAGCC CCCATTTTCA GTCGATTTAT AACTTGACGC TATGTGAGCT GAATGGCACA    1920

AATTGGCTGG CTGAAAAATT TGATTGGGCA GTGGAGACTT TTGTCATCTT TCCCGTGTTG    1980

ACTCACATTG TTTCCTATGG TGCACTTACC ACCAGCCATT TCCTTGACAC AGTTGGTCTG    2040

GTTGCTGTGT CCACCGCCGG TTTTTTTCAC GGGCGGTATG TCTTGAGTAG CATCTACGCG    2100

GTCTGTGCCC TGGCTGCGTT GATTTGCTTC GTCATCAGAT TTGCGAAGAA CTGCATGTCC    2160

TGGCGCTACT CATGTACCAG ATATACCAAC TTCCTTCTAG ATACTAAGGG CAGACTCTAT    2220

CGTTGGCGGT CGCCTGTTAT CATAGAGAAA GGGGGTAAGG TTGAGGTCGG AGGCCACCTG    2280

ATCGACCTCA AAAGAGTTGT GCTTGATGGT TCCGTGGCGA CTCCTTTAAC CAGAGTTTCA    2340

GCTGAACAAT GGGGTCGTCC CTAGACGACT TTTGCAATGA TAGCACGGCT CCGCAAAAAG    2400

TGCTTCTGGC GTTTTCCATC ACCTACACGC CAGTGATGAT ATATGCTCTA AAGGTAAGTC    2460

GCGGCCGACT GCTAGGGCTT CTGCACCTTT TGATCTTTCT GAATTGTGCT TTTACCTTCG    2520

GGTACATGAC ATTCGTGCAC TTTCAGAGCA CAAATAAGGT CGCGCTCACT ATGGGAGCAG    2580

TAGTTGCACT TCTTTGGGGG GTGTACTCAG CCATAGAAAC CTGGAAATTC ATCACCTCCA    2640

GATGCCGTTT GTGCTTGCTA GGCCGCAAGT ACATCCTGGC CCCTGCCCAC CACGTCGAAA    2700

GTGCCGCGGG CTTTCATCCG ATTGCGGCAA ATGATAACCA CGCATTTGTC GTCCGGCGTC    2760

CCGGCTCCAC TACGGTTAAC GGCACATTGG TGCCCGGGTT GAAAAGCCTC GTGTTGGGTG    2820

GCAGAAAAGC TGTTAAACAG GGAGTGGTAA ACCTTGTCAA ATATGCCAAA TAACAACGGC    2880

AAGCAGCAAA AGAAAAAGAA GGGGAATGGC CAGCCAGTCA ATCAGCTGTG CCAAATGCTG    2940

GGTAAGATCA TCGCCCAGCA AAACCAGTCC AGAGGCAAGG GACCGGGGAA GAAAAATAAG    3000

AAGAAAAACC CGGAGAAGCC CCATTTTCCT CTAGCGACCG AAGATGACGT CAGGCATCAC    3060

TTCACCCCTA GTGAGCGGCA ATTGTGTCTG TCGTCGATCC AGACTGCCTT TAACCAGGGC    3120

GCTGGAACTT GTACCCTGTC AGATTCAGGG AGGATAAGTT ACACTGTGGA GTTTAGTTTG    3180

CCGACGCATC ATACTGTGCG TCTGATTCGC GCTACAGCAT CACCCACAGC GTGATGGGCT    3240

GACATTCTTG AAGCACCTCA GTGTTTGAAT TGGAAGAATG CGTGGTGAAG GATCC         3295
```

(2) INFORMATION FOR SEQ ID NO:37:

-continued (i) SEQUENCE CHARACTERISTICS:
    (A) LENGTH: 256 amino acids
    (B) TYPE: amino acid
    (C) STRANDEDNESS: single
    (D) TOPOLOGY: linear (ii) MOLECULE TYPE: DNA (genomic)

(xi) SEQUENCE DESCRIPTION: SEQ ID NO:37:

```
Met Lys Trp Gly Leu Cys Lys Ala Phe Ser Thr Lys Leu Ala Asn Phe
1               5                   10                  15

Leu Trp Met Leu Ser Arg Asn Phe Trp Cys Pro Leu Leu Ile Ser Ser
            20                  25                  30

Tyr Phe Trp Pro Phe Cys Leu Ala Ser Pro Ser Gln Val Gly Trp Trp
                35                  40                  45

Ser Ser Ala Ser Asp Trp Phe Ala Pro Arg Tyr Ser Val Arg Ala Leu
50                  55                  60

Pro Phe Thr Leu Ser Asn Tyr Arg Arg Ser Tyr Glu Ala Phe Leu Ser
65                  70                  75                  80

Gln Cys Gln Val Asp Ile Pro Thr Trp Gly Ile Lys His Pro Leu Gly
                85                  90                  95

Met Phe Trp His His Lys Val Ser Thr Leu Ile Asp Glu Met Val Ser
                100                 105                 110

Arg Arg Met Tyr Arg Ile Met Glu Lys Ala Gly Gln Ala Ala Trp Lys
            115                 120                 125

Gln Val Val Arg Glu Val Thr Leu Ser Arg Ile Ser Gly Leu Asp Val
            130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Ser Asn Gln Val Phe Ala
            180                 185                 190

Ile Phe Pro Thr Pro Gly Ser Arg Pro Lys Leu His Asp Phe Gln Gln
            195                 200                 205

Trp Leu Ile Ala Val His Ser Ser Ile Phe Ser Ser Val Ala Ala Ser
210                 215                 220

Cys Thr Leu Phe Val Val Leu Trp Leu Arg Ile Pro Met Leu Arg Ser
225                 230                 235                 240

Val Phe Gly Phe His Trp Leu Gly Ala Ile Phe Leu Ser Asn Ser Arg
                245                 250                 255
```

(2) INFORMATION FOR SEQ ID NO:38:

(i) SEQUENCE CHARACTERISTICS:
    (A) LENGTH: 254 amino acids
    (B) TYPE: amino acid
    (C) STRANDEDNESS: single
    (D) TOPOLOGY: linear (ii) MOLECULE TYPE: DNA (genomic)

(xi) SEQUENCE DESCRIPTION: SEQ ID NO:38:

```
Met Ala Asn Ser Cys Ala Leu Leu His Ile Phe Leu Arg Ser Gly Phe
1               5                   10                  15

Leu Tyr Ser Phe Cys Cys Ala Val Val Ala Asp Pro Asn Ala Thr Phe
            20                  25                  30

Cys Phe Trp Phe Pro Leu Val Arg Gly Asn Phe Ser Phe Glu Leu Thr
            35                  40                  45
```

```
Val Asn Tyr Thr Val Cys Pro Pro Cys Leu Thr Arg Gln Ala Ala Ala
    50                  55                  60
Glu Ile Tyr Glu Pro Gly Arg Ser Leu Trp Cys Arg Ile Gly His Asp
65                  70                  75                  80
Arg Cys Gly Glu Asp Asp His Asp Glu Leu Gly Phe Met Val Pro Pro
                85                  90                  95
Gly Leu Ser Ser Glu Gly His Leu Thr Ser Val Tyr Ala Trp Leu Ala
                100                 105                 110
Phe Leu Ser Phe Ser Tyr Thr Ala Gln Phe His Pro Glu Ile Phe Gly
            115                 120                 125
Ile Gly Asn Val Ser Lys Val Tyr Val Asp Ile Lys His Gln Phe Ile
        130                 135                 140
Cys Ala Glu His Asp Gly Arg Asn Ala Thr Leu Leu Arg His Asp Asn
145                 150                 155                 160
Ile Ser Ala Val Phe Gln Thr Tyr Tyr Gln His Gln Val Asp Gly Gly
                165                 170                 175
Asn Trp Phe His Leu Glu Trp Leu Arg Pro Phe Phe Ser Ser Trp Leu
            180                 185                 190
Val Leu Asn Val Ser Trp Phe Leu Arg Arg Ser Pro Ala Ser His Val
        195                 200                 205
Ser Val Arg Val Phe Gln Thr Ser Lys Pro Thr Leu Pro Gln His Gln
210                 215                 220
Thr Leu Leu Ser Ser Arg Thr Ser Ala Ala Leu Gly Met Ala Thr Arg
225                 230                 235                 240
Pro Leu Arg Arg Phe Ala Lys Ala Leu Ser Ala Val Arg Arg
                245                 250

(2) INFORMATION FOR SEQ ID NO:39:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

Met Ala Ala Ser Leu Leu Phe Leu Leu Val Gly Phe Lys Cys Phe Val
1               5                   10                  15
Val Ser Gln Ala Phe Ala Cys Lys Pro Cys Phe Ser Ser Ser Leu Ser
            20                  25                  30
Asp Ile Lys Thr Asn Thr Thr Ala Ala Ser Asn Phe Val Val Leu Gln
        35                  40                  45
Asp Val Ser Cys Leu Arg His Gly Asp Pro Ser Ser Pro Ala Ile Arg
    50                  55                  60
Lys Ser Pro Gln Cys Arg Thr Ala Ile Gly Thr Pro Val Tyr Ile Thr
65                  70                  75                  80
Thr Thr Ala Asn Val Thr Asp Glu Asn Tyr Leu His Ser Ser Asp Leu
                85                  90                  95
Leu Met Leu Ser Ser Cys Leu Phe Tyr Ala Ser Glu Met Ser Glu Lys
            100                 105                 110
Gly Phe Lys Val Val Phe Gly Asn Val Ser Gly Ile Val Ala Val Cys
        115                 120                 125
Val Asn Phe Thr Ser Tyr Val Gln His Val Lys Glu Phe Thr Gln Arg
    130                 135                 140
```

-continued

```
Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile
```

(2) INFORMATION FOR SEQ ID NO:40:

(i) SEQUENCE CHARACTERISTICS:
        (A) LENGTH: 200 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

```
Met Leu Gly Lys Cys Leu Thr Ala Gly Cys Cys Ser Arg Leu Leu Ser
1               5                   10                  15

Leu Trp Phe Ile Val Pro Phe Trp Phe Ala Val Leu Val Asn Ala Asn
                20                  25                  30

Ser Ser Ser Ser Ser His Phe Gln Ser Ile Tyr Asn Leu Thr Leu Cys
            35                  40                  45

Glu Leu Asn Gly Thr Asn Trp Leu Ala Glu Lys Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Ala Val
                85                  90                  95

Ser Thr Ala Gly Phe Phe His Gly Arg Tyr Val Leu Ser Ser Ile Tyr
                100                 105                 110

Ala Val Cys Ala Leu Ala Ala Leu Ile Cys Phe Val Ile Arg Phe Ala
                115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Gly Gly His Leu Ile Asp Leu
                165                 170                 175

Lys Arg Val Val Leu Asp Gly Ser Val Ala Thr Pro Leu Thr Arg Val
                180                 185                 190

Ser Ala Glu Gln Trp Gly Arg Pro
            195                 200
```

(2) INFORMATION FOR SEQ ID NO:41:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

```
Met Gly Ser Ser Leu Asp Asp Phe Cys Asn Asp Ser Thr Ala Pro Gln
1               5                   10                  15

Lys Val Leu Leu Ala Phe Ser Ile Thr Tyr Thr Pro Val Met Ile Tyr
                20                  25                  30
```

```
Ala Leu Lys Val Ser Arg Gly Arg Leu Leu Gly Leu Leu His Leu Leu
            35                  40                  45

Ile Phe Leu Asn Cys Ala Phe Thr Phe Gly Tyr Met Thr Phe Val His
        50                  55                  60

Phe Gln Ser Thr Asn Lys Val Ala Leu Thr Met Gly Ala Val Val Ala
65                      70                  75                  80

Leu Leu Trp Gly Val Tyr Ser Ala Ile Glu Thr Trp Lys Phe Ile Thr
                    85                  90                  95

Ser Arg Cys Arg Leu Cys Leu Leu Gly Arg Lys Tyr Ile Leu Ala Pro
                100                 105                 110

Ala His His Val Glu Ser Ala Ala Gly Phe His Pro Ile Ala Ala Asn
            115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Lys Ala
                165                 170
```

(2) INFORMATION FOR SEQ ID NO:42:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

```
Met Pro Asn Asn Gly Lys Gln Gln Lys Lys Lys Gly Asn Gly
1               5                   10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
            35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
                100                 105                 110

Arg Leu Ile Arg Ala Thr Ala Ser Pro Thr Ala
            115                 120
```

(2) INFORMATION FOR SEQ ID NO:43:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
     (A) ORGANISM: Synthetic (xi) SEQUENCE DESCRIPTION: SEQ ID NO:43:

CTGAGAATTC ATGGGGGCTA TGCAAAGCCT TTTCG                              35

(2) INFORMATION FOR SEQ ID NO:44:

(i) SEQUENCE CHARACTERISTICS:
       (A) LENGTH: 34 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Synthetic (xi) SEQUENCE DESCRIPTION: SEQ ID NO:44:

GTGGAATTCA CCGTGAGTTC GAAAGAAAAA TTGC                               34

(2) INFORMATION FOR SEQ ID NO:45:

(i) SEQUENCE CHARACTERISTICS:
       (A) LENGTH: 38 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Synthetic (xi) SEQUENCE DESCRIPTION: SEQ ID NO:45:

CAATGAATTC TAGCTGTGCA CTCCTCCATA TTTTCCTC                           38

(2) INFORMATION FOR SEQ ID NO:46:

(i) SEQUENCE CHARACTERISTICS:
       (A) LENGTH: 31 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Synthetic (xi) SEQUENCE DESCRIPTION: SEQ ID NO:46:

CGGGAATTCC TATCGCCGTA CGGCACTGAG G                                  31

(2) INFORMATION FOR SEQ ID NO:47:

(i) SEQUENCE CHARACTERISTICS:
       (A) LENGTH: 34 base pairs (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic (xi) SEQUENCE DESCRIPTION: SEQ ID NO:47:

GGGAATTCTG CGTCCCTTCT TTTCCTCTTG GTTG                                    34

(2) INFORMATION FOR SEQ ID NO:48:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic (xi) SEQUENCE DESCRIPTION: SEQ ID NO:48:

CTTGGATCCT CAAATTGCCA GCAGGATGGC AAAAAG                                  36

(2) INFORMATION FOR SEQ ID NO:49:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic (xi) SEQUENCE DESCRIPTION: SEQ ID NO:49:

CAAGGAATTC GGGGAAATGC TTGACCGCGG GCTG                                    34

(2) INFORMATION FOR SEQ ID NO:50:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic (xi) SEQUENCE DESCRIPTION: SEQ ID NO:50:

AAAAGGATCC TAGGGACGAC CCCATTGTTC AGC                33

(2) INFORMATION FOR SEQ ID NO:51:

(i) SEQUENCE CHARACTERISTICS:
       (A) LENGTH: 37 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Synthetic (xi) SEQUENCE DESCRIPTION: SEQ ID NO:51:

CAATGAATTC GTCCCTAGAC GACTTTTGCA ATGATAG            37

(2) INFORMATION FOR SEQ ID NO:52:

(i) SEQUENCE CHARACTERISTICS:
       (A) LENGTH: 40 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Synthetic (xi) SEQUENCE DESCRIPTION: SEQ ID NO:52:

CTTGGGATCC TTATTTGGCA TATTTGACAA GGTTTACCAC         40

(2) INFORMATION FOR SEQ ID NO:53:

(i) SEQUENCE CHARACTERISTICS:
       (A) LENGTH: 37 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Synthetic (xi) SEQUENCE DESCRIPTION: SEQ ID NO:53:

TATGAATTCT AACAACGGCA AGCAGCAAAA GAAAAAG            37

(2) INFORMATION FOR SEQ ID NO:54:

(i) SEQUENCE CHARACTERISTICS:
       (A) LENGTH: 33 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Synthetic (xi) SEQUENCE DESCRIPTION: SEQ ID NO:54:

TGTGGATCCA TCACGCTGTG GGTGATGCTG TAG                                         33

(2) INFORMATION FOR SEQ ID NO:55:

(i) SEQUENCE CHARACTERISTICS:
             (A) LENGTH: 333 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Swinepox virus (xi) SEQUENCE DESCRIPTION: SEQ ID NO:55:

CTGGTGCCGG AAACCAGGCA AAGCGCCATT CGCCATTCAG GCTGCGCAAC TGTTGGGAAG         60

GGCGATCGGT GCGGGCCTCT TCGCTATTAC GCCAGCTGGC GAAAGGGGGA TGTGCTGCAA        120

GGCGATTAAG TTGGGTAACG CCAGGGTTTT CCCAGTCACG ACGTTGTAAA ACGACGGGAT        180

CTGTCATTTA TATAAATTAA TTCTAAATAA TATAGGATCC CGATCTTGTC GTATATGTTG        240

TGTTATTGAA TGCGTGTTTT CTACAAACTC TTTTATGCGT AGAAACTTTT AACGTTGGTG        300

TATCAAATGT CTAGAACTAG TGGATCCCCC GGG                                    333

(2) INFORMATION FOR SEQ ID NO:56:

(i) SEQUENCE CHARACTERISTICS:
             (A) LENGTH: 37 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Synthetic (xi) SEQUENCE DESCRIPTION: SEQ ID NO:56:

TTGGGCGCGC CATTTATCTA TTGATCACAT CGATCAG                                    37

(2) INFORMATION FOR SEQ ID NO:57:

(i) SEQUENCE CHARACTERISTICS:
             (A) LENGTH: 40 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO

-continued

```
    (iv) ANTI-SENSE: NO (vi) ORIGINAL SOURCE:
         (A) ORGANISM: Synthetic (xi) SEQUENCE DESCRIPTION: SEQ ID NO:57:

CCGGCGCGCC AGACTGCAAC AGATCTACTA GACAAGAGTC                           40

(2) INFORMATION FOR SEQ ID NO:58:

(i) SEQUENCE CHARACTERISTICS:
         (A) LENGTH: 333 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Synthetic (xi) SEQUENCE DESCRIPTION: SEQ ID NO:58:

CTGGTGCCGG AAACCAGGCA AAGCGCCATT CGCCATTCAG GCTGCGCAAC TGTTGGGAAG     60

GGCGATCGGT GCGGGCCTCT TCGCTATTAC GCCAGCTGGC GAAAGGGGGA TGTGCTGCAA    120

GGCGATTAAG TTGGGTAACG CCAGGGTTTT CCCAGTCACG ACGTTGTAAA ACGACGGGAT    180

CTGTCATTTA TATAAATTAA TTCTAAATAA TATAGGATCC CGATCTTGTC GTATATGTTG    240

TGTTATTGAA TGCGTGTTTT CTACAAACTC TTTTATGCGT AGAAACTTTT AACGTTGGTG    300

TATCAAATGT CTAGAACTAG TGGATCCCCC GGG                                 333
```